(12) United States Patent
Geijsen et al.

(10) Patent No.: US 8,524,498 B2
(45) Date of Patent: Sep. 3, 2013

(54) METHODS AND COMPOSITIONS FOR HOMOLOGOUS RECOMBINATION IN HUMAN CELLS

(75) Inventors: Niels Geijsen, West Newbury, MA (US); Christa Buecker, Somerville, MA (US)

(73) Assignee: The General Hospital Corporation, Boston, MA (US)

( * ) Notice: Subject to any disclaimer, the term of this patent is extended or adjusted under 35 U.S.C. 154(b) by 135 days.

(21) Appl. No.: 12/791,696

(22) Filed: Jun. 1, 2010

(65) Prior Publication Data

US 2010/0304489 A1 Dec. 2, 2010

Related U.S. Application Data

(60) Provisional application No. 61/182,154, filed on May 29, 2009.

(51) Int. Cl.
*C12N 15/00* (2006.01)
*C12N 5/071* (2010.01)
*C12N 5/02* (2006.01)

(52) U.S. Cl.
USPC .............................. 435/455; 435/366; 435/384

(58) Field of Classification Search
None
See application file for complete search history.

(56) References Cited

FOREIGN PATENT DOCUMENTS

WO 2009/152529 12/2009

OTHER PUBLICATIONS

Buecker, 2010, Cell Stem Cell, 6:535-546.*
Silva, PLoS Biology, 2008, 6: 2237-2247.*
Li et al 2009, Cell Stem Cell, 4:16-19.*
Evans and Kaufman, Nature, 292:154-156 (1981). "Establishment in culture of pluripotent cells from mouse embryos."
Martin, Proc Natl Acad Sci USA, 78:7634-7638 (1981). "Isolation of pluripotent cell line from early mouse embryos cultured in medium conditioned by teratocarinoma cells."

* cited by examiner

*Primary Examiner* — Valarie Bertoglio
(74) *Attorney, Agent, or Firm* — Nixon Peabody LLP; David S. Resnick; Mark J. FitzGerald

(57) ABSTRACT

The methods and compositions described herein are based, in part, on the discovery of a stem cell state in human cells that resembles the morphology observed in murine-derived stem cells. Induction of such a state in human stem cells permits an increase in the efficiency of homologous recombination. Thus, the methods and compositions described herein relate to cells and methods for increasing the efficiency of homologous recombination in human stem cells.

24 Claims, 29 Drawing Sheets

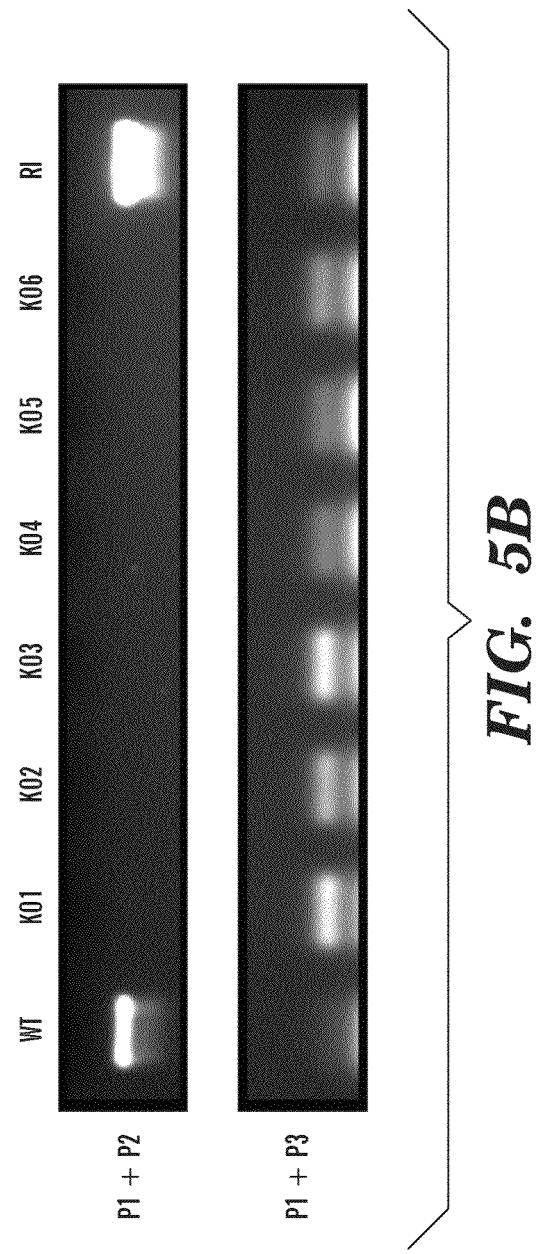

| CONDITION | % COLONIES / MILLION ELECTROPORATED CELLS |
|---|---|
| CONTROL | 0 |
| ROCK INHIBITOR | 0.61 |
| DMSO | 5.7 |
| CHIR 99021 | 8.7 |
| KENPAULLONE | 2.2 |
| SB216763 | 8.1 |

SEQUENCE LISTING

```
<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
aaagcaatcc ttctgctcca                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
taacatagca aggccccatc                                              20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gcgtcccatc ctcatttaag                                              20

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gccttttcga aggaagtgg                                               19

<210> SEQ ID NO 5
<211> LENGTH: 19
```

-continued

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
cacggcctcc caatttact                                                    19

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tggttcaaca ggaatgggat a                                                 21

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tccggcctaa aagggtaaat                                                   20

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gttggcacgt ggtgagc                                                      17

<210> SEQ ID NO 9
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
cgcgtccggc ctaaa                                                        15

<210> SEQ ID NO 10
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ggcagcgcct ccaga                                                        15

<210> SEQ ID NO 11
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 11
gtccaaagca ggatgacagg                                               20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gcaccagagt ctccgcttta                                               20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ccatccttgc tccagctatc                                               20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gccgttccaa aacttctacg                                               20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gtggacatct cttgggcact                                               20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tctgcaggag cgtacagaac                                               20
```

METHODS AND COMPOSITIONS FOR HOMOLOGOUS RECOMBINATION IN HUMAN CELLS

CROSS-REFERENCE TO RELATED APPLICATIONS

This U.S. application claims the benefit of priority under 35 U.S.C. §119(e) of U.S. Provisional Application No. 61/182,154 filed May 29, 2009, the contents of which are incorporated herein by reference in their entirety.

GOVERNMENT SUPPORT

This invention was made with Government support under Grant No. HD048769 awarded by the National Institutes of Health. The Government has certain rights in this invention.

FIELD OF THE INVENTION

The invention relates to compositions and methods involving human stem cells.

BACKGROUND

Embryonic stem cells (ES cells) were first derived in 1981 from the inner cell mass (ICM) of murine pre-implantation blastocyst embryos (Evans and Kaufman, 1981; Martin, 1981). ES cells are pluripotent, meaning they demonstrate the ability to expand indefinitely in vitro while retaining the capacity to generate ectoderm-, endoderm-, and mesoderm derivatives both in vitro and in vivo. The discovery of murine ES cells was a major breakthrough in developmental biology, since it allowed the study of mammalian gene function in vivo, through the application of transgenic and knockout technologies. The subsequent derivation of human ES cells raised the expectation that these cells would similarly revolutionize our insights into human development and disease. Unfortunately, human pluripotent stem cells have proven to be remarkably resilient to non-viral genetic manipulation and to date only a handful of human transgenic cell lines exist.

Homologous recombination in human cells, including human ES cells is remarkably inefficient. WO2009/152529 describes preliminary data regarding the targeting of two endogenous loci, OCT4 and COL1A1 by introducing sequences encoding GFP and puromycin resistance. The authors note that so far only genes that are expressed in ES cells (OCT4, HPRT, ROSA26) or that are poised to be expressed, such as MOXL1, have been targeted in human ES cells. The authors also note that the COL1A1 locus is highly recombinogenic in mouse cells, and that targeting of that locus may not be representative of other non-expressed genes. The authors state that the targeting of non-expressed genes by homologous recombination poses a challenge.

SUMMARY OF THE INVENTION

The methods and compositions described herein are based, in part, on the discovery of a stem cell state in human cells that permits an enhanced efficiency of homologous recombination. Thus, the methods and compositions described herein relate to compositions and methods that permit homologous recombination in human stem cells at an efficiency that cannot be achieved in untreated human stem cells.

In one aspect, the methods described herein relate to a composition comprising: (a) a human stem cell in an admixture with a GSK3β inhibitor, and (b) a homologous recombination cassette.

In one embodiment of this aspect and all other aspects described herein, the human stem cell in the admixture is an iPS cell, an embryonic stem cell, a stem cell line, a pluripotent stem cell, a multipotent stem cell, or an adult stem cell.

In another embodiment of this aspect and all other aspects described herein, the GSK3β inhibitor is selected from the group consisting of: CHIR99021, BIO, Kenpaullone, and SB216763.

In another embodiment of this aspect and all other aspects described herein, the human stem cell in the admixture has an enhanced efficiency of homologous recombination compared to a corresponding human stem cell not in an admixture with the GSK3β inhibitor.

In another embodiment of this aspect and all other aspects described herein, the efficiency of homologous recombination is enhanced by at least 50% compared to a corresponding human stem cell not in the admixture with the GSK3β inhibitor.

In another embodiment of this aspect and all other aspects described herein, the human stem cell in the admixture survives expansion from, or can be expanded from a single cell, whereas the corresponding human stem cell not in an admixture with the GSK3β inhibitor does not survive expansion from, or cannot expand from, a single cell.

In another embodiment of this aspect and all other aspects described herein, the human stem cell in the admixture survives passaging from a single cell by a non-collagenase digest, whereas the corresponding human stem cell not in an admixture with the GSK3β inhibitor does not survive passaging by a non-collagenase digest.

In another embodiment of this aspect and all other aspects described herein, the human stem cell in the admixture survives passaging from a single cell by trypsin digest, whereas the corresponding human stem cell not in an admixture with the GSK3β inhibitor does not survive passaging from a single cell by trypsin digest.

In another embodiment of this aspect and all other aspects described herein, the stem cell has a faster growth rate compared to the growth rate of a corresponding human stem cell not in an admixture with the GSK3β inhibitor.

In another embodiment of this aspect and all other aspects described herein, the growth rate is assessed by measuring doubling time.

In another embodiment of this aspect and all other aspects described herein, the doubling time is at least 2 hours faster than the growth rate of a corresponding human stem cell not in an admixture with the GSK3β inhibitor.

In another embodiment of this aspect and all other aspects described herein, the composition further comprises a MEK inhibitor.

In another embodiment of this aspect and all other aspects described herein, the MEK inhibitor is PD98059.

In another embodiment of this aspect and all other aspects described herein, the targeted gene is not expressed in a human embryonic stem cell.

In another embodiment of this aspect and all other aspects described herein, the targeted gene is not expressed in a human pluripotent stem cell.

In another embodiment of this aspect and all other aspects described herein, the targeted gene is not expressed in a developmentally-regulated manner.

In another embodiment of this aspect and all other aspects described herein, the targeted gene is not one of OCT4, COL1A1, HPRT, ROSA26, or MOXL1.

Also described herein, in another aspect, is a stem cell composition comprising: (a) a human stem cell clone isolated from a population of stem cells treated with a GSK3β inhibitor and having the following characteristics: (i) survives propagation from a single cell; (ii) an efficiency of homologous recombination at least 1-fold higher than the efficiency of homologous recombination in a corresponding human stem cell not treated with the GSK3β inhibitor; (iii) a doubling time at least 2 hours faster than the growth rate of a corresponding human stem cell not treated with the GSK3β inhibitor; and (iv) capable of surviving single cell passaging using trypsin digest; and (b) a homologous recombination cassette.

In one embodiment of this aspect and all other aspects described herein, the GSK3β inhibitor is selected from the group consisting of: CHIR99021, BIO, Kenpaullone, and SB216763.

In another embodiment of this aspect and all other aspects described herein, the population of stem cells is further treated with a MEK inhibitor.

In another embodiment of this aspect and all other aspects described herein, the MEK inhibitor is PD98059.

In another embodiment of this aspect and all other aspects described herein, the human stem cell is an iPS cell, an embryonic stem cell, a stem cell line, a multipotent stem cell, or an adult stem cell.

In another embodiment of this aspect and all other aspects described herein, the doubling time of the treated stem cell is 15-30 hours.

In another embodiment of this aspect and all other aspects described herein, the doubling time of the treated stem cell is 20-24 hours.

In another aspect, described herein is a method for generating a genetically-modified human stem cell, the method comprising: (a) culturing a human stem cell with a GSK3β inhibitor, and (b) modifying the genome of the stem cell in step (a) by introducing a homologous recombination cassette and inducing homologous recombination, wherein a genetically-modified human embryonic stem-like cell is generated.

In one embodiment of this aspect and all other aspects described herein, the homologous recombination event of step (b) adds a sequence, deletes a sequence, removes an exon, removes an intron, introduces a point mutation, or corrects a mutation.

In another embodiment of this aspect and all other aspects described herein, homologous recombination is induced using electroporation techniques.

In another embodiment of this aspect and all other aspects described herein, the human stem cell is an iPS cell, an embryonic stem cell, a stem cell line, a multipotent stem cell, or an adult stem cell.

In another embodiment of this aspect and all other aspects described herein, further comprises culturing the human stem cell with a MEK inhibitor.

In another embodiment of this aspect and all other aspects described herein, the MEK inhibitor is PD98059.

Also described herein is a composition comprising: (a) a human stem cell comprising at least one artificially induced or exogenously added reprogramming factor selected from the group consisting of: Oct4, Sox2, Nanog, c-MYC and KLf4, and (b) a homologous recombination cassette.

In one embodiment of this aspect and all other aspects described herein, the composition comprises each of Oct4, Sox2, Nanog, c-MYC and Klf4.

In another embodiment of this aspect and all other aspects described herein, the cell in the composition has an enhanced efficiency of homologous recombination compared to a corresponding human stem cell.

In another embodiment of this aspect and all other aspects described herein, the efficiency of homologous recombination for the cell is enhanced by at least 50% compared to a corresponding human stem cell not comprising a reprogramming factor.

In another embodiment of this aspect and all other aspects described herein, the cell of the composition survives expansion from, or expands from, a single cell, whereas the corresponding human stem cell not comprising a reprogramming factor does not survive expansion from, or expand from a single cell.

In another embodiment of this aspect and all other aspects described herein, the cell of the composition survives passaging from a single cell by a non-collagenase digest, whereas the corresponding human stem cell does not survive passaging by a non-collagenase digest.

In another embodiment of this aspect and all other aspects described herein, the cell of the composition survives passaging from a single cell by trypsin digest, whereas the corresponding human stem cell does not survive passaging by trypsin digest.

In another embodiment of this aspect and all other aspects described herein, the cell of the composition has a faster growth rate compared to the growth rate of a corresponding human stem cell not comprising a reprogramming factor.

In another embodiment of this aspect and all other aspects described herein, the growth rate is assessed by measuring doubling time.

In another embodiment of this aspect and all other aspects described herein, the doubling time is at least 2 hours faster than the growth rate of a corresponding human stem cell not in an admixture with the GSK3β inhibitor.

In another embodiment of this aspect and all other aspects described herein, the composition further comprises LIF.

Also described herein is a kit(s) for enhancing the efficiency of homologous recombination in a human stem cell, the kit comprising: (a) a GSK3b inhibitor, (b) a homologous recombination cassette, and (c) instructions and packaging therefor.

In one embodiment of this aspect and all other aspects described herein, the GSK3β inhibitor is selected from the group consisting of: CHIR99021, BIO, Kenpaullone, and SB216763.

In another embodiment of this aspect and all other aspects described herein, the kit further comprises a MEK inhibitor.

In another embodiment of this aspect and all other aspects described herein, the MEK inhibitor is PD98059.

In another embodiment of this aspect and all other aspects described herein, the kit further comprises a human stem cell.

DEFINITIONS

As used herein the term "human stem cell" refers to a human cell that can self-renew and differentiate to at least one cell type. The term "human stem cell" encompasses human stem cell lines, human-derived iPS cells, human embryonic stem cells, human pluripotent cells, human multipotent stem cells or human adult stem cells. A "pluripotent stem cell" is one that can give rise to all three germ layers, i.e., endoderm, mesoderm, and ectoderm. A "multipotent cell" is one that can differentiate to several different cell types within a restricted family, subset or lineage of cells. Examples of a multipotent stem cell include hematopoietic stem cells, adipose-derived stem cells, and tissue specific progenitor cells. As used herein, the term "adult stem cell" refers to a stem cell derived from a tissue of an organism after embryonic development is complete, i.e., a non-embryonic stem cell; such cells are also known in the art as "somatic stem cells."

As used herein, the term "enhanced efficiency of homologous recombination" refers to a given clonal cell culture having an increase of at least 50% in the number of selected colonies that have incorporated a genetic construct or transgene by homologous recombination, e.g., following transfection of a homologous recombination cassette by electroporation methods, as compared to the number of such selected colonies in a "corresponding human stem cell" culture transfected with the same homologous recombination cassette; preferably the number of colonies with successful homologous recombination in the cell culture is at least 50%, at least 75%, at least 1-fold, at least 2-fold, at least 5-fold, at least 10-fold, at least 50-fold, at least 100-fold, at least 200-fold, at least 300-fold, at least 400-fold, at least 500-fold, at least 1000-fold or more greater than the number of colonies with successful homologous recombination in a culture of corresponding human stem cells.

As used herein, the term "corresponding human stem cell" refers to a human stem cell in culture that serves as a reference or control for the measurement of one or more properties of a human stem cell manipulated according to the methods described herein. In a preferred aspect, a corresponding human stem cell is taken from the same human stem cell population prior to treatment or manipulation to modify homologous recombination efficiency. Where, for example, a human iPS cell is used for manipulation, the corresponding human stem cell is an iPS cell, preferably from the same population of iPS cells that are manipulated. Thus, a corresponding human stem cell culture will be cultured under substantially similar conditions to the cells being tested. Where the corresponding human stem cell population is used to compare the efficiency of homologous recombination of a human stem cell or embryonic stem cell-like cell, the corresponding human stem cell population will be transfected using the same methods of transfection to which the stem cell population being tested has been exposed. Alternatively, where the corresponding human stem cell population is used as a control population to compare growth rate, doubling time, ability to be passaged from a single cell, morphology, and ability to be passaged using trypsin digest of a human stem cell or embryonic stem cell-like cell, the corresponding human stem cell population is not treated with e.g., a GSK3β inhibitor as described herein.

As used herein, the terms "not developmentally regulated" or "not developmentally expressed" refers to a gene that is not differentially regulated during development, that is, the gene is not expressed at a different extent (e.g., at least 10% different (increased or decreased), at least 20% different, at least 30% different, at least 40% different, at least 50% different, at least 60% different, at least 70% different, at least 80% different, at least 90% different, at least 100% different, at least 2-fold higher, at least 5-fold higher, at least 10-fold higher, at least 25-fold higher, at least 50-fold higher, at least 100-fold higher, at least 100-fold higher, or more) in a cell from an embryo or developing fetus relative to an adult somatic cell.

As used herein, the phrases "survives expansion from a single cell" or "expands from a single cell" refer to the ability of a cell to be isolated to a single cell level, which in turn is capable of growth and division to generate a clonal cell culture. The term preferably refers to the ability to repeatedly expand such cells from single cells.

As used herein, the term "survives passaging by a non-collagenase digest" refers to the ability of a single cell to survive passaging from a parent culture to a sub-culture using enzymatic digestion with an agent other than collagenase.

As used herein, the term "survives passaging by trypsin digest" refers to the ability of a single cell to be passaged from a parent culture to a sub-culture using enzymatic digestion with trypsin. Typically, human stem cells do not survive single cell passaging with a trypsin digestion and require rather collagenase digestion or mechanical disruption to permit passaging to a sub-culture. However, murine cells and the human stem cell compositions described herein are capable of surviving single cell passaging using trypsin enzymatic digestion. Other non-collagenase based passage methods that can provide single-cell suspensions include, for example, dissociation induced by chelating calcium and/or magnesium, for example using EDTA or other chelators.

As used here the term "faster growth rate" refers to a decrease in the doubling time of a cell composition described herein of at least 2 hours (h) compared to the doubling time of a corresponding human stem cell cultured in substantially similar growth conditions. In some embodiments, it is preferred that the doubling time of the cell described herein is at least 3 hours less, at least 4 hours less, at least 5 hours less, at least 6 hours less, at least 7 hours less, at least 8 hours less, at least 9 hours less, at least 10 hours less, at least 11 hour less, at least 12 hours less, at least 13 hours less, at least 14 hours less, at least 15 hours less, at least 16 hours less, at least 17 hours less, at least 18 hours less, at least 19 hours less, at least 20 hours less, at least 21 hour less, at least 22 hours less, at least 23 hours less, at least 24 hours less, or more compared to the doubling time of a corresponding human stem cell cultured under substantially similar conditions. In one embodiment, the doubling time is about 15-30 hours. In another embodiment, the doubling time is about 20-24 hours.

As used herein, the term "morphology" is used to describe one or more characteristics regarding the physical appearance of a cell that distinguishes it from or renders it similar to a given cell type or state. While morphology may not be absolutely connected to permissiveness for homologous recombination, Applicants have recognized that morphology of a human stem cell more like a murine ES cell correlates with the permissiveness for homologous recombination.

The term "stem cell phenotype," as used herein, refers to functional and/or physical characteristics of a stem cell, including one or more of marker expression, doubling time, ability to be passaged by trypsin digest, among others. A mouse or murine stem cell phenotype refers to a cell with a doubling time of approximately 12-18 hours (e.g., 16 hours), which can be passaged by trypsin digest and can be propagated from a single cell, and has a high efficiency of homologous recombination compared to a corresponding human stem cell. A murine or mouse stem cell phenotype can also generally be LIF-dependent, and can also express mouse-like markers, e.g., SSEA1. As used herein, the term "human stem cell or stem cell-like phenotype" refers to a cell having a doubling time of approximately 35-40 h (e.g., 37 hours), which is unable to be passaged by trypsin digest, cannot be propagated from a single cell and typically expresses human pattern stem cell surface markers such as SSEA3, SSEA4, or TRA-1-81.

As used herein the term "expresses SSEA1" refers to a cell from which SSEA1 protein levels are detectable using standard methods such as ELISA, Western Blotting, fluorescence labeling, in situ hybridization, immunocytochemistry etc. Conversely, the term "does not express SSEA3, SSEA4 or TRA-1-81" refers to a cell that does not have detectable protein levels of SSEA3, SSEA4, or TRA-1-81 using standard methods such as those listed above.

As used herein, the term "human embryonic stem-like cell" refers to a human cell capable of stem cell renewal and which can differentiate to substantially the same number of cell types as an isolated and untreated human embryonic stem cell, but that has been treated or cultured to permit a change in morphology or phenotype (e.g., to a murine stem cell-like morphology or phenotype) and enhanced efficiency of homologous recombination.

"Homologous recombination" (HR) or "legitimate recombination," as the term is used herein, refers to the exchange of DNA sequences between two DNA molecules, mainly two homologous chromosomes that involves loci with complete or far-reaching base sequence identity. Homologous recombination may also occur between a chromosome or other cellular DNA and an extra-chromosomal element introduced into the cell, provided that the extracellular element carries a region with complete or nearly complete sequence complementarity.

As used herein, the term "reprogramming factor" refers to a protein or other molecule, such as small molecule, that promotes or contributes to cell reprogramming to an induced pluripotent stem cell phenotype, e.g., in vitro. A reprogramming factor is added exogenously or ectopically to the cell, e.g., by direct introduction of a protein or small molecule; or by expressing the factor from a vector or heterologous construct introduced to the cell, or otherwise introducing nucleic acid encoding the factor. The reprogramming factor is preferably, but not necessarily, from the same species as the cell being reprogrammed, i.e., human reprogramming factors for human cells. Non-limiting examples of reprogramming factors of interest for reprogramming somatic cells to pluripotency in vitro are Oct4, Nanog, Sox2, Lin28, Klf4, c-Myc, and any gene/protein or molecule that can substitute for one or more of these in a method of reprogramming somatic cells in vitro. "Reprogramming to a pluripotent state in vitro" is used herein to refer to in vitro reprogramming methods that do not require and typically do not include nuclear or cytoplasmic transfer or cell fusion, e.g., with oocytes, embryos, germ cells, or pluripotent cells.

As used herein, the term "homologous recombination cassette" is a linear DNA molecule designed to undergo homologous recombination with a targeted region of genomic, chromosomal DNA in a cell. Such a cassette includes, at a minimum, a linear DNA molecule including first and second lengths of targeting DNA (also referred to as "arms"), separated by a selection cassette containing a gene encoding a selection marker or selectable marker. The targeting DNA arms each include a length of genomic DNA homologous to a region on the targeted chromosome adjacent to a targeted region on the chromosome, such that one arm is homologous to genomic sequence on one side of the targeted region of the chromosome, and the other arm is homologous to genomic sequence on the other side of the targeted region of the chromosome. In this manner, the regions of homology to the targeted chromosome in the respective targeting arms flank the targeted region of the chromosome. The lengths of the targeting DNA arms can vary as discussed herein below in the section regarding homologous recombination. In addition to the selection cassette, the homologous recombination cassette can also include, between the first and second arms, sequence encoding one or more additional desired genetic elements (a therapeutic or other gene, an miRNA, etc.). The selection cassette permits the identification of cells that have incorporated the exogenous DNA. In some embodiments there can be further markers on the homologous recombination cassette that permit the distinction between cells that have randomly incorporated the cassette and cells that have incorporated it in a targeted manner by homologous recombination. However, the ordinarily skilled artisan can determine whether a cell has incorporated the cassette by homologous recombination, e.g., via Southern blot or other approaches known in the art.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

BRIEF DESCRIPTION OF THE FIGURES

FIGS. 5A-5C: Homologous recombination mediated gene targeting in hLR5 cells. 5A Schematic representation of the human HPRT locus and the targeting construct containing a puromycin selection cassette. The PCR primers used to detect the wild-type locus and the targeting construct (P1, P2, P3) are indicated; 5B PCR detection of 6 independent clones in which the HPRT locus was successfully targeted (KO1-6) and one clone with random integration of the targeting construct (RI). Wild-type cells (WT) were used as control. Upper panel, presence of the wild-type allele in WT cells (left lane) and cells with random integration of the targeting construct (RI, right lane). Lower panel, detection of the targeting construct in the Knockout clones (KO1-6) and cells with random integration of the targeting construct (RI); 5C Confirmation of functional knockout of the HPRT gene in targeted hLR5 cells. WT: Wild-type, KO1 and KO2: knockout clones; RI: Clone with random integration, 6-TG: 6-thioguanine which kills wild-type cells and cells with random integration of the targeting construct, HAT: HAT supplement, which kills cells lacking functional HPRT expression only.

DETAILED DESCRIPTION

Figure 1A:
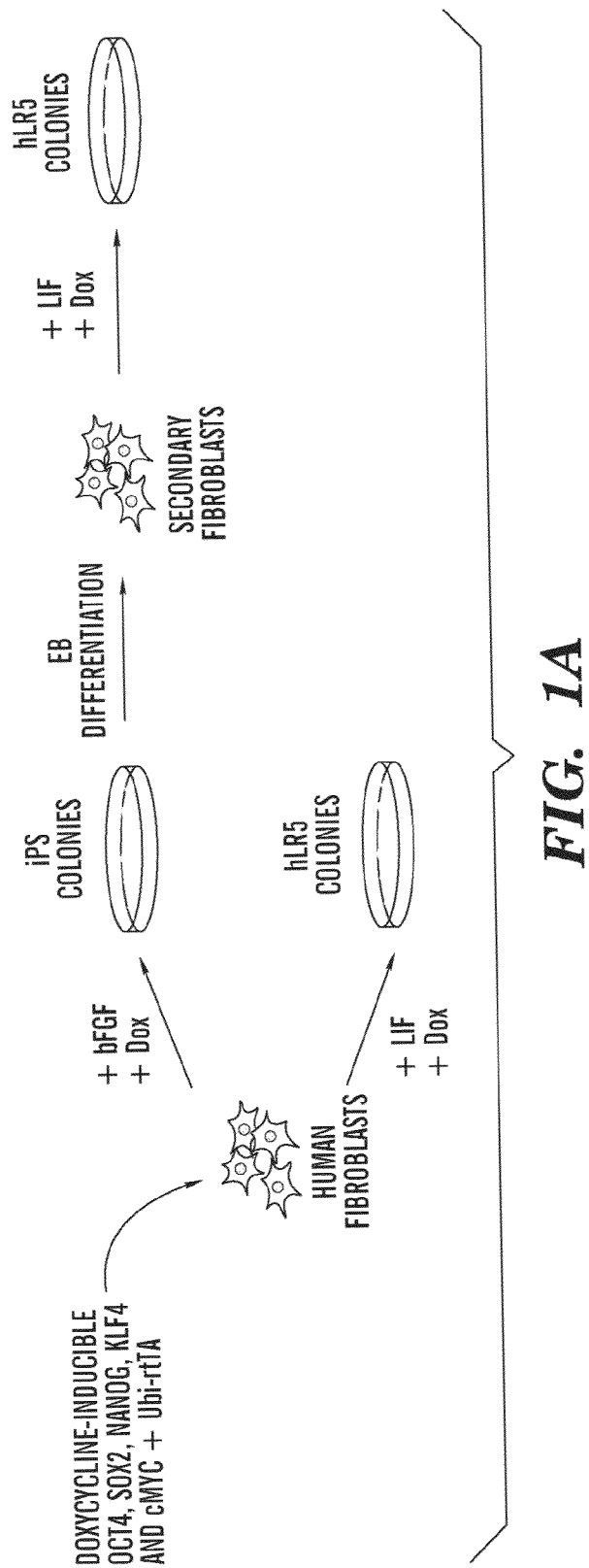
FIGS. 1A-1D: A metastable human iPS state with murine ES cell properties. 1A Schematic representation of the strategy used for the reprogramming of human fibroblasts into factor-dependent human iPS cells. Doxycycline-inducible lentiviral vectors were added either as individual vectors (Maherali et al., 2008) or the polycystronic human STEMCCA virus (Sommer et al., 2009) and inducible NANOG as indicated in the text; 1B Colony morphology of hLR5 cells (left panel), murine ES cells (middle panel) and human ES cells; 1C FACS analysis of cell surface marker expression on hLR5 cells, murine ES cells and human iPS cells. Black lines: Cell surface marker expression using the indicated primary antibody. Light line: no primary antibody control; 1D Growth curve of hLR5 cells, mES and hES over a period of 12 days. Cumulative cell number is plotted against days (n=3, SD).

The methods and compositions described herein are based, in part, on the discovery of a stem cell state in human cells that resembles the morphology observed in murine-derived stem cells. Induction of such a state in human stem cells permits an increase in the efficiency of homologous recombination. Thus, the methods and compositions described herein relate to cells and methods for increasing the efficiency of homologous recombination in human stem cells.

In one aspect, the efficiency of homologous recombination in human stem cells can be increased by treating human stem cells, e.g., human embryonic stem cells or human iPS cells with a GSK3β inhibitor. Such treatment, optionally in conjunction with additional agents, e.g., a MEK inhibitor, induces human stem cells, including human embryonic stem cells and human iPS cells, to increase their rates of cell proliferation, and to survive single cell expansion, using non-collagenase based agents, such as trypsin-mediated single cell passaging. Human stem cells that have reached this state are much more permissive for homologous recombination than similar or corresponding human stem cells that have not been treated in this manner and do not show the phenotypic properties of increased growth rate and survival following single-cell expansion and passage, e.g., with trypsin.

In another aspect, the permissiveness of human iPS cells for homologous recombination is increased when the cells are induced by expression of five reprogramming factors (Oct4, Sox2, Klf4, c-Myc and Nanog) and in the presence of LIF.

The methods and considerations for achieving the state of permissiveness for homologous recombination in human stem cells, and for using those cells to generate genetically altered human stem cell populations that can then be differentiated to various cell types are discussed in the following sections.

Stem Cells

Stem cells are undifferentiated cells defined by their ability at the single cell level to both self-renew and differentiate to produce progeny cells, including self-renewing progenitors, non-renewing progenitors, and terminally differentiated cells. Stem cells, depending on their level of differentiation, are also characterized by their ability to differentiate in vitro into functional cells of various cell lineages from multiple germ layers (endoderm, mesoderm and ectoderm), as well as to give rise to tissues of multiple germ layers following transplantation and to contribute substantially to most, if not all, tissues following injection into blastocysts.

Stem cells are classified by their developmental potential as: (1) totipotent, which is able to give rise to all embryonic and extraembryonic cell types; (2) pluripotent, which is able to give rise to all embryonic cell types. i.e., endoderm, mesoderm, and ectoderm; (3) multipotent, which is able to give rise to a subset of cell lineages, but all within a particular tissue, organ, or physiological system (for example, hematopoietic stem cells (HSC) can produce progeny that include HSC (self-renewal), blood cell restricted oligopotent progenitors and the cell types and elements (e.g., platelets) that are normal components of the blood); (4) oligopotent, which is able to give rise to a more restricted subset of cell lineages than multipotent stem cells; and (5) unipotent, which is able to give rise to a single cell lineage (e.g., spermatogenic stem cells).

Stem cells of interest for producing cells with enhanced efficiency of homologous recombination or a murine stem cell-like morphology include embryonic cells of various types, exemplified by human embryonic stem (hES) cells, described by Thomson et al. (1998) Science 282:1145; U.S. Pat. No. 7,615,374; U.S. Pat. No. 7,611,852; U.S. Pat. No. 7,582,479; U.S. Pat. No. 7,514,260; U.S. Pat. No. 7,439,064, U.S. Pat. No. 7,390,657; U.S. Pat. No. 7,220,584; U.S. Pat. No. 7,217,569; U.S. Pat. No. 7,148,062; U.S. Pat. No. 7,029,913; U.S. Pat. No. 6,887,706; U.S. Pat. No. 6,613,568; U.S. Pat. No. 6,602,711; U.S. Pat. No. 6,280,718; U.S. Pat. No. 6,200,806; and U.S. Pat. No. 5,843,780, each of which is herein incorporated in their entirety by reference; and human embryonic germ (hEG) cells (Shambloft et al., Proc. Natl. Acad. Sci. USA 95:13726, 1998). Also of interest are lineage committed stem cells, such as hematopoietic or pancreatic stem cells. Examples of multipotent cells useful in methods provided herein include, but are not limited to, human umbilical vein endothelial (HuVEC) cells, human umbilical artery smooth muscle (HuASMC) cells, human differentiated stem (HKB-II) cells, and human mesenchymal stem (hMSC) cells.

Adult stem cells are generally limited to differentiating into different cell types of their tissue of origin. However, if the starting stem cells are derived from the inner cell mass of the embryo, they can give rise to all cell types of the body derived from the three embryonic germ layers: endoderm, mesoderm and ectoderm. Stem cells with this property are said to be pluripotent. Embryonic stem cells are one kind of pluripotent stem cell. Somatic stem cells have major advantages, for example, using somatic stem cells allows a patient's own cells to be expanded in culture and then re-introduced into the patient. Of course, induced pluripotent stem cells (iPS cells) from a patient provide a source of cells that can be expanded and re-introduced to the patient, before or after stimulation to differentiate to a desired lineage of phenotype.

Cells derived from embryonic sources can include embryonic stem cells or stem cell lines obtained from a stem cell bank or other recognized depository institution. Other means of producing stem cell lines include the method of Chung et al (2006) which comprises taking a blastomere cell from an early stage embryo prior to formation of the blastocyst (at around the 8-cell stage). The technique corresponds to the pre-implantation genetic diagnosis technique routinely practiced in assisted reproduction clinics. The single blastomere cell is then co-cultured with established ES-cell lines and then separated from them to form fully competent ES cell lines.

Embryonic stem cells are considered to be undifferentiated when they have not committed to a specific differentiation lineage. Such cells display morphological characteristics that distinguish them from differentiated cells of embryo or adult origin. Undifferentiated embryonic stem (ES) cells are easily recognized by those skilled in the art, and typically appear in the two dimensions of a microscopic view in colonies of cells with high nuclear/cytoplasmic ratios and prominent nucleoli.

In one embodiment, the stem cell is isolated. Most conventional methods to isolate a particular stem cell of interest involve positive and negative selection using markers of interest. Agents can be used to recognize stem cell markers, for instance labeled antibodies that recognize and bind to cell-surface markers or antigens on desired stem cells. Antibodies or similar agents specific for a given marker, or set of markers, can be used to separate and isolate the desired stem cells using fluorescent activated cell sorting (FACS), panning methods, magnetic particle selection, particle sorter selection and other methods known to persons skilled in the art, including density separation (Xu et al. (2002) Circ. Res. 91:501; U.S. patent application Ser. No. 20030022367) and separation based on other physical properties (Doevendans et al. (2000) J. Mol. Cell. Cardiol. 32:839-851). Alternatively, genetic selection methods can be used, where a stem cell can be genetically engineered to express a reporter protein operatively linked to a tissue-specific promoter and/or a specific gene promoter; therefore the expression of the reporter can be used for positive selection methods to isolate and enrich the desired stem cell. For example, a fluorescent reporter protein can be expressed in the desired stem cell by genetic engineering methods to operatively link the marker protein to a promoter active in a desired stem cell (Klug et al. (1996) J. Clin. Invest. 98:216-224; U.S. Pat. No. 6,737,054). Other means of positive selection include drug selection, for instance as described by Klug et al., supra, involving enrichment of desired cells by density gradient centrifugation. Negative selection can be performed, selecting and removing cells with undesired markers or characteristics, for example fibroblast markers, epithelial cell markers etc.

Undifferentiated ES cells express genes that can be used as markers to detect the presence of undifferentiated cells. The polypeptide products of such genes can be used as markers for negative selection. For example, see U.S. application Ser. No. 2003/0224411 A1; Bhattacharya (2004) Blood 103(8):2956-64; and Thomson (1998), supra., each herein incorporated by reference. Human ES cell lines express cell surface markers that characterize undifferentiated nonhuman primate ES and human EC cells, including stage-specific embryonic antigen (SSEA)-3, SSEA-4, TRA-1-60, TRA-1-81, and alkaline phosphatase. The globo-series glycolipid GL7, which carries the SSEA-4 epitope, is formed by the addition of sialic acid to the globo-series glycolipid Gb5, which carries the SSEA-3 epitope. Thus, GL7 reacts with antibodies to both SSEA-3 and SSEA-4. Undifferentiated human ES cell lines do not stain for SSEA-1, but differentiated cells stain strongly for SSEA-1. Methods for proliferating hES cells in the undifferentiated form are described in WO 99/20741, WO 01/51616, and WO 03/020920, which are herein incorporated by reference in their entirety.

In one embodiment, the methods provide for enrichment and isolation of stem cells. The stem cells are selected for a characteristic of interest. In some embodiments, a wide range of markers may be used for selection. One of skill in the art will be able to select markers appropriate for the desired cell type. The characteristics of interest include expression of particular markers of interest, for example specific subpopulations of stem cells and stem cell progenitors will express specific markers.

In one embodiment, the stem cells are expanded. The cells are optionally collected, separated, and further expanded, generating larger populations of stem cells for use in making cells of a particular cell type or cells having an enhanced efficiency of homologous recombination.

Induced Pluripotent Stem Cells (iPS Cells)

While still only several years old, the technology for iPS cell generation has become relatively standard practice. The production of iPS cells is generally achieved by the introduction of nucleic acid sequences encoding stem cell-associated genes into an adult, somatic cell. Historically, these nucleic acids have been introduced using viral vectors and the expression of the gene products results in cells that are morphologically, biochemically, and functionally similar to pluripotent stem cells (e.g., embryonic stem cells). This process of altering a cell phenotype from a somatic cell phenotype to a pluripotent stem cell phenotype is termed "reprogramming." iPS cells can be generated or derived from terminally differentiated somatic cells, as well as from adult stem cells. That is, a non-pluripotent stem cell can be rendered pluripotent by reprogramming. In such instances, it may not be necessary to include as many reprogramming factors as required to reprogram a terminally differentiated cell. Further, reprogramming can be induced by the non-viral introduction of reprogramming factors, e.g., by introducing the proteins themselves, or by introducing nucleic acids that encode the reprogramming factors. Reprogramming can be achieved by introducing a combination of stem cell-associated genes including, for example Oct-4 (also known as Oct-3/4 or Pouf51), Sox1, Sox2, Sox3, Sox 15, Sox 18, NANOG, Klf1, Klf2, Klf4, Klf5, NR5A2, c-Myc, 1-Myc, n-Myc, Rem2, Ten, and LIN28. In one embodiment, successful reprogramming is accomplished by introducing Oct-4, a member of the Sox family, a member of the Klf family, and a member of the Myc family to a somatic cell. In one embodiment each of Oct 4, Sox2, Nanog, c-MYC and Klf4 are used to reprogram a human stem cell.

The efficiency of reprogramming (i.e., the number of reprogrammed cells) derived from a population of starting cells can also be enhanced by the addition of various small molecules as shown by Shi, Y., et al (2008) Cell-Stem Cell 2:525-528, Huangfu, D., et al (2008) Nature Biotechnology 26(7):795-797, and Marson, A., et al (2008) Cell-Stem Cell 3:132-135, which are incorporated herein by reference in their entirety. It is contemplated that the methods described herein can also be used in combination with a single small molecule (or a combination of small molecules) that enhances the efficiency of induced pluripotent stem cell production or that replaces one or more reprogramming factors during the reprogramming process. Some non-limiting examples of agents that enhance reprogramming efficiency include soluble Wnt, Wnt conditioned media, BIX-01294 (a G9a histone methyltransferase), PD0325901 (a MEK inhibitor), DNA methyltransferase inhibitors, histone deacetylase (HDAC) inhibitors, valproic acid, 5'-azacytidine, dexamethasone, suberoylanilide, hydroxamic acid (SAHA), and trichostatin (TSA), among others.

To confirm the induction of pluripotent stem cells, isolated clones can be tested for the expression of a stem cell marker. Such expression identifies the cells as induced pluripotent stem cells. Stem cell markers can be selected from the non-limiting group including SSEA3, SSEA4, CD9, Nanog, Fbx15, Ecat1, Esg1, Eras, Gdf3, Fgf4, Cripto, Dax1, Zpf296, Slc2a3, Rex1, Utf1, and Nat1. Methods for detecting the expression of such markers can include, for example, RT-PCR and immunological methods that detect the presence of the encoded polypeptides. In one embodiment, detection does not involve RT-PCR, but rather focuses on detection of protein markers.

The pluripotent stem cell character of the isolated cells can be confirmed by any of a number of tests evaluating the expression of ES markers and the ability to differentiate to cells of each of the three germ layers. As one example, teratoma formation in nude mice can be used to evaluate the pluripotent character of the isolated clones. The cells are introduced to nude mice and histology and/or immunohistochemistry is performed on a tumor arising from the cells. The growth of a tumor comprising cells from all three germ layers further indicates that the cells are pluripotent stem cells.

Small Molecule Modulators

Small molecule modulators are described herein for increasing the capacity of human stem cell to undergo or perform homologous recombination, e.g., activators of WNT signaling, such as GSK3β inhibitors; MEK inhibitors; or other target molecules. Generally, the human stem cell is incubated in the presence of or contacted with the small molecule(s) until the cell shows a mouse-like ES cell morphology or characteristics discussed elsewhere herein. As used herein, the term "small molecule" refers to a chemical agent including, but not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. Small molecule modulators, such as inhibitors of e.g., GSK3β activity, can be identified from within a small molecule library, which can be obtained from commercial sources such as AMRI (Albany, N.Y.), AsisChem. Inc. (Cambridge, Mass.), TimTec (Newark, Del.), among others, or from libraries as known in the art.

In one embodiment, the small molecule is an activator of the WNT signaling pathway, including, but not limited to, an inhibitor of GSK3β activity, such as CHIR99021, BIO, Kenpaullone or SB216763. In other embodiments, a MEK inhibitor (e.g., PD98059) is also included in the culture medium. It is contemplated herein that a small molecule modulator (e.g., a GSK3β inhibitor) can be used alone or in combination with other modulators e.g., activators of WNT signaling, inhibitors of MEK activity, PKA activity, PKC activity etc. In one embodiment, the modulator is not a small molecule but a polypeptide, such as a WNT polypeptide, fusion protein, or signaling fragment thereof.

Example concentration ranges for small molecule inhibitors (e.g., a GSK3β inhibitor) to be added e.g., to cell culture media and/or for the treatment of the human stem cells include, but are not limited to, about 1 nanomolar to about 10 millimolar; about 1 mM to about 5 mM; about 1 nM to about 500 nM; about 500 nM to about 1,000 nM; about 1 nM to about 1,000 nM; about 1 μM to about 1,000 μM; 1 μM to about 500 μM; about 1 μM to about 100 μM; about 1 μM to about 50 μM; about 1 μM to about 15 μM; about 1 μM to about 10 μM; about 1 μM to about 5 μM; about 1 μM to about 3 μM; about 0.5 μM to about 2 μM; about 2 μM to about 20 μM, or about 5 μM to about 10 μM. In one embodiment, the range is about 5 μM to about 500 μM. The concentration will of course vary with the identity of the given inhibitor, or various inhibitors, have greater or lesser inhibitory activities. In one embodiment, 0.1 μM of a small molecule inhibitor is cultured with the cell. In another embodiment, 0.5 μM of a small molecule inhibitor is cultured with the cell. In another embodiment, 1 μM of a small molecule inhibitor is cultured with the cell. In another embodiment, 3 μM of a small molecule inhibitor is cultured with the cell. In another embodiment, 5 μM of an inhibitor is cultured with the cell. In another embodiment, 10 μM of an inhibitor is cultured with the cell. In another embodiment, 15 μM of an inhibitor is cultured with the cell. In another embodiment, 25 μM of an inhibitor is cultured with the cell. In another embodiment, 50 μM of an inhibitor is cultured with the cell. In other embodiments the following concentration ranges can be used: about 0.1 μM to about 1 μM, about 0.5 μM to about 1 μM, about 1 μM to about 5 μM, about 5 μM to about 10 μM; about 1 μM to about 10 μM; about 10 μM to about 500 μM; about 10 μM to about 100 μM; about 500 nM to about 10 μM; about 500 nM to about 1 μM; about 0.01 μM to about 1 μM; 0.1 μM to about 1 μM; about 1 μM to about 2 μM; about 1 μM to about 5 μM; about 1 μM to about 3 μM; about 3 μM to about 5 μM; about 5 μM to about 7 μM; 0.01 μM to about; about 10 μM to about 20 μM; or about 1 nM to about 1 μM.

Cells can be treated for various times. Suitable times can be determined by those of skill in the art by monitoring stem cell morphology (becomes more like mouse-like, as discussed below, e.g., appearance of dome shaped or egg shaped cells), or other phenotypic characteristics, including but not limited to, increase in the growth rate (e.g., decrease in doubling time), ability to expand from a single cell, and ability to be passaged by trypsin digest. For example, cells can be treated for minutes, 15 minutes, 30 minutes etc, or more often, treated for hours or days, e.g., 1 hour, 2 hours, 3 hours, 4 hours, up to 24 hours, days (e.g., 1 day, 2 days, 3 days, 4 days, 5, days 6 days, 7 days), or even weeks (e.g., 2 weeks, 3 weeks, 4 weeks, 5 weeks, 6 weeks, 7 weeks, 8 weeks, 9 weeks, 10 weeks, 11 weeks, 12 weeks or more). The duration of treatment will be that treatment necessary to achieve at least, the ability to expand from a single cell and decreased doubling time and the ability to be passaged via trypsin digest.

Human Vs. Murine Stem Cell Morphology

While both human and murine ES cells are derived from blastocyst-stage embryos, they demonstrate profound differences in colony morphology, proliferation rate, growth factor requirements and epigenetic status (Thomson et al., 1998). Murine ES cells grow in three-dimensional, tightly packed colonies with a population doubling time of approximately 16 hours, and the maintenance of murine ES cells is dependent on LIF and BMP4 growth factor signaling (Smith et al., 1988; Xu et al., 2005; Ying et al., 2003). In contrast, human ES cells form flattened two-dimensional colonies and are maintained in a bFGF and Activin A/TGFbeta signaling-dependent manner (Thomson et al., 1998). Human ES cells proliferate slowly, with a population doubling time averaging 36 hours. Epigenetically, human and murine ES cells display a different X-chromosome inactivation pattern and promoter occupancy by pluripotency transcription factors (Boyer et al., 2005; Silva et al., 2008; Tesar et al., 2007). In addition, human ES cells are passaged as small clumps of cells by mechanical- or collagenase methods, and unlike murine ES cells, human ES cell lines cannot be passaged as single cells by trypsin digest. The inability of human ES cell lines to grow from single cells greatly impedes genetic modification of these cells, since the introduction of transgenes is typically followed by clonal selection through antibiotic treatment or flow cytometry-based technologies.

Two reports on the derivation of murine epiblast stem cells (EpiSCs) recently provided a new perspective on the nature of human ES cells (Brons et al., 2007; Tesar et al., 2007). EpiSCs are derived from post-implantation murine epiblast embryos under culture conditions that are very similar to human ES cell culture conditions. EpiSCs display many of the molecular, morphological and functional characteristics of human ES cells including their dependence on bFGF/Activin A signaling, their flattened colony morphology, their slower proliferation rate compared to murine ES cells, their X-inactivation status and their requirement to be passaged as small clumps of cells rather than by trypsin digest (Brons et al., 2007; Tesar et al., 2007).

The culture dynamics and the specific morphological, molecular and functional characteristics of murine ES cells and EpiSCs appear to be largely determined by the growth factor conditions under which these cell types are derived and maintained. Intriguingly, while pluripotent stem cells can be stably derived and propagated from multiple species in an epiblast-like state, including the rat and "non-permissive" mouse strains, the LIF-dependent pluripotent state appears to be unstable in these species. (Buehr et al., 2008; Hanna et al., 2009; Li et al., 2009; Liao et al., 2009). However, in these non-permissive species, the LIF-dependent pluripotent state can be stabilized through the constitutive ectopic expression of one or more of the reprogramming factors (Oct4, Sox2, Klf4, cMyc), which have recently been shown to allow the generation of induced pluripotent stem cells (iPS cells) from somatic cells (Takahashi et al., 2007; Takahashi and Yamanaka, 2006). In the non-permissive NOD mouse strain, the constitutive ectopic expression of either Klf4 or cMyc is sufficient to allow the derivation of ES-like cells from blastocyst embryos (Hanna et al., 2009). Similarly, rat iPS cells require the constitutive ectopic expression of Oct4, Sox2, Klf4 and cMyc to stabilize their LIF-dependent pluripotent state (Liao et al., 2009). Small molecule inhibitors of glycogen synthase kinase 3 beta (GSK3β) and the mitogen-activated protein kinase (MAPK) signaling pathway can replace some of the reprogramming factors during iPS cell generation (Huangfu et al., 2008a; Huangfu et al., 2008b; Shi et al., 2008). These inhibitors can similarly stabilize the LIF-dependent pluripotent state in blastocyst-derived stem cells or in iPS cells from both the non-permissive NOD mouse strain and the rat (Buehr et al., 2008; Hanna et al., 2009; Li et al., 2009; Liao et al., 2009). Thus, it appears that the LIF-dependent pluripotent state is metastable in these species, meaning it is dependent on either the constitutive expression of ectopic reprogramming factors or the continued inhibition of GSK3β and/or the MAPK signaling pathways.

Assessing Morphology of a Cell or Cell Culture

One of skill in the art can assess the morphology of a cell by measuring characteristics of the cell, such as doubling time, ability to be passaged by trypsin digest, ability to be propagated from a single cell, efficiency of homologous recombination, expression level of a cell surface marker etc.

To determine doubling time, one can simply count the number of cells at two or more timepoints (e.g., using Trypan Blue staining) and optionally plot the relationship between number of cells and time on a graph. The slope of the linear portion of the graph can be used to determine the doubling time of a cell culture during the active growth phase. Other methods for determining doubling time are known in the art and can be used with the methods and cells described herein.

Functional aspects of cell phenotype, such as the ability of a cell to be passaged by trypsin digest and the ability to be propagated from a single cell, can be easily determined by one of skill in the art using routine cell culture methods known in the art.

The efficiency of homologous recombination can be measured, for example, by assessing the number of colonies derived from a human stem cell composition (e.g., the cell compositions described in the Example section herein) having successful delivery of a transgene by homologous recombination compared to the number of such colonies in a culture of isolated human embryonic stem cells, which are known to have low rates of homologous recombination. A homologous recombination event in a cell can be measured by the ability of the cell to grow in the presence of a selection reagent such as 6-thioguanine or can be assessed directly using a positive selection reagent such as GFP. Such methods are described further herein in the "Homologous Recombination" section of the Detailed Description.

The phenotype of a cell composition as described herein can also be assessed by measuring the expression level of a cell surface marker such as SSEA1, SSEA3, SSEA4 or TRA-1-81. Methods for detecting the expression of such markers can include, for example, RT-PCR and immunological methods that detect the presence of the encoded polypeptides.

Homologous Recombination

Homologous recombination provides a successful approach to achieve targeted, as opposed to random, delivery of a genetic construct or genetic insert into the genome of human stem cells (e.g., ES cells, or iPS cells). Methods for performing homologous recombination often involve the use of electroporation to introduce the genetic construct or insert into the ES cell. Homologous recombination facilitates introduction of the genetic construct or insert into a desired target location in the genome of the ES cells. The desired target location can be an intronic or exonic sequence of a gene, or it can any target sequence of the genome, such as a promoter sequence, enhancer sequence, or microRNA sequence. Homologous recombination events offer a distinct advantage over random gene insertions in that the site of the insertion of foreign or exogenous DNA can be controlled, thus avoiding unwanted gene insertion and permitting targeted manipulation of native or endogenous genes. Known methods for genetically altering cells that use homologous recombination can be used to insert, delete, modify, or rearrange DNA sequences in the genome of a human stem cell, provided the cell is treated as described herein to stimulate or enhance its ability to perform homologous recombination. One of skill in the art can design and prepare a genetic insert or construct intended to express an output product, such as a gene product or a microRNA, in e.g., ES cells, or a genetic insert which is not intended to produce an output gene product. If it is desired to produce a cell line in which a selected native gene in the ES cell line is silenced or disrupted, this can be done by making a "knock-out" genetic construct. For this purpose, the delivered genetic insert can be, in essence, no DNA at all, but the knock-out insertion is preferably a DNA sequence which simply does not encode an output or gene product at all.

If the genetic insert is intended to produce a gene product, the genetic insert should be a construction capable of expressing a gene product in an ES cell. This alternative is sometimes referred to here as the "knock-in" approach, by which a genetic insert, producing a gene product, is substituted for a genetic sequence previously in the cells. The gene product would typically be a protein, but the production of other gene products such as RNAs (including microRNAs, interfering RNAs and antisense RNAs) is also contemplated. To produce an output product, such as a gene product, the genetic insert would typically be an expression cassette including, in sequence, a promoter, a coding sequence for the gene product and a transcriptional terminator sequence, all selected to be effective in the ES cells and appropriate for the overall process being performed.

In knock-out cells, the functioning of a particular targeted native gene is disrupted or suppressed in the genome of those cells, and such cells can be used in order to study the effect that the lack of expression of that gene has on the viability, health, development, differentiation, or other characteristics of the ES cells and their progeny. This is done by replacing the native genetic sequence by homologous recombination with a genetic sequence that does not express the same protein or nucleic acid as the sequence replaced. Knock-out stem cell cultures of murine stem cells can be grown into so-called "knock-out mice" which have been very influential in the identification of gene function information for many genes in mice. Knock-out ES cell lines can be used to identify genes responsible for the undifferentiated status of ES cells, as well as to identify and study the function of those genes which activate the differentiation process. Knock-out cells can be useful for drug testing and screening studies as well, as described herein.

The knock-in alternative also offers a powerful way to study both gene expression and the differentiation process, as well as offering the ability to create cultures of differentiated cells directly from primary ES cells, for a variety of purposes, including drug and small molecule screening assays, and therapeutic applications. To do this, preferably the expression cassette in the genetic insert includes a promoter which drives the expression of a screenable marker gene or selectable marker gene coding sequence which is positioned downstream of a promoter, or operably linked to a promoter sequence, in a genetic construct. The promoter is, for example, a tissue specific promoter that only drives expression of the screenable or selectable marker if the ES cell or progeny thereof into which the expression cassette has been transformed has then later differentiated into a selected cell lineage. For example, if the promoter is specific to cardiomyocytes, or heart cells, the promoter would become active to drive its associated gene expression only in those ES derived cells which have differentiated into cardiomyocytes. If the gene driven by the tissue specific promoter is a selectable marker, it can be used to select for cells which have undergone the desired differentiation. An alternative strategy is to make gene expression constructs or inserts without promoters of any kind, and then to introduce the insert into the genome of ES cells in a site where the genetic insert will only be expressed by native promoter activity specific to a desired state's lineage or state of differentiation. This promoter activity would be chosen to be a promoter which is active only when the cells are in a desired differentiation lineage. Again, a screenable marker or selectable marker gene coding sequence is useful to distinguish the cells which have achieved the selected state of differentiation from other cells in culture. A screenable marker gene would be a gene the expression of which can be observed in a living cell, such as the green fluorescent protein (GFP) or luciferase, but which cannot be used to kill non-transformed cells. A screenable marker gene is used to identify transformed cells expressing the marker through visible cell selection techniques, such as fluorescent cell sorting techniques. A selectable marker would be a gene that confers resistance to a selection agent, such as an antibiotic, which is lethal to cells not having the selectable marker. A selectable marker is used in conjunction with a selection agent to select in culture for cells expressing the inserted gene construct.

One of skill in the art can use the hypoxanthine phosphoribosyltransferase gene (HPRT) as a target to test the efficiency of homologous recombination in a cell. The HPRT gene is located on the X chromosome and a single homologous recombination event disrupting this gene leads to complete loss of function in XY cells. In humans, mutations of this gene are found in patients having Lesch-Nyhan syndrome, a neurological disorder. Cells which are deficient in HPRT activity can be selected based on their resistance to 6-thioguanine (also referred to as 2-amino, 6 mercaptopurine) (6-TG) (Sigma cat. No. A4660), and thus the frequency of homologous recombination events can be directly measured.

The targeting genetic constructs, or homologous recombination cassettes for the compositions and methods described herein generally comprise two sequences having homology to sequences flanking the 5' and 3' ends of a target sequence, and which usually flank a positive selectable marker, such as the gene encoding neomycin phosphotransferase. A negative selectable maker is often located external but adjacent to one of the regions of homology to provide for enrichment of correctly targeted cells in the total population through elimination of cells containing the negative selectable cassette. Introduction of a replacement vector into cells followed by simultaneous or stepwise positive and negative selection results in the isolation of cells which have perhaps an eight to twelve-fold enriched probability of undergoing site-specific homologous recombination due to application of the negative selectable marker.

Alternative positive selection strategies have been designed which do not include the utilization of positive-negative selection. These include the application of strategies for the conditional expression of a dominant selectable marker by virtue of in-frame gene fusion with the target gene. For example, utilizing the resistance marker neomycin phosphotransferase Sedivy et al. demonstrated successful gene targeting of the polyoma middle T antigen (pmt) locus (Sedivy et al. (1989), Proc. Natl. Acad. Sci., 86, 227).

In addition, the gene to be expressed can be operably linked to any of a wide variety of different types of transcriptional regulatory sequences that regulate expression of the gene in the cell. For example, the gene can be under control of a promoter that is constitutively active in many different cell types, or one that is developmentally regulated and is only active in one or a few specific cell types. Alternatively, the gene can be operably linked to an inducible promoter that can be activated by exposure of the cell to a physical (e.g., cold, heat, light, radiation) or a chemical signal. Many such inducible promoters and methods for using them effectively are well known. Examples of the characteristics and use of such promoters, and of other well-known transcriptional regulatory elements such as enhancers, insulators, and repressors, are described, for example, in Transgenic Animals, Generation and Use, 1997, edited by L. M. Houdebine, Hardwood Academic Publishers, Australia, the contents of which are incorporated herein by reference.

Homologous Recombination Using Targeting Genetic Constructs

The simplest targeting genetic construct, homologous recombination cassette, or genetic insert, for use in the compositions and methods described herein consists of 2 segments of genomic DNA (gDNA) called "homology arms", flanking a sequence encoding a selection marker or gene, i.e., a selection cassette. The two segments of genomic DNA have homology to sequences flanking the sequence being targeted in a cell, such as a human stem cell, e.g., an ES cell, iPS cell, or other human stem cell.

In some embodiments, the selection cassette comprises the cDNA encoding the selection gene, and control elements, such as promoters, enhancers, and internal ribosomal entry sites. In other embodiments, a promoterless selection gene is used. A selection gene can be any gene by which a cell having undergone successful homologous recombination is selected, such as a resistance gene or a reporter gene. Exemplary resistance genes for use in the selection cassettes described herein include a neomycin (G418) resistance gene, and other resistance genes such as puromycin, hygromycin, and 6-thioguanine. Exemplary reporter genes include fluorescent or luminescent reporter genes, such as EGFP.

When introduced into embryonic stem (ES) cells, the gDNA homology arms will undergo recombination with their matching or homologous sequences on one chromosome, and the sequence of the selection cassette will be introduced into the ES cell genome along with them. The gDNA between the regions of homology on the chromosome is thereby replaced by the selection cassette and any other intervening sequences flanked by the homology arms of the targeting genetic construct or insert. Where a complete knockout or removal of the sequence in a target cell, such as an ES cell, is desired, the intervening sequence is usually positioned or designed to replace the TATA box, the start codon, and one or more of the initial exons.

The degree to which the homology arms match the same sequences in the endogenous genomic locus of interest in the cell being targeted will help determine the frequency and precision of homologous recombination. Three important characteristics of homology arms for successful homologous recombination include: (i) length, (ii) sequence homology, and (iii) limited repetitive sequences.

In one embodiment, the homology arms have an overall length of about 7 kilobases, with one arm being 5-6 kb and the other being 1-2 kb. Typically, a longer homology arm will have a higher degree of success in homologous recombination, but one is usually limited by the capacity of the cloning vector and the need to maintain a unique restriction enzyme site that can be used to linearize the construct prior to transfection into ES cells. With regard to sequence homology, the homology arms can be cloned from the genome of the ES cells that will be targeted, or from the subject (e.g., human) they were derived from. Long-range PCR with a high-fidelity polymerase is an effective method for subcloning the homology arms. In one embodiment, the homology arms lack substantial repetitive sequences. One of skill in the art can use e.g., on-line programs such as RepeatMasker, to search for repetitive sequences in the homology arms. Large regions of repetitive DNA should be avoided, as these will result in a lower frequency of homologous recombination. In some embodiments, the sequences for use in the homologous arms can be cloned from a library of sequences from the same species as the cell being targeted. For example, libraries of bacterial artificial chromosomes (BACs) can be used as a source of the sequences for use in the homology arms of the targeting genetic constructs used in the methods and compositions provided herein.

A targeting genetic construct can also integrate into random loci, by non-homologous recombination mechanisms. Any such non-homologous integration event, random or specific, can confer drug resistance to a cell into which such a targeting genetic construct has been introduced. After growing the transfected cells under selection, typically the challenge is to screen enough clones to find the rare homologous recombination events in a background of frequent random integrants. However, the methods and compositions described herein permit enhanced efficiency of homologous recombination.

Screening of clones can be achieved through the use of both positive and negative selection cassettes in all genetic targeting constructs. A commonly used negative selection cassette comprises the gene for thymidine kinase, or tk. The tk gene product allows growing cells to incorporate a toxic nucleotide analog into their DNA, thus selecting against those cells. The tk cassette is cloned into the targeting construct outside of the homology arms, so that it will not be incorporated during homologous recombination. However, it will be incorporated if a targeting genetic construct undergoes non-homologous recombination or random integration, and can thus be used to select against those clones that have undergone random integration, and not undergone homologous recombination. Another negatively selectable marker that can be used in the constructs described herein is the gene for diphtheria toxin A. The A subunit inhibits protein synthesis but cannot be taken up by other cells. Its advantage over tk is that it works without having to add a second drug to a culture medium.

Accordingly, a targeting genetic construct or homologous recombination cassette comprising a 5' region homologous to at least a portion of the chromosomal region in which homologous recombination is desired, and a 3' region homologous to at least a portion of the chromosomal region in which homologous recombination can be designed for introduction into a cell. The lengths of the 5' region and the 3' region may be any lengths which permit homologous recombination to occur. The recombination also contains an insertion sequence located between the 5' region and the 3' region. The insertion sequence is a sequence which is desired to be introduced into the genome of the cell.

For example, in some embodiments, the insertion sequence may comprise a gene which is desired to be introduced into the genome of the cell. In some embodiments, the gene may be operably linked to a promoter in the recombination vector. Alternatively, in other embodiments, the gene may become operably linked to a promoter in the adjacent chromosomal region after homologous recombination has occurred. In some embodiments the gene may be a gene from the same organism as the cells in which it is to be introduced. For example, the gene may be a wild type gene which rescues a genetic defect in the cell after it is introduced through homologous recombination.

In other embodiments, the gene may be from a different organism than the cell into which it is to be introduced. For example, the gene may encode a therapeutically beneficial protein from an organism other than the organism from which the cell was obtained. In some embodiments, for example, the gene may encode a therapeutically beneficial human protein such as a growth factor, hormone, or tumor suppressor.

In some embodiments, the insertion sequence introduces a point mutation into an endogenous chromosomal gene after homologous recombination has occurred. The point mutation may disrupt the endogenous chromosomal gene or, alternatively, the point mutation may enhance or restore its activity.

In other embodiments, the insertion sequence introduces a deletion into an endogenous chromosomal gene after homologous recombination has occurred. In such embodiments, the insertion sequence may "knock out" the target gene.

In some embodiments, it may be desired to replace, disrupt, or knock-out both chromosomal copies of the target gene or to introduce two copies of a desired nucleotide sequence into the genome of a cell. In such embodiments, two homologous recombination procedures are performed as described herein to introduce the desired nucleotide sequence into both copies of the chromosomal target sequence. Alternatively, a genetically modified organism in which one copy of the chromosomal target sequence has been modified as desired may be generated using the methods described herein. Subsequently, cells may be obtained from the genetically modified organism and subjected to a second homologous recombination procedure as described herein. The cells from the second homologous recombination procedure may then be used to generate an organism in which both chromosomal copies of the target sequence have been modified as desired.

In some embodiments, the insertion sequence or a portion thereof may be located between two sites, such as loxP sites, which allow the insertion sequence or a portion thereof to be deleted from the genome of the cell at a desired time. In embodiments in which the insertion sequence or a portion thereof is located between loxP sites, the insertion sequence or portion thereof may be removed from the genome of the cell by providing the Cre protein. Cre may be provided in the cells in which a homologous recombination event has occurred by introducing Cre into the cells through lipofection (Baubonis et al., 1993, Nucleic Acids Res. 21:2025-9, the disclosure of which is incorporated herein by reference in its entirety), or by transfecting the cells with a vector comprising an inducible promoter operably linked to a nucleic acid encoding Cre (Gu et al., 1994, Science 265:103-106; the disclosure of which is incorporated herein by reference in its entirety).

In some embodiments, additional sequences can be added to flank the selection cassettes to enable removal of these sequences following successful homologous recombination. For example, a positive selection cassette of a genetic targeting insert can further comprise recombinase recognition sequences (RSS) flanking the sequence encoding the selection gene, such as a resistance gene, like Neo, or a reporter gene, like GFP. Expression or introduction, in those cells that have undergone homologous recombination, of a recombinase that recognizes the RSSs allows the selection gene sequence to be removed. Exemplary recombinase and RSSs combinations that can be used in the methods and compositions provided herein include, but are not limited to, Cre/loxP and Flp/FRT.

Zinc-Finger Endonucleases (ZFE)

In some embodiments, homologous recombination can further comprise the use of zinc finger endonucleases. For example, in one embodiment, a GSK3β inhibitor can be combined with homologous recombination achieved using a zinc finger endonuclease to cleave an endogenous chromosomal nucleotide sequence at or near a site at which it is desired to introduce a nucleic acid by homologous recombination. Such zinc finger endonucleases are described in e.g., US Patent Application 2009/0305402, which is herein incorporated by reference in its entirety. The ZFE comprises a zinc finger domain which binds near the endogenous nucleotide sequence to be cleaved and an endonuclease domain which cleaves the endogenous chromosomal nucleotide sequence. Cleavage of the endogenous chromosomal nucleotide sequence increases the frequency of homologous recombination at or near that nucleotide sequence.

Essentially any suitable endonuclease domain can be used to cleave the endogenous chromosomal nucleotide sequence. The endonuclease domain is fused to the heterologous DNA binding domain (such as a zinc finger DNA binding domain) such that the endonuclease will cleave the endogenous chromosomal DNA at the desired nucleotide sequence. In some embodiments the endonuclease domain can be the HO endonuclease or a Fok I endonuclease. One of skill in the art will appreciate that any other endonuclease domain that is capable of working with heterologous DNA binding domains, preferably with zinc finger DNA binding domains, can be used.

The HO endonuclease domain from *Saccharomyces cerevisiae* is encoded by a 753 by Pst I-Bgl II fragment of the HO endonuclease cDNA available on Pubmed (Acc # X90957, the disclosure of which is incorporated herein by reference in its entirety). The HO endonuclease cuts both strands of DNA (Nahon et al., "Targeting a truncated Ho-endonuclease of yeast to novel DNA sites with foreign zinc fingers," Nucleic Acids Res. 26 (5):1233-1239 (1998); the disclosure of which is incorporated herein by reference in its entirety). *Saccharomyces cerevisiae* genes rarely contain any introns, so, if desired, the HO gene can be cloned directly from genomic DNA prepared by standard methods. For example, if desired, the HO endonuclease domain can be cloned using standard PCR methods.

In some embodiments, the Fok I (*Flavobacterium okeanokoites*) endonuclease can be fused to a heterologous DNA binding domain. The Fok I endonuclease domain functions independently of the DNA binding domain and cuts a double stranded DNA only as a dimer (the monomer does not cut DNA) (Li et al., "Functional domains in Fok I restriction endonuclease," Proc. Natl. Acad. Sci. U.S.A 89 (10):4275-4279 (1992), and Kim et al., "Hybrid restriction enzymes: zinc finger fusions to Fok I cleavage domain," Proc. Natl. Acad. Sci. U.S.A 93 (3):1156-1160 (1996); the disclosures of which are incorporated herein by reference in their entireties). Therefore, in order to create double stranded DNA breaks, two ZFEs are positioned so that the Fok I domains they contain dimerize. The Fok I endonuclease domain can be cloned by PCR from the genomic DNA of the marine bacteria *Flavobacterium okeanokoites* (ATCC) prepared by standard methods. The sequence of the Fok I endonuclease is available on Pubmed (Acc # M28828 and Acc #J04623, the disclosures of which are incorporated herein by reference in their entireties).

ZFE include a zinc finger domain with specific binding affinity for a desired target sequence in the human stem cell genome. For example, the nucleic acid region may be a region which contains a gene in which it is desired to introduce a mutation, such as a point mutation or deletion, or a region into which it is desired to introduce a gene conferring a desired phenotype.

There are a large number of naturally occurring zinc finger DNA binding proteins which contain zinc finger domains that can be incorporated into a ZFE designed to bind to a specific endogenous chromosomal sequence. Each individual "zinc finger" in the ZFE recognizes a stretch of three consecutive nucleic acid base pairs. The ZFE can have a variable number of zinc fingers. For example, ZFEs with between one and six zinc fingers can be designed. In other examples, more than six fingers can be used. A two finger protein has a recognition sequence of six base pairs, a three finger protein has a recognition sequence of nine base pairs and so on. Therefore, the ZFEs used herein can be designed to recognize any desired endogenous chromosomal target sequence, thereby avoiding the necessity of introducing a cleavage site recognized by the endonuclease into the genome through genetic engineering.

In preferred embodiments, the ZFE protein can be designed and/or constructed to recognize a site which is present only once in the genome of a cell being targeted for homologous recombination. For example, one ZFE protein can be designed and made with at least five zinc fingers. Also, more than one ZFE protein can be designed and made so that collectively the ZFEs have five zinc fingers (i.e. a ZFE having two zinc fingers can complex with a ZFE having 3 zinc fingers to yield a complex with five zinc fingers). Five is used here only as an exemplary number. Any other number of fingers can be used. Five zinc fingers, either individually or in combination, have a recognition sequence of at least fifteen base pairs. Statistically, a ZFE with 5 fingers will cut the genome about once every $1 \times 10^9$ base pairs, which will be less than once per average size genome. In more preferred embodiments, an individual protein or a combination of proteins with six zinc fingers can be used. Such proteins have a recognition sequence of 18 bp.

It will be appreciated that the zinc fingers in the ZFEs used with the methods and compositions described herein can be any combination of zinc fingers which recognize the desired binding site. The zinc fingers can come from the same protein or from any combination of heterologous proteins which yields the desired binding site.

To generate a ZFE, a nucleotide sequence encoding a ZFE with the desired number of fingers fused to the desired endonuclease is cloned into a desired expression vector. There are a number of commercially available expression vectors into which the nucleotide sequence encoding the ZFE can be cloned. The expression vector is then introduced into a cell capable of producing an active ZFE. For example, the expression vector can be introduced into a bacterial cell, a yeast cell, an insect cell or a mammalian cell. Preferably, the cell lacks the binding site recognized by the ZFE. Alternatively, the cell can contain the binding site recognized by the ZFE but the site can be protected from cleavage by the endonuclease through the action of cellular enzymes.

In other embodiments, the ZFE can be expressed or produced in a cell free system such as TNT Reticulocyte Lysate. The produced ZFE can be purified by any appropriate method. In preferred embodiments, the ZFE also includes a purification tag which facilitates purification of the ZFE. For example, the purification tag can be the maltose binding protein, myc epitope, a poly-histidine tag, HA tag, FLAG-tag, GST-tag, or other tags familiar to those skilled in the art. In other embodiments, the purification tag can be a peptide which is recognized by an antibody which can be linked to a solid support such as a chromatography column.

The ZFE produced as described herein can be purified using conventional techniques such as a chromatography column containing moieties thereon which bind to the purification tag. The purified ZFE is then quantified and the desired amount of ZFE is introduced into the cells in which it is desired to enhance the frequency of homologous recombination. The ZFE can be introduced into the cells using any desired technique, such as electroporation.

Alternatively, rather than purifying the ZFE and introducing it into the cells in which it is desired to enhance the frequency of homologous recombination, the ZFE can be expressed directly in the cells. In such embodiments, an additional expression vector containing a nucleotide sequence encoding the ZFE operably linked to a promoter is introduced into the cells. The promoter can be a constitutive promoter or a regulated promoter. The expression vector can be a transient expression vector or a vector which integrates into the genome of the cells.

Additional Embodiments for Promoting Homologous Recombination

In other embodiments of the compositions and methods described herein, additional methods are provided to promote or enhance homologous recombination in an ES or other human stem cell being targeted with a targeting genetic construct or homologous recombination cassette.

In some embodiments, modified electroporation methods can be used, as described in Zwaka, T. P. and Thomson, J. A. (2003) "Homologous recombination in human embryonic stem cells." Nat. Biotechnol. 21, 319-321. In such embodiments, modifying the electroporation method can include, without limitation, modifying electroporation parameters (such as voltage and capacitance), modifying the media used during electroporation (such as placing cells in isotonic, protein-rich solution), and performing electroporation at room temperature.

In some embodiments, a recombinase-mediated cassette-exchange method is used for homologous recombination, as described in Irion, S. et al. (2007) "Identification and targeting of the ROSA26 locus in human embryonic stem cells. Nat. Biotechnol. 25, 1477-1482."

In some embodiments, helper-dependent adenoviral vectors can be used to further enhance homologous recombination. Unlike retroviruses and lentiviruses, adenoviruses do not integrate into the human genome. Helper-dependent adenoviral vectors have a lower cytotoxicity and elicit a smaller host immune response than standard E1-deleted adenoviral vectors because the gene transfer cassette contains only the packaging signal sequence and lacks all viral genes, which have been completely removed from the vector genome. The virus system produces virus particles containing the foreign gene to be introduced via homlogous recombination when the helper adenovirus is excised. Advantages of using helper adenoviral systems for introducing foreign genes into cells include their low cytotoxicity, which makes it possible to use them at higher multiplicities of infection, and their expanded cloning capacity permits the insertion of larger homology arms for homologous recombination. Using helper dependent adenoviral vector systems can also improve the targeted-to-random integration ratio, as compared to non-viral electroporation methods (Suzuki, K. et al. (2008) "Highly efficient transient gene expression and gene targeting in primate embryonic stem cells with helper-dependent adenoviral vectors." Proc. Natl. Acad. Sci. U.S.A. 105, 13781-13786 and M. Nakayama, 2010, "Homologous recombination in human iPS and ES cells for use in gene correction Therapy." Drug Discovery Today, Vol. 15, Numbers 5/6).

Drug and Small Molecule Screening

The methods and compositions described herein can also be used for the development of high-throughput screening technologies of disease model systems and assays for the identification and characterization of compounds for use in the treatment of human disease. Characterization of drug compounds includes aspects such as compound development, identifying cell-specific toxicity and cell-specific survival, and assessments of compound safety, compound efficacy, and dose-response parameters.

The drug discovery process is time-consuming and costly, in part owing to the high rate of attrition of compounds in clinical trials. Thus, modifications and alternative platforms that could accelerate the advancement of promising drug candidates, or reduce the likelihood of failure, would be extremely valuable. High-throughput screening technologies refer to the platforms and assays used to rapidly test thousands of compounds. For example, reporter systems used in cell lines can be used to assess whether compounds activate particular signaling pathways of interest.

Embryonic stem cell and induced pluripotent stem cell technologies provide a source of normal human cells that can be expanded to quantities necessary for drug screening and toxicology studies. These cells can be differentiated to generate specific cell types (for example, neurons, blood cells and cardiac muscle), and iPSCs can now be derived from patients with specific diseases. Advantages of ES cells for use in screening platforms is that from a single and potentially limitless starting source, most of the major cells within the human body that could be affected by a drug can be produced. Such cells would provide a better predictive model of both drug efficacy and toxicity than rodent cell lines or immortalized human cell lines that are currently used in high-throughput screens. While immortalized cell and animal models have contributed a wealth of information about the complexity of various disease processes, compounds that show a significant benefit in such models can fail to show effectiveness in clinical trials. For example, use of a transgenic mouse that over-expresses mutant superoxide dismutase (SOD), a gene found to be associated with amyotrophic lateral sclerosis, enabled the identification of several compounds that alter disease characteristics, including vitamin E and creatine. However, when these compounds were tested in humans, no clinical improvements were observed (A. D. Ebert and C. N. Svendsen, "Human stem cells and drug screening: opportunities and challenges." 2010 Nature Reviews Drug Discovery 9, p. 1-6). Furthermore, toxic effects of compounds are often missed in cell and animal models due to specific interactions with human biological processes that cannot be recapitulated in these systems.

Accordingly, in some aspects, the compositions comprising the genetically modified human stem cells, and the methods described herein, can be used for evaluating the effects of novel compounds on specific human cell types that are relevant to drug toxicity effects. In some embodiments, the genetically modified human stem cells can be induced to undergo differentiation to a tissue that the test drug or compound affects, and then used for performing dose-response toxicity studies. In such embodiments, genetically modified human stem cells, such as iPS cells, derived from patients can be exposed to appropriate differentiation factors and instructed to form the various cell types found in the human body, which could then be useful for assessing multiple cellular characteristics upon exposure to a compound or compounds of interest. For example, the cells could be used to assess the effects of drug candidates on functional cardiomyocytes, or on cardiomyocytes having a specific genetic mutation, because drug development is often stalled by adverse cardiac effects. Thus, measurable disruption of electrophysiological properties by known and novel compounds can be assessed in a clinically relevant, consistent and renewable cell source. Also, for example, such cells can be used to identify metabolic biomarkers in neural tissues derived from human stem cells after toxin exposure. Such embodiments allow potentially toxic compounds to be eliminated at an early stage of the drug discovery process, allowing efforts to be directed to more promising candidates.

In other aspects, the compositions comprising the genetically modified human stem cells, and the methods described herein, are used in differentiation screens, i.e., for identifying compounds that increase self-renewal or differentiation, promote maturation, or enhance cell survival from human ES or iPS cells.

In other aspects, the compositions comprising the genetically modified human stem cells, and the methods described herein, can be used to screen for drugs that may correct an observed disease phenotype. In such aspects, the cells can be expanded, differentiated into the desired cell type, and then used to screen for drugs that may correct the observed disease phenotype.

In some embodiments of these aspects, induced disease progression can be modeled using the genetically modified human stem cells, or via chemical toxicity. For example, Parkinson's disease primarily affects the dopaminergic neurons in the substantia nigra. Approximately 5% of Parkinson's disease cases have been shown to have mutations in various genes, including α-synuclein (SNCA), PARKIN (also known as PARK2) and DJ1 (also known as PARK7), causing early onset of disease symptoms. Using the genetically modified human stem cells provided as described herein, overexpression of mutated synuclein can be studied, by differentiating the cells to dopamine neurons, and then used to screen for drugs that may interact with this process, or reduce the accumulation of synuclein within cells. Also, environmental toxins (for example, rotenone, paraquot or 1-methyl-4-phenyl-1,2,3,6-tetrahydropyridine) that are known to lead to the specific loss of dopamine neurons in humans and primates, can be added to these cells to examine the molecular processes involved in dopaminergic cell loss, and ways to prevent it. Similar models of neurodegeneration for Alzheimer's disease using overexpression of pathogenic amyloid protein and cortical neurons, or amyotrophic lateral sclerosis, using mutant SOD1 protein and motor neurons could be generated using the genetically modified human stem cells described herein.

In some aspects, the compositions comprising genetically modified human stem cells described herein are particularly advantageous for investigating diseases that have defined genetic causation.

For example, spinal muscular atrophy and familial dysautonomia, have shown disease-specific phenotypes in in cell culture assays iPS cells derived from patients. Spinal muscular atrophy is caused by a specific mutation in the survival of motor neuron 1 (SMN1) gene, which leads to the death of motor neurons in the spinal cord and paralysis (Coovert; D. D. et al. "The survival motor neuron protein in spinal muscular atrophy. Hum. Mol. Genet. 6, 1205-1214 (1997), and Lefebvre, S. et al. Identification and characterization of a spinal muscular atrophy-determining gene. Cell 80, 155-165 (1995)). Humans, but not mice, have a telomeric duplication of the gene (SMN2), which, due to a single nucleotide transition and exon splicing alteration, only makes 10% of the normal SmN protein, in children carrying only two copies of SMN2. Such mutations can be recapitulated in genetically modified human stem cells, using the methods and compositions described herein, and such cells can be used to screen and identify compounds that can increase the production of the SmN2 protein.

Similarly, familial dysautonomia is a developmental peripheral neuropathy caused by a point mutation in the inhibitor of κ-light polypeptide gene enhancer in B-cells, kinase complex-associated protein (IKBKAP) gene leading to loss of autonomic and sensory neurons. This point mutation can be introduced into a human ES cell, using the methods and compositions described herein, and the genetically modified human stem cell and its progeny can be used in screening methods for drug compounds that impact neurogenesis.

Other diseases having known genetic causation that can be recapitulated using the genetically modified stem cells described herein for screening of drug compounds i include, but are not limited to, thalassaemia, sickle cell anemia, haemophilia, cystic fibrosis, Tay sachs disease, fragile X syndrome, Huntington's disease, Marfan syndrome (caused by mutations in fibrillin 1 (FBN1)), phenylketonuria (caused by mutations in phenylalanine hydroxylase (PAH)), Fabry disease, persistent hyperinsulinaemic hypoglycaemia of infancy (PHHI), familial hypercholesterolaemia, Hyperalphalipoproteinaemia (CETP), Tangier disease (ABCA1), Hypo- and hypercholesterolaemia (PCSK9), Erythermalgia (SCN9A; also known as NAV1.7), Familial exudative vitreoretinopathy (FZD4, LRP5, NDP), 1p36 deletion syndrome, 18p deletion syndrome, 21-hydroxylase deficiency, Turner syndrome, Down syndrome, triple X syndrome, Klinefelter's syndrome, ALA dehydratase deficiency, Cri du chat, ataxia telangiectasia, alpha 1-antitrypsin deficiency, congenital absence of the vas deferens, aceruloplasminemia, achondrogenesis type II, achondroplasia, Achondrogenesis type II, achondroplasia, Gaucher disease type 1, Apert syndrome, acrocephalosyndactyly, Pfeiffer syndrome, Gaucher disease type 2, acute intermittent porphyria, Canavan disease, Alzheimer's disease, Muenke syndrome, familial adenomatous polyposis, adenylosuccinate lyase deficiency, Adrenoleukodystrophy, acute intermittent porphyria, androgen insensitivity syndrome, alkaptonuria, Alexander disease, alpha 1-antitrypsin deficiency, amyotrophic lateral sclerosis, Alström syndrome, Amelogenesis imperfecta, Canavan disease, X-linked Angelman syndrome, Beare-Stevenson cutis gyrata syndrome, Benjamin syndrome, beta-thalassemia, biotimidase deficiency, bladder cancer, Bloom syndrome, breast cancer, Birt-Hogg-Dubé syndrome, CADASIL syndrome, CGD Chronic granulomatous disorder, Campomelic dysplasia, Celiac Disease, Charcot-Marie-Tooth disease, Cockayne syndrome, Coffin-Lowry syndrome, collagenopathy, types II and XI, Congenital erythropoietic porphyria, Congenital heart disease, Congenital hypothyroidis, Connective tissue disease, Cowden syndrome, Crohn's disease, Crouzon syndrome, Crouzonodermoskeletal syndrome, de Grouchy syndrome, Di George's syndrome, distal spinal muscular atrophy, type V, Ehlers-Danlos syndrome, erythropoietic protoporphyria, factor V Leiden thrombophilia, familial adenomatous polyposis, familial dysautonomia, FG syndrome, fragile X syndrome, Friedreich's ataxia, G6PD deficiency, galactosemia, Gaucher disease, Harlequin type ichthyosis, hemochromatosis, hemophilia, hepatoerythropoietic porphyria, Hereditary coproporphyria, Hereditary multiple exostoses, Hereditary nonpolyposis colorectal cancer, homocystinuria, hyperoxaluria, primary, hyperphenylalaninemia, hypochondrogenesis, hypochondroplasia, Incontinentia pigmenti P, infantile-onset ascending hereditary spastic paralysis, Jackson-Weiss syndrome, Joubert syndrome, Kniest dysplasia, Krabbe disease, Lesch-Nyhan syndrome, Li-Fraumeni syndrome, lipoprotein lipase deficiency, Marfan syndrome, McCune-Albright syndrome, McLeod syndrome, MEDNIK, Mediterranean fever familial, Menkes disease, Methemoglobinemia#beta-globin type, methylmalonic academia, Microcephaly, Mowat-Wilson syndrome, Mucopolysaccharidosis (MPS I), Muscular dystrophy, Duchenne and Becker type, myotonic dystrophy, Neurofibromatosis type I, Neurofibromatosis type II, nonsyndromic deafness, Noonan syndrome, osteogenesis imperfecta, otospondylomegaepiphyseal dysplasia, pantothenate kinase-associated neurodegeneration, Patau Syndrome (Trisomy 13), Pendred syndrome, Peutz-Jeghers syndrome, Pfeiffer syndrome, phenylketonuria, porphyria, Prader-Willi syndrome, primary pulmonary hypertension, prion disease, propionic academia, protein C deficiency, protein S deficiency, pseudo-Gaucher disease, pseudoxanthoma elasticum, Retinoblastoma, Rett syndrome, Rubinstein-Taybi syndrome, SADDAN, sickle cell anemia, Siderius X-linked mental retardation syndrome, Smith-Lemli-Opitz syndrome, spinal-bulbar muscular atrophy, spinal muscular atrophy, spinocerebellar ataxia, spondyloepimetaphyseal dysplasia, Strudwick type, spondyloepiphyseal dysplasia congenital, Stickler syndrome, tetrahydrobiopterin deficiency, thanatophoric dysplasia, thiamine-responsive megaloblastic anemia with diabetes mellitus and sensorineural deafness, thyroid disease, Treacher Collins syndrome, tuberous sclerosis, Usher syndrome, variegate porphyria, von Hippel-Lindau disease, Waardenburg syndrome, Weissenbacher-Zweymüller syndrome, Williams Syndrome, Wilson disease, Wolf-Hirschhorn syndrome, Xeroderma pigmentosum, X-linked severe combined immunodeficiency, and X-linked sideroblastic anemia.

Treatment of Disease

In one aspect, the genetically modified human stem cells described herein can be produced from an ex vivo stem cell isolated from a subject having a genetic disease. The genetic modification is intended to correct the genetic defect, and can be used to treat the disease by administering genetically modified human stem cells to permit e.g., repopulation of somatic cells (e.g., bone marrow transplant).

A wide range of diseases are recognized as being treatable with stem cell therapies. As non-limiting examples, these include disease marked by a failure of naturally occurring stem cells, such as aplastic anemia, Fanconi anemia, and paroxysmal nocturnal hemoglobinuria (PNH). Others include, for example: acute leukemias, including acute lymphoblastic leukemia (ALL), acute myelogenous leukemia (AML), acute biphenotypic leukemia and acute undifferentiated leukemia; chronic leukemias, including chronic myelogenous leukemia (CML), chronic lymphocytic leukemia (CLL), juvenile chronic myelogenous leukemia (JCML) and juvenile myelomonocytic leukemia (JMML); myeloproliferative disorders, including acute myelofibrosis, angiogenic myeloid metaplasia (myelofibrosis), polycythemia vera and essential thrombocythemia; lysosomal storage diseases, including mucopolysaccharidoses (MPS), Hurler's syndrome (MPS-IH), Scheie syndrome (MPS-IS), Hunter's syndrome (MPS-II), Sanfilippo syndrome (MPS-III), Morquio syndrome (MPS-IV), Maroteaux-Lamy Syndrome (MPS-VI), Sly syndrome, beta-glucuronidase deficiency (MPS-VII), adrenoleukodystrophy, mucolipidosis II (I-cell Disease), Krabbe disease, Gaucher's disease, Niemann-Pick disease, Wolman disease and metachromatic leukodystrophy; histiocytic disorders, including familial erythrophagocytic lymphohistiocytosis, histiocytosis-X and hemophagocytosis; phagocyte disorders, including Chediak-Higashi syndrome, chronic granulomatous disease, neutrophil actin deficiency and reticular dysgenesis; inherited platelet abnormalities, including amegakaryocytosis/congenital thrombocytopenia; plasma cell disorders, including multiple myeloma, plasma cell leukemia, and Waldenstrom's macroglobulinemia. Other malignancies treatable with stem cell therapies include but are not limited to breast cancer, Ewing sarcoma, neuroblastoma and renal cell carcinoma, among others. Also treatable with stem cell therapy are: lung disorders, including COPD and bronchial asthma; congenital immune disorders, including ataxia-telangiectasia, Kostmann syndrome, leukocyte adhesion deficiency, DiGeorge syndrome, bare lymphocyte syndrome, Omenn's syndrome, severe combined immunodeficiency (SCID), SCID with adenosine deaminase deficiency, absence of T & B cells SCID, absence of T cells, normal B cell SCID, common variable immunodeficiency and X-linked lymphoproliferative disorder; other inherited disorders, including Lesch-Nyhan syndrome, cartilage-hair hypoplasia, Glanzmann thrombasthenia, and osteopetrosis; neurological conditions, including acute and chronic stroke, traumatic brain injury, cerebral palsy, multiple sclerosis, amyotrophic lateral sclerosis and epilepsy; cardiac conditions, including atherosclerosis, congestive heart failure and myocardial infarction; metabolic disorders, including diabetes; and ocular disorders including macular degeneration and optic atrophy. Such diseases or disorders can be treated either by administration of stem cells themselves, permitting in vivo differentiation to the desired cell type with or without the administration of agents to promote the desired differentiation, or by administering stem cells differentiated to the desired cell type in vitro. Efficacy of treatment is determined by a statistically significant change in one or more indicia of the targeted disease or disorder.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

EXAMPLES

While distinct (metastable) pluripotent states are known to exist in mouse and rat, they have thus far not been described for human stem cells. A recent report demonstrates that stable human iPS cells can be derived in the presence of LIF and inhibitors of GSK3β and the TGFIβ and MEK/ERK signaling pathways (Li et al., 2009). However, these cells appear to be molecularly identical to conventional human iPS cells. Human iPS cell derivation was used as a tool to investigate the influence of growth factor signaling on human stem cell pluripotent state. The derivation of human cell lines that display many morphological, molecular and functional characteristics of murine ES cells is demonstrated herein. Expression of ectopic reprogramming factors in the presence of LIF allows the derivation of metastable human stem cell lines with many characteristics of murine ES cells, including a dome-shaped colony morphology, the ability to be propagated by trypsin digest and clonally grown from single cells, and the activation of LIF downstream signaling pathways. It is demonstrated herein that in this "metastable" state, the human cells are more amenable to the introduction of transgenes and allow homologous recombination-mediated gene targeting using standard protocols that have been well established for the targeting of murine ES cells. The LIF-state is metastable, since it depends on the constitutive expression of ectopic reprogramming factors. Yet a combination of growth factors and pharmacological inhibition of MEK-kinase signaling allows the conversion of the human LIF-iPS cells to a stable, pluripotent human iPS cell state.

The findings described herein indicate that, analogous to non-permissive mouse strains and the rat, human iPS cells adopt murine-ES cell properties when the cells are derived in the presence of LIF and continued expression of ectopic reprogramming factors. Importantly, this state facilitates homologous recombination-mediated gene targeting in human stem cells.

Example 1

Figure 1B:
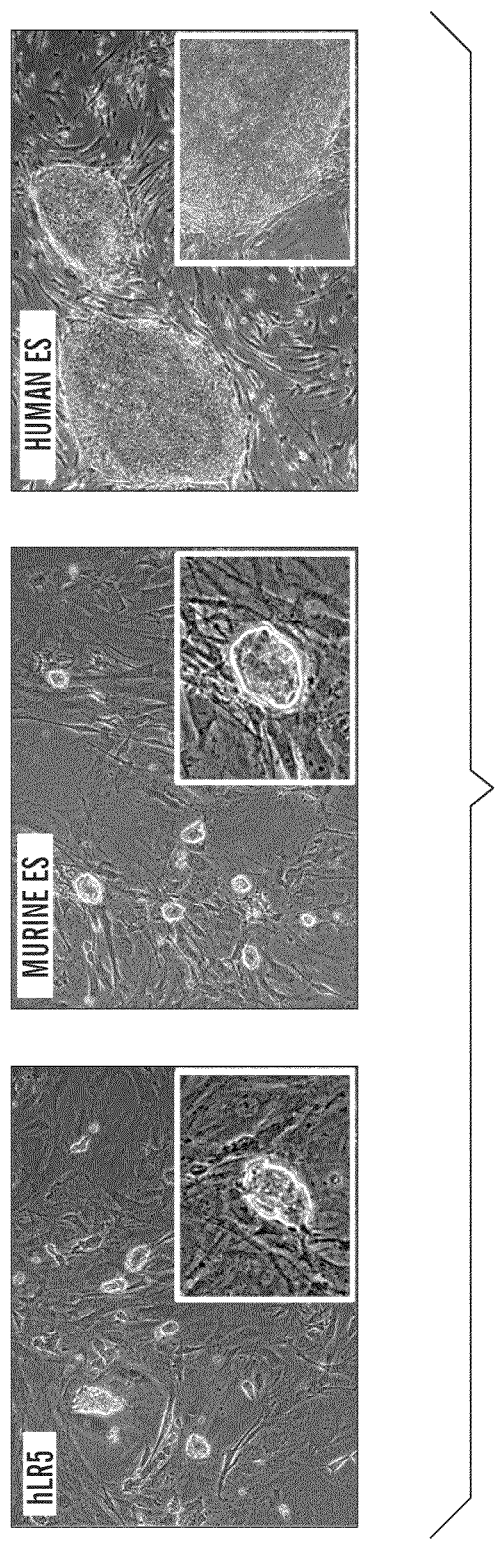
Figure 7B:
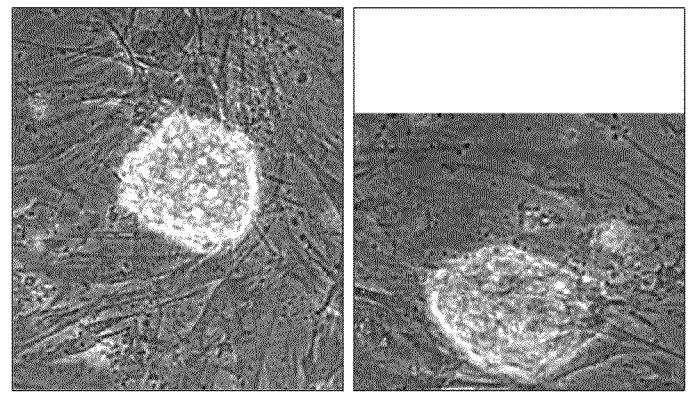
FIGS. 7A-7B: Colony morphologies during the derivation of hLR5 cells. 7A Typical irregular colony morphology of colonies that appear early and cannot be propagated after picking; 7B Morphology of emering hLR5 colonies.
Figure 7A:
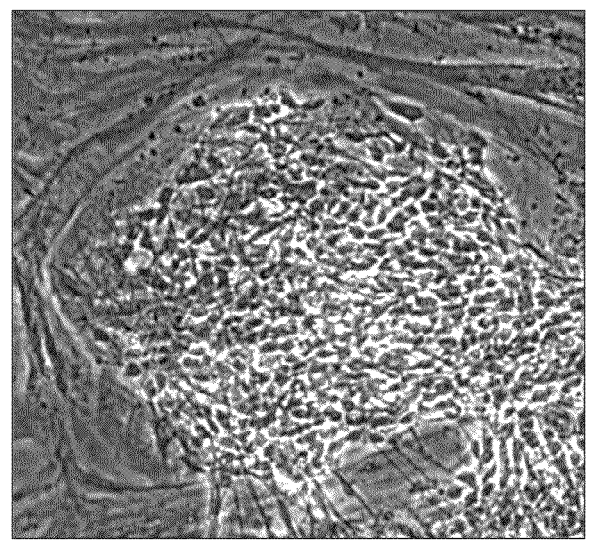

Derivation of Metastable Human iPS Cell Lines with Murine ES Cell Characteristics A recently reported induced pluripotent stem cell (iPS cell) strategy was used to explore the possibility of deriving human iPS cells in the presence of LIF (Lowry et al., 2008; Maherali et al., 2008; Park et al., 2008; Takahashi et al., 2007; Takahashi and Yamanaka, 2006; Yu et al., 2007). An inducible lentiviral system was used to deliver and express the five reprogramming factors OCT4, SOX2, NANOG, c-MYC and KLF4 in human fibroblasts in a doxycycline-inducible fashion through the action of the reverse tetracycline transactivator (rtTA) (FIG. 1A) (Maherali et al., 2008). Fibroblasts were reprogrammed either directly from the primary fibroblasts or from "secondary fibroblasts", derived from successfully established human iPS cells in which the reprogramming efficiency is greatly enhanced (Maherali et al., 2008). Using either approach, doxycycline-induced reprogramming of the human fibroblasts in the presence of human LIF, resulted in the formation of two types of colonies: (i) transient, irregularly shaped colonies that deteriorated a few days after their first appearance and could not be passaged further (FIG. 7A) and (ii) smaller, tightly packed colonies that resemble initial murine iPS cell colonies (FIG. 7B). Individual colonies of the latter group were picked for further clonal analysis. These clones, after passaging, displayed the hallmark, tightly packed, bright, dome-shaped morphology of murine ES cells (FIG. 1B), sharply contrasting the flattened two-dimensional colony morphology of human ES cells (FIG. 1B). These cells were designated human LR5-iPS cells (hLR5) to reflect the conditions in which these cells were derived and maintained (human LIF+ the constitutive expression of 5 reprogramming factors OCT4, SOX2, NANOG, KLF4 and cMYC). No colonies appeared in the control plate, which was cultured in the presence of human LIF, but in the absence of doxycycline (not shown), demonstrating that the induction of ectopic reprogramming factors was essential for the emergence of hLR5 colonies and that no undifferentiated iPS cells remained in the EB-derived fibroblast cultures.

Figure 1C:
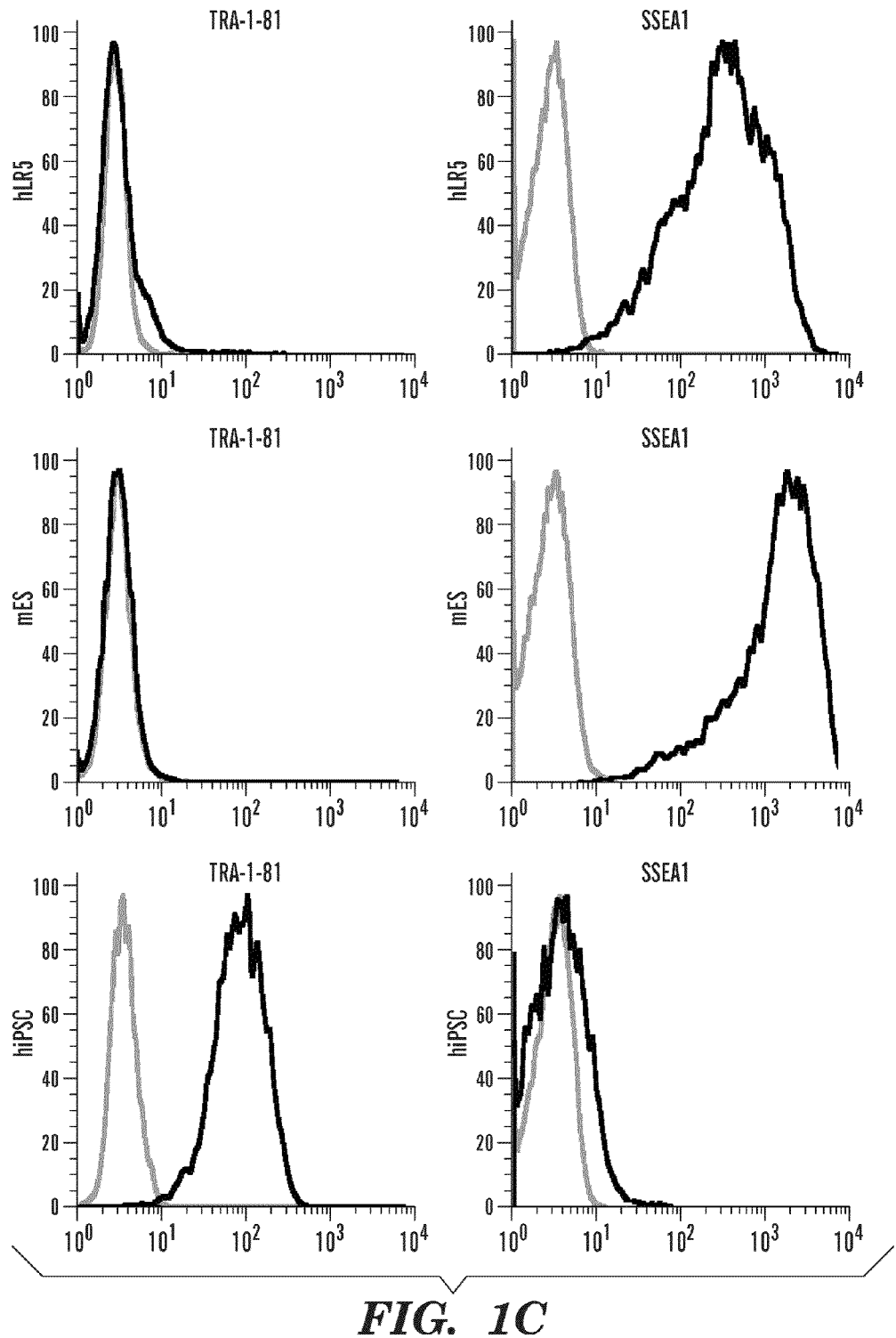
Figure 1D:
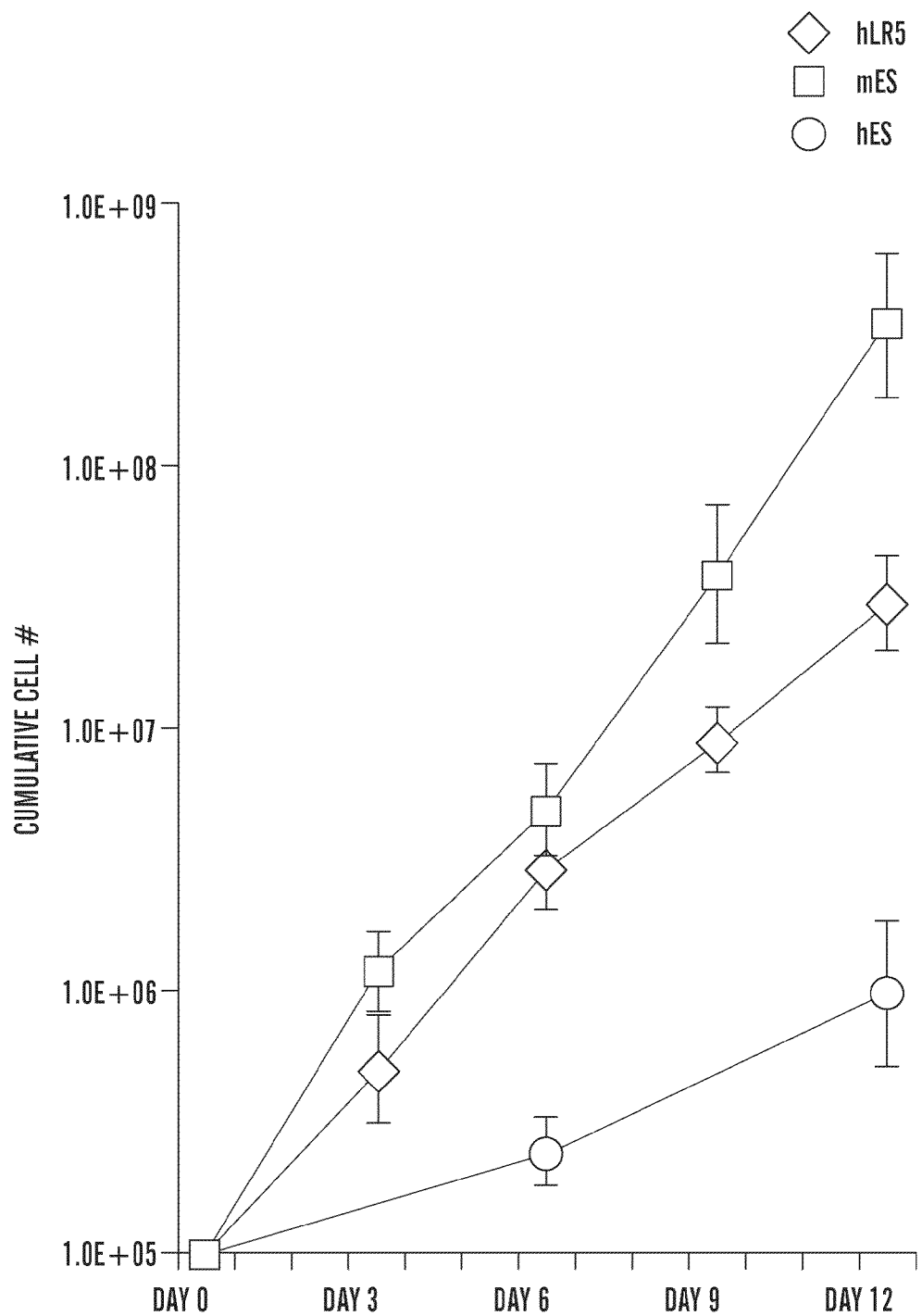

Next, the cell surface marker expression profile of the hLR5 cells was investigated. Murine and human pluripotent stem cells express a mutually exclusive complement of cell surface markers. SSEA1 is expressed on undifferentiated murine pluripotent stem cells but in human ES cells SSEA1 is expressed on differentiating cells. In contrast, the cell surface markers SSEA3, SSEA4, TRA-1-81 and TRA-1-60 are expressed on undifferentiated human pluripotent stem cells while in murine stem cell cultures these markers are indicators of ES cell differentiation. Flow cytometry analysis of the hLR5 cell surface markers revealed a marker profile that resembles the surface marker profile of murine ES cells (FIG. 1C). hLR5 cells do not express the TRA-1-81 cell surface marker, which is characteristic for undifferentiated human pluripotent stem cells (FIG. 1C). However, hLR5 clones demonstrated high expression of the SSEA1 cell surface marker, which is typically expressed on murine pluripotent stem cells (FIG. 1C). A fourth clone, which was derived through direct reprogramming human fibroblasts from a different genetic background also lacked TRA-1-81 expression but expressed low SSEA1 levels, indicating that the level of SSEA1 expression is somewhat heterogeneous between hLR5 clones of different genetic backgrounds. In addition to the general lack of TRA-1-81 expression, hLR5 cells also do not express SSEA3, SSEA4 and TRA-1-60, as tested by flow cytometry and immunohistochemistry (not shown). In addition to their murine ESC-like colony morphology and cell surface marker profile, it was noted that the hLR5 cells, like murine ES cells, can be propagated by trypsin digest, unlike most human ES cell cultures which rely on mechanical- or collagenase-mediated passaging. This result indicated that similar to murine ES cells, hLR5 cells are tolerant to passaging as single cells. Indeed, upon single cell sorting of hLR5 cells into 96 well plates, hLR5 clones re-emerged in approximately 22% of the wells (n=10), similar to the efficiency of single-cell sorted murine ES cells (~30%) whereas upon single-cell sorting of the trypsin-adapted HUES3 human ES cell line (Cowan et al., 2004) into 96-well plates no colonies re-emerged (n=10) reconfirming the intolerance of human ES cells to single cell culture. In addition, the hLR5 cells displayed a much higher proliferation rate than human ES- or iPS cells, with a cell doubling time of approximately 22 hours, corresponding to a 1:5 to 1:7 passaging ratio every other day (FIG. 1D). The hLR5 proliferation rate is close to the murine ES- or murine-iPS cell proliferation rate (doubling time ~16 hours) and much higher than the proliferation rate of human ES- or hiPS cells (doubling time ~37 hours).

Example 2

Activation of the JAK-STAT Pathway and Downstream Target Genes in hLR5 Cells

The growth factor environment is known to be an important determinant of the stem cell pluripotent state (Brons et al., 2007; Chou et al., 2008; Tesar et al., 2007). In murine ES cells, LIF activation of the JAK-Stat signalling pathway mediates stem cell self renewal. Since hLR5 cells display many morphological, molecular and culture characteristics of murine ES cells, including their derivation and maintenance in LIF, the activation of the JAK-STAT pathway was investigated in these cells.

Figure 2A:
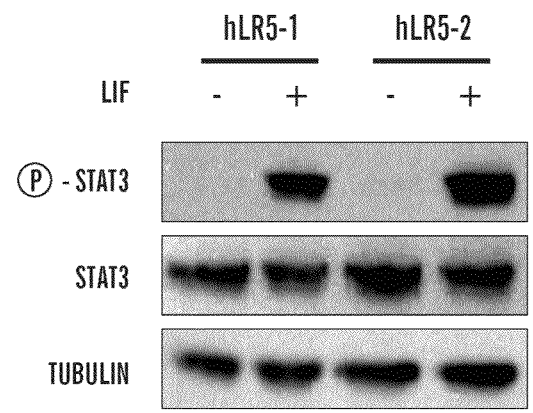
FIGS. 2A-2F: LIF-responsiveness of hLR5 cells. 2A Western blot analysis of STAT3 phosphorylation in two independent hLR5 clones, with or without LIF-stimulation as indicated; 2B Immunostaining of STAT3 subcellular localization in hLR5 cells before (top panel) or after (bottom panel) LIF stimulation. Note the translocation of STAT3 from the cytoplasm (top panel) to the nucleus (bottom panel). Cell nuclei were visualized with DAPI; 2C Gene expression analysis of downstream target genes of the JAK/STAT signaling pathway in three hLR5 clones as well as human ES cell lines and conventional human iPS cell lines; 2D Flow cytometry analysis of SSEA 1 surface marker on hLR5 cells upon LIF removal. Lines indicate (i) LIF control, (ii) LIF substitution with bFGF, and (iii) no added growth factor; 2E Colony morphology of the hLR5 cells before (top panel) and after LIF substitution with bFGF; 2F Flow cytometry analysis of SSEA1 cell surface marker expression on hLR5 cells in the presence of small molecule inhibitors of the JAK/STAT and MEK/ERK signaling pathways. hLR5 cells were maintained in hLR5 media for 1 week in the presence of inhibitors. Grey shaded area: Jak-inhibitor, lines: MEK inhibitors (PD9805, PD1 84352 and PD0325901, as indicated). A line indicating a control (i.e., lacking inhibitor) is also present.
Figure 2B:
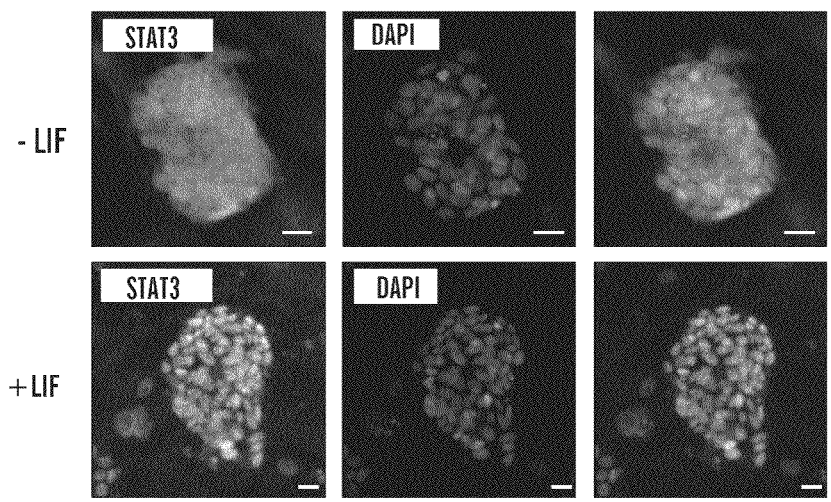
Figure 2C:
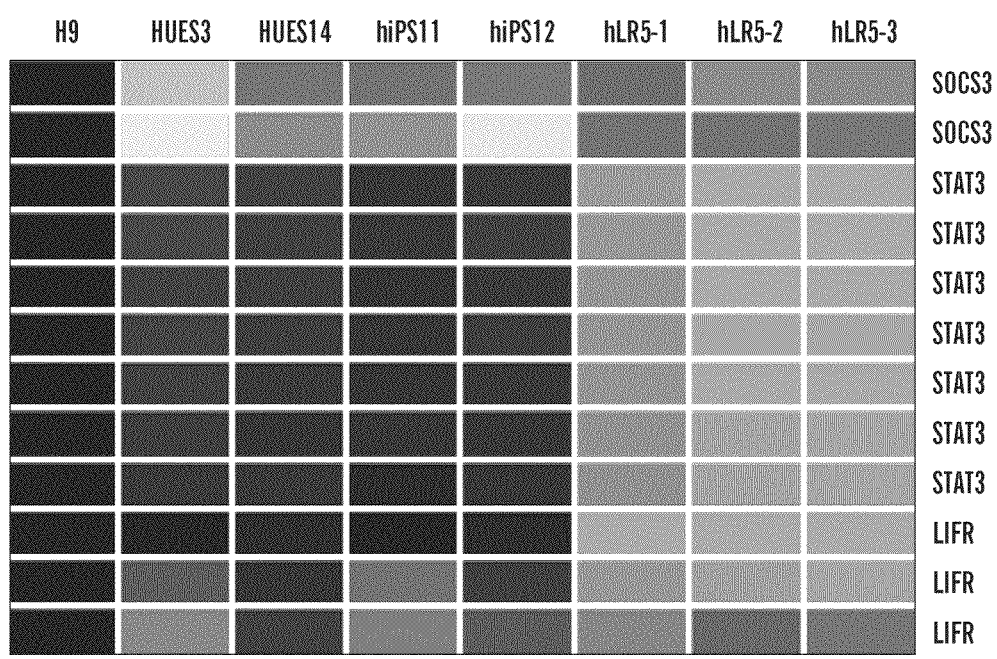

As shown in FIG. 2A, LIF stimulation robustly induces STAT3 phosphorylation in hLR5 cells demonstrating the LIF-dependent activation of the JAK-STAT signaling pathway in these cells (FIG. 2A). Upon LIF activation of the JAK-STAT signaling cascade, STAT3 translocates from the cytosol to the nucleus and directly activates downstream target genes. Indeed, immunofluorescence staining of STAT3 in hLR5 cells revealed nuclear translocation in response to LIF stimulation (FIG. 2B). While STAT3 is cytoplasmic in the absence of LIF (FIG. 2B, top panels), 15 minute stimulation of hLR5 cells with human LIF results in rapid STAT3 nuclear translocation (FIG. 2B, bottom panels). In addition, STAT3 nuclear translocation results in activation of STAT3 downstream target genes, including STAT3 itself as well as SOCS3 and the LIF-receptor, in a LIF-dependent manner, indicating that this pathway is functionally active in response to LIF stimulation of the hLR5 cells (FIG. 2C).

Figure 2D:
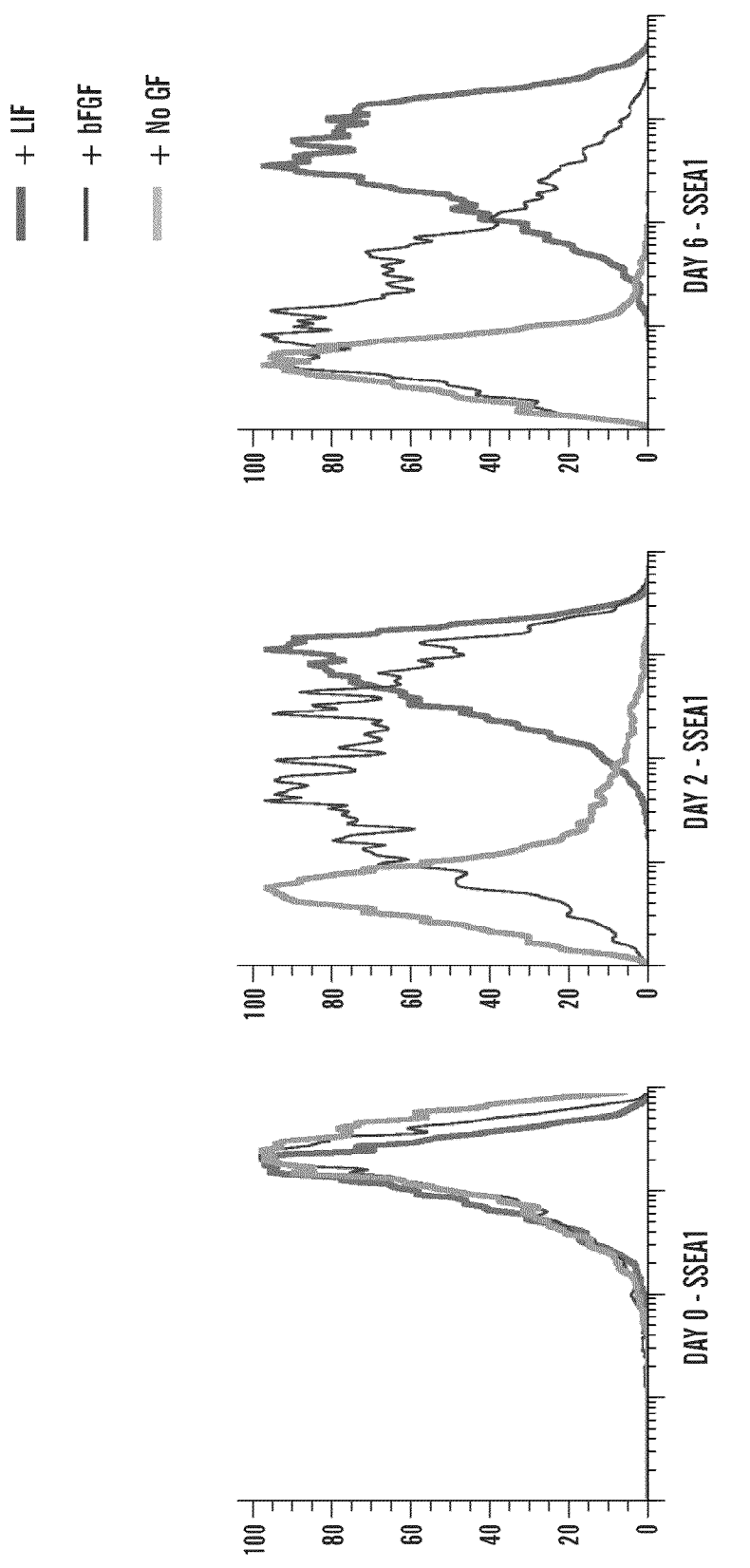
Figure 2E:
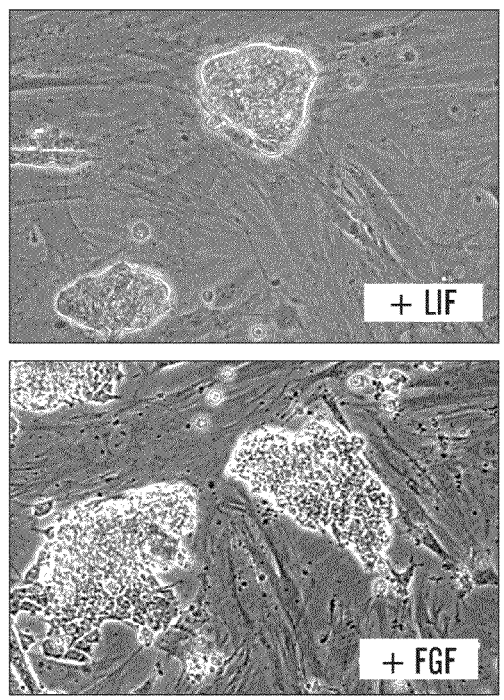
Figure 2F:
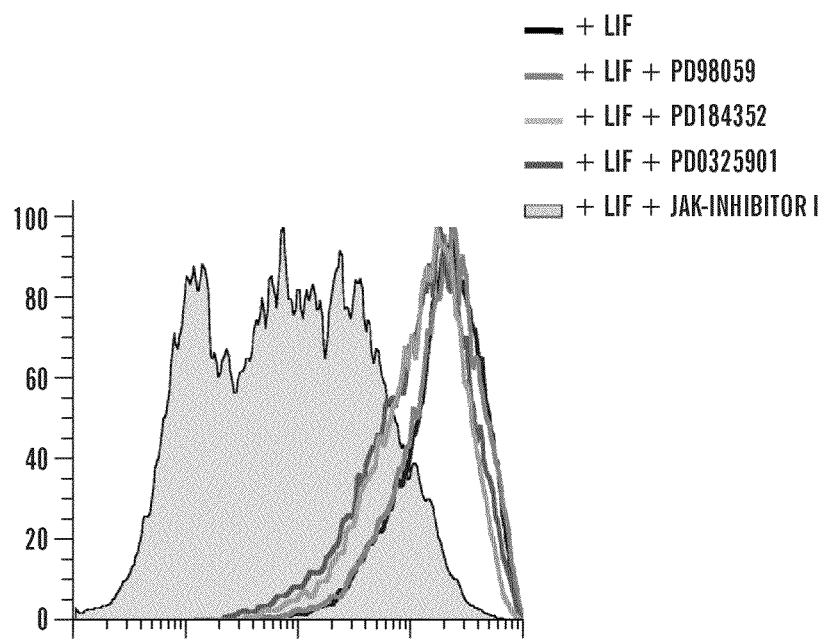

Upon removal or substitution of LIF from the hLR5 culture media, SSEA1 expression waned (FIG. 2D). In addition, a change in colony morphology was observed following LIF withdrawal (FIG. 2E). In murine ES cells, LIF activates the JAK/STAT3 and the RAS/MEK/MAPK signaling pathways, which have opposing roles in murine ES cell maintenance and differentiation. Activation of the JAK-Stat3 signaling pathway has been shown to be both critical and sufficient for long-term self-renewal of murine ES cells, whereas the RAS/MAPK pathway appears to drive murine ES cell differentiation. Indeed, pharmacological inhibitors of the RAS/MEK/MAPK pathway have been shown to enhance murine ES cell self-renewal and in combination with inhibitors of GSK3β allow growth factor independent maintenance of pluripotent stem cells (Ying et al., 2008). Specific inhibitors of JAK/STAT signaling or the MAPK/MEK signaling pathway were used to examine the relative role of these pathways in hLR5 cells. SSEA1 cell surface marker expression was examined by flow cytometry upon culture of hLR5 cells in the presence of specific inhibitors for 1 week. As shown in FIG. 2C, inhibition of the JAK/STAT3 pathway resulted in a marked decrease in the expression of SSEA1 on hLR5 cells (Jak-inhibitor I (0.6 µM), gray shaded area), whereas specific inhibition of the MEK/ERK1/ERK2 pathway did not affect cell surface marker expression (PD98059 (50 µM), PD1 84352 (0.8 µM) and PD0325901 (1 µM), colored lines). Together these results indicate that LIF stimulation of hLR5 cells results in activation of the JAK-STAT3 signaling cascade and upregulation of downstream target genes while LIF withdrawal results in changes in hLR5 colony phenotype. However, LIF withdrawal does not result in hLR5 differentiation, perhaps due to the persistent doxycyclin-induced ectopic expression of reprogramming factors.

Example 3

Figure 3A:
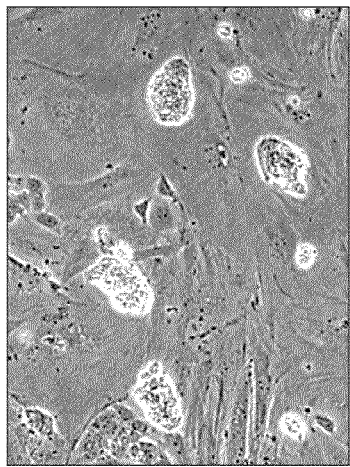
FIGS. 3A-3F: The hLR5 state depends on ectopic pluripotency factors but is poised for re-activation of endogenous pluripotency genes. 3A Ectopic factor dependence of hLR5 cells. Upon doxycycline withdrawal, hLR5 colony morphology is lost and cells adopt a fibroblast-like appearance. Days of differentiation are indicated; 3B Quantitative RT-PCR analysis of the expression of reprogramming factors used for the derivation and maintenance of hLR5 cells. Left panel: expression of endogenous genes. Right panel: expression of the Doxycyclin-inducible ectopic reprogramming factors. Human ES strains (H9, HUES3, HUES14) and human iPS strains (hiPS1, hiPS2) were used as controls. Coding of the genes is indicated (n-3, SD); 3C Chromatin immunoprecipitation and quantitative PCR analysis of the presence of Histone 3 lysine 4 (H3K4, light bars) marks and Histone 3 Lysine 27 (H3K27, dark bars) marks at the promoter regions of the pluripotency genes SOX2, DNMT3b and SALL4 as indicated in hLR5 cells (n=3, SD). 3D Chromatin immunoprecipitation and quantitative PCR analysis analysis of the presence of Histone 3 lysine 4 (H3K4, light bars) marks and Histone 3 Lysine-27 (H3K27, dark bars) marks at the promoter regions of the pluripotency genes OCT4, NANOG and REX1 as indicated in hLR5 cells (n=3, SD); 3E DNA methylation analysis of two CpG islands in the OCT4 promoter as indicated in the schematic of the OCT4 promoter region. Open circles indicate unmethylated and filled circles indicate methylated CpG dinucleotides. Shown are representative sequenced clones from BJ fibroblasts, human iPS cells and two independent clonal hLR5 cell lines. The percentage of CpG methylation at each CpG island in the respective cell lines is indicated. TSS: Transcription start site; 3F Schematic representation of the generation of hLR5 cells in the absence (Top panel, I.) or presence (Bottom panel, II.) of NANOG. While in the absence of NANOG expression traditional hiPS cell can be derived, no hLR5-like colonies form. Addition of ectopic NANOG results in the formation of hLR5 colonies.
Figure 3A:
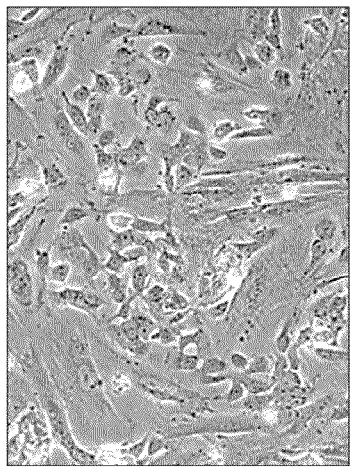
Figure 3A:
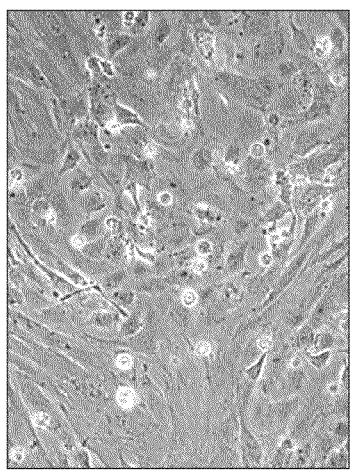
Figure 3B:
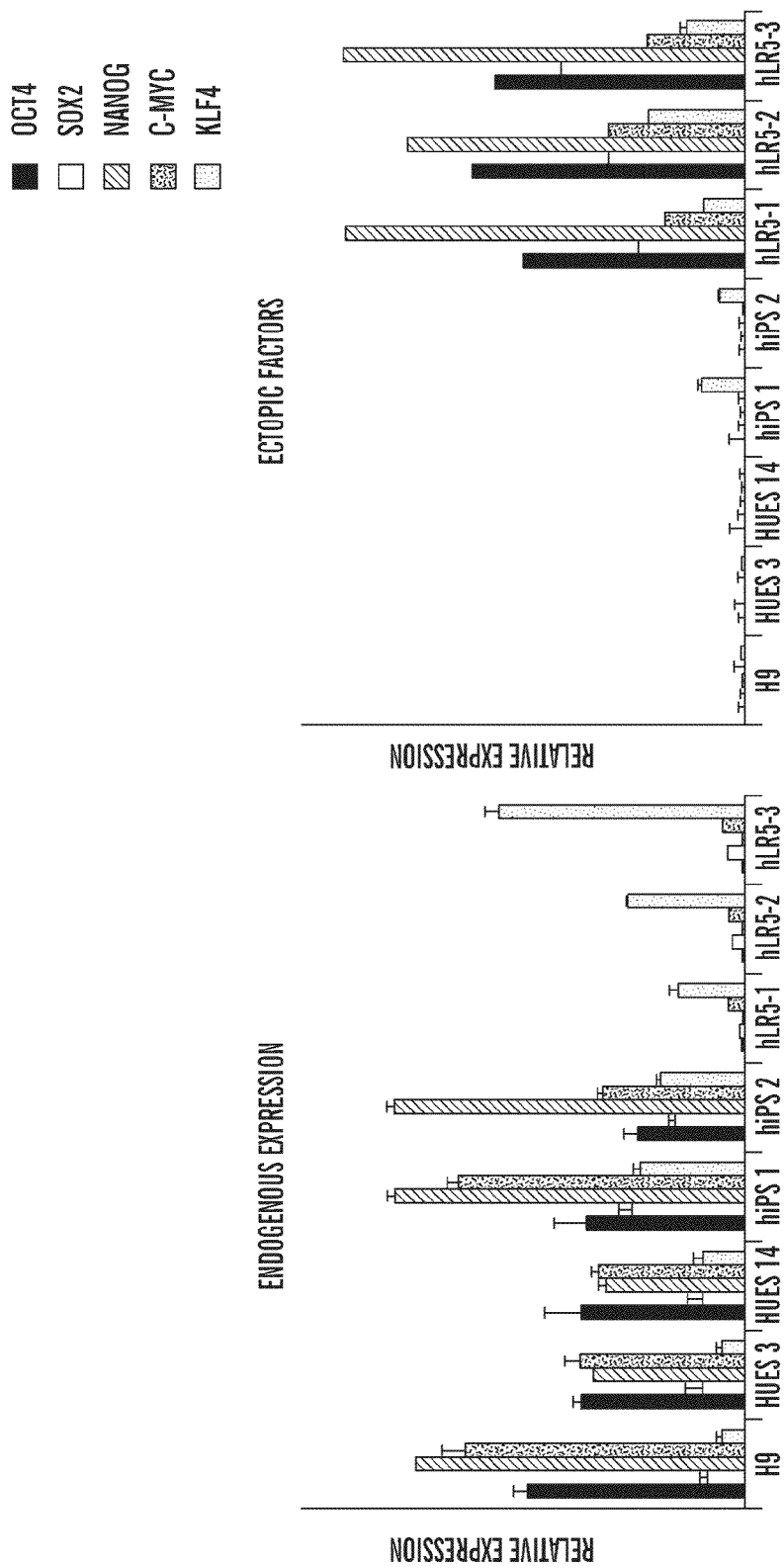

The hLR5 State Requires Continued Ectopic Expression of Five Reprogramming Factors The next question was whether the hLR5 could be stably propagated in the absence of the doxycycline-mediated induction of ectopic reprogramming factors. As shown in FIG. 3A, doxycycline withdrawal resulted in the rapid loss of hLR5 colony morphology, with all cells adopting a fibroblast-like appearance within 3 days after doxycycline withdrawal. A similar dependence on the continued expression of ectopic reprogramming factors was reported for the derivation of rat iPS cells, which require the constitutive expression of four reprogramming factors (Oct4, Sox2, Klf4 and cMyc) (Liao et al., 2009) and for the derivation of iPS cells from the non-permissive NOD mouse strain (Hanna et al., 2009), which require the constitutive expression of Klf4 and/or c-Myc for stable propagation of the iPS state. The need for the expression of ectopic reprogramming factors suggested that in hLR5 cells, the endogenous pluripotency genes have not yet been fully activated. Indeed, Q-PCR analysis of the expression of endogenous and ectopic pluripotency factors revealed that hLR5 cells fail to re-activate endogenous OCT4 and NANOG expression, while the expression of endogenous SOX2 and c-MYC are low (FIG. 3B). Endogenous KLF4 was expressed at similar levels in hLR5 cells and human ES- or iPS cells.

Figure 3C:
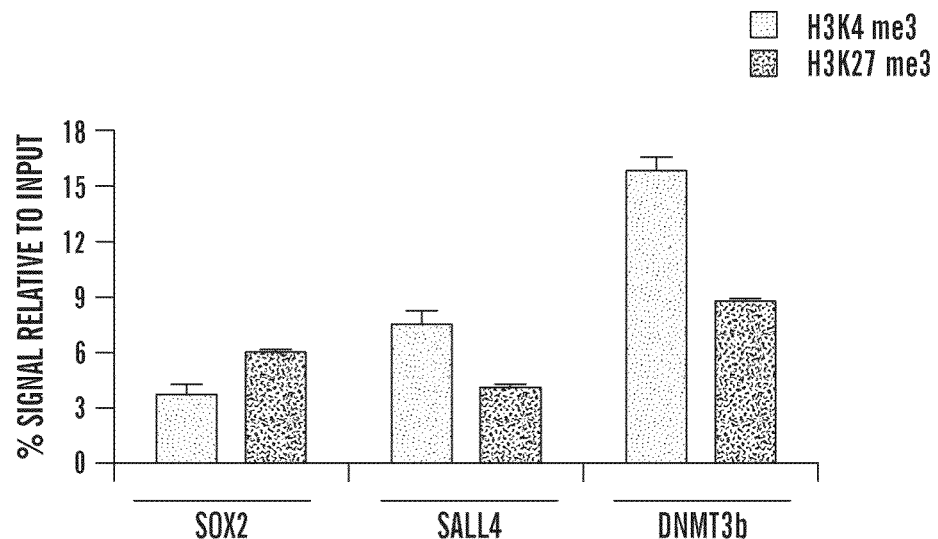

In addition, the presence of activating and silencing histone marks at the promoter regions of critical regulators of pluripotency was analyzed. Using chromatin-immunoprecipitation (ChIP) and Q-PCR, the presence of two histone marks was tested; Histone 3 Lysine 4-methylation (H3K4me3), a histone mark that positively regulates transcription by recruiting nucleosome remodeling enzymes and histone acetylases (Pray-Grant et al., 2005; Santos-Rosa et al., 2003; Sims et al., 2005; Wysocka et al., 2005) and Histone 3-Lysine 27-trimethylation (H3K$_{27}$me3) which promotes stable transcriptional repression (Francis et al., 2004; Ringrose et al., 2004). Unexpectedly, ChIP-qPCR analysis of the presence of H3K4 and K3K27 histone methylation marks at the promoter regions of SOX2, DNMT3b and SALL4 revealed the presence of both the H3K4me3 and H3K27me3 methylation (FIG. 3C). The H3K$_4$ and H3K27 methylation marks have been shown to be simultaneously present in so-called "bivalent domains" which in ES cells are often found at promoters of important transcriptional regulators of development (Bernstein et al., 2006). The presence of bivalent histone marks results in transcriptional repression, but puts the genes in a "poised" state which allows rapid conversion into an active or permanently repressed state by removing either one of the opposing histone marks and is consistent with the low-level endogenous expression of these genes in hLR5 cells (FIG. 3B).

Figure 3D:
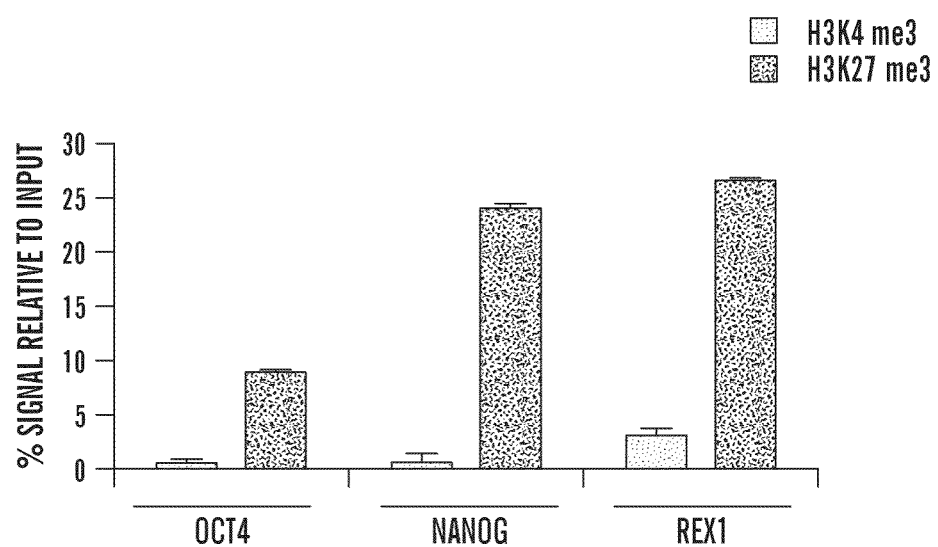
Figure 3E:
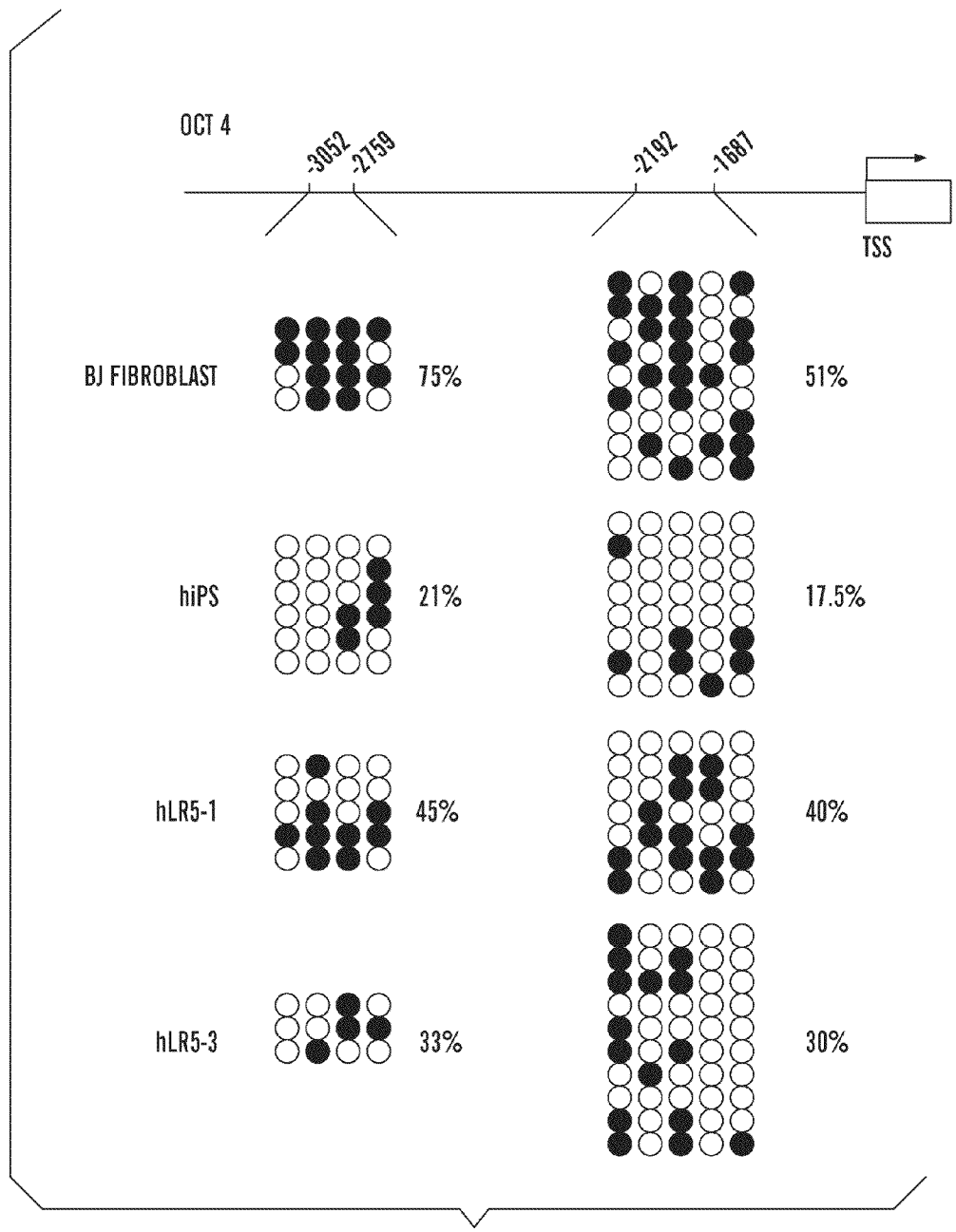

ChIP-PCR analysis of the H3K4 and K3K27 methylation marks at the OCT4, NANOG and REX1 promoters revealed the presence of the repressive H3K27me3 mark in the hLR5 cells, corroborating the absence of endogenous expression of these genes in hLR5 cells (FIG. 3D). In somatic cells, OCT4 and NANOG are silenced through additional epigenetic mechanisms including DNA methylation. While repressing histone marks, such as H3K27 methylation can be readily reversed, DNA methylation is thought to be a permanent transcriptional barrier that is difficult to overcome. Indeed, DNA methylation has been shown to be a limiting step during iPS cell reprogramming and inhibitors of DNA methylation have been shown to complete the reprogramming of partially reprogrammed iPS cells (Mikkelsen et al., 2008). Bisulfite sequencing analysis was performed to determine the DNA methylation status of the OCT4 promoter region in hLR5 cells, fibroblasts and human iPS cells (FIG. 3E). The data show that unexpectedly, the OCT4 promoter regions are hypomethylated in the hLR5 cells as compared to the parental BJ fibroblasts (FIG. 3E).

Together, these results indicate that hLR5 cells exist in a "poised" state of near-pluripotency, in which some pluripotency genes, including SOX2, DNMT3b and SALL4 are in a bivalent histone methylation state, whereas others, such as OCT4, NANOG and REX1 still carry the transcriptionally repressive H3K27 methylation mark, but already display hypomethylation at the OCT4 promoter region.

Figure 3F:
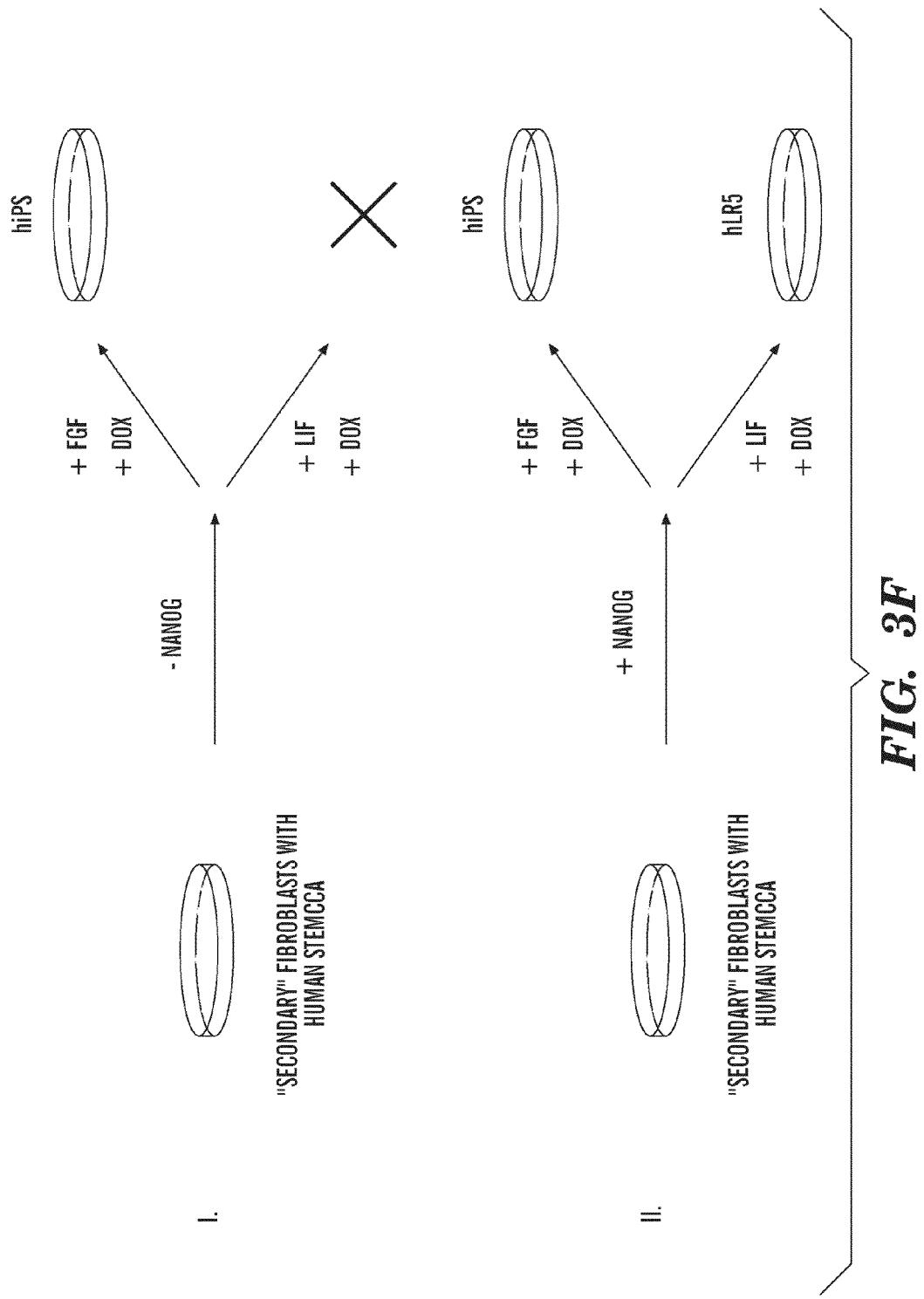
Figure 8A:
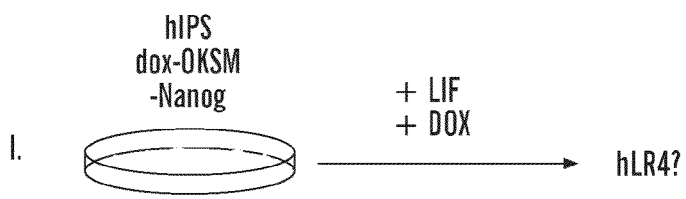
FIGS. 8A-8B: Direct conversion of existing hiPS cells into hLR5 cells. 8A Schematic representation of the conversion of human iPS cells into hLR5 cells in the absence (top panel) or presence (bottom panel) of ectopic NANOG; 8B Morphology of the iPS cells after 3 trypsin passages in hLR5 media in the presence (left panel) or absence (right panel) of NANOG.
Figure 8A:
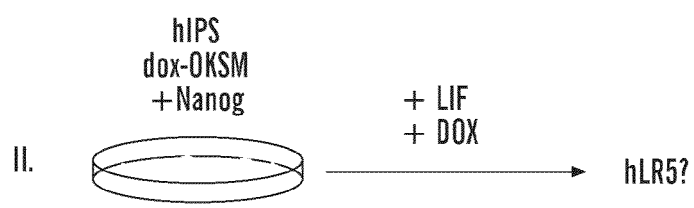
Figure 8B:
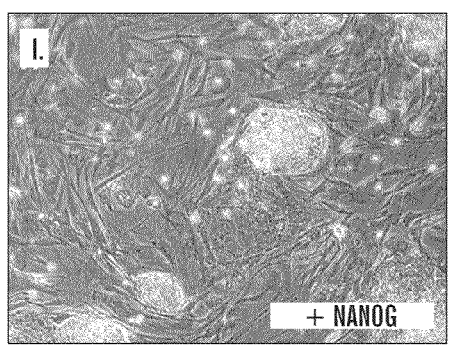
Figure 8B:
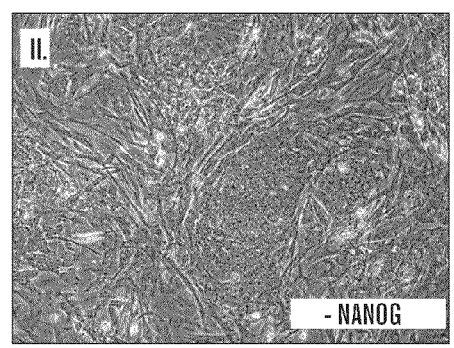

Surprisingly, in addition to the four common reprogramming factors, ectopic expression of Nanog is also required for the maintenance of the hLR5 state. Using the "secondary fibroblasts" discussed above (FIG. 1A), hLR5 cells were generated in the presence or absence of ectopic Nanog expression (FIG. 3F). As before, iPS reprogramming was induced with doxycycline using either conventional human iPS medium (with bFGF) or in hLR5 conditions (LIF). While in the presence of bFGF human iPS colonies formed with or without ectopic NANOG (FIG. 3F, I.), under hLR5 culture conditions IFS colony formation is dependent on ectopic NANOG expression (FIG. 3F, II.), demonstrating that NANOG is required for the de-novo derivation of hLR5 cells. In addition, the effect of ectopic NANOG expression was explored when reactivating reprogramming in existing human iPS cells in hLR5 medium. Using hiPS cells containing the four doxycycline-inducible reprogramming factors OCT4, SOX2, KLF4 and cMYC ectopic factor expression was induced in the presence of human LIF and with or without ectopic NANOG expression (FIG. 8A). In the presence of Nanog expression, colonies appeared after 2-3 passages that showed the typical hLR5 morphology (FIG. 8B, left panel), while without ectopic NANOG expression hiPS colony morphology rapidly deteriorated in hLR5 conditions (FIG. 8B, right panel) demonstrating the requirement for ectopic NANOG expression during the conversion of existing hiPS cells as well. However, hLR5 cell cultures directly derived from hiPS cells remained heterogeneous with some colonies adopting a hiPS cell morphology, indicating that direct conversion of hiPS cells into hLR5 cells was incomplete and may require prolonged passaging and/or selection. Indeed, in a similar manner, the conversion of murine EpiSCs into mES-like cells requires prolonged culture and passaging in combination with selection for cells re-expressing the OCT4-GFP distal enhancer reporter to obtain mES-like colonies (Bao et al., 2009).

Example 4

Conversion of hLR5 Cells to a Stable Pluripotent State

Previous reports have demonstrated that, similar to the hLR5 cells described herein, rat iPS cells and murine iPS cells from the non-permissive NOD genetic background are unstable, and remain dependent on the constitutive expression of ectopic reprogramming factors. However, NOD-derived iPS cells can be converted to a stable, epiblast-like pluripotent state by simultaneously removing the ectopic reprogramming factors and altering the culture growth factor conditions (Hanna et al., 2009). Since the epigenetic analysis demonstrated that many pluripotency regulators are in a "poised" state of near-pluripotency, it was examined whether changes in the growth factor environment could similarly induce the conversion of hLR5 cells into a stable pluripotent state.

Figure 4A:
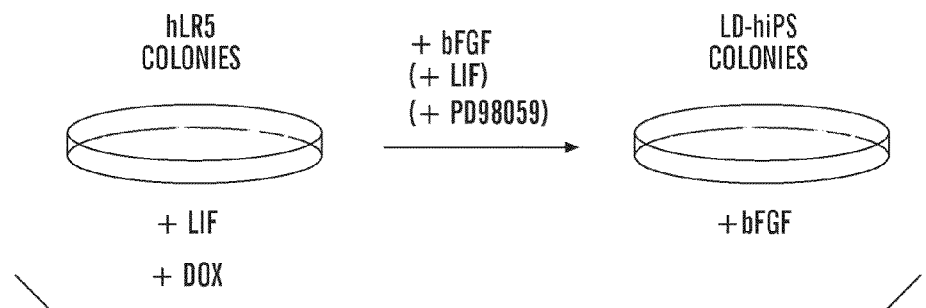
FIGS. 4A-4J: Conversion of hLR5 cells to a stable pluripotent state. 4A Schematic representation of the conversion of hLR5 cells into a stable conventional human iPS cell state; 4B Representative image of the LD-hIPS colony morphology; 4C LD-hiPS cells have a normal 46 XY karyotype; 4D Quantitative RT-PCR analysis of the expression of endogenous pluripotency factors and the silencing of the doxycycline-inducible ectopic reprogramming factors in two independent LD-hiPS clones (n=3, SD); 4E Immunofluorescence analysis of OCT4 (top panels), SOX2 (middle panels) and NANOG (bottom panels) protein expression and nuclear localization in LD-hiPS cells. DAPI was used to visualize the cell nuclei; 4F Immunofluorescence staining of characteristic cell surface markers of human pluripotent stem cells: SSEA4 (top panels), TRA-1-81 (middle panels) and TRA-1-60 (bottom panels). DAPI was used to visualize the cell nuclei; 4G Unbiased cluster analysis of global gene expression profiles of three independent hLR5 clones, two independent LD-hiPS clones, three human ES cell lines and two human iPS cell lines; 4 hours Scatter plots of microarray data on the global gene expression patterns of hLR5 cells, human iPS cells of the same genetic background (hiPS1 2, (Maherali et al., 2008)), Human ES cells (HUES3) and LD-hiPS cells as indicated. The position of individual pluripotency genes listed in the legend is indicated with colored circles; 4I Immunostaining of differentiated LD-hiPS cell lines with markers for mesoderm (SMA, left panel), ectoderm (Tuj 1, middle panel) and endoderm (AFP, right panel) as indicated. DAPI was used to visualize cell nuclei; 4J H&E staining of teratomas generated from clonal LD-hiPS cells. Derivatives of all three germ layers are observed: I. Ganglion, II. Cartilage, III. Adipose tissue, IV. Gut, V. Muscle and VI. Respiratory epithelium and squamous epithelium.
Figure 4B:
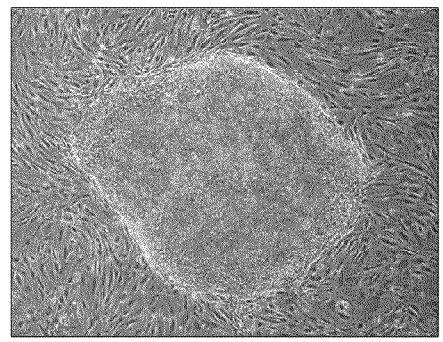
Figure 9:
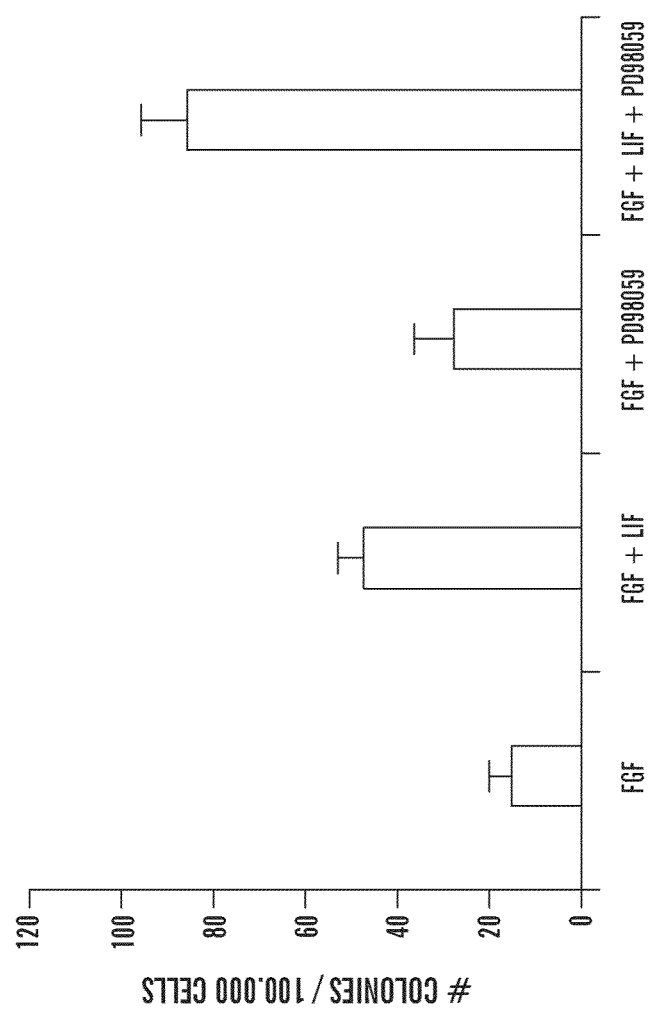
FIG. 9: Conversion rate of hLR5 cells into LD-hi PS cells is influenced by growth factors and inhibition of MEK signaling. Bar graph indicates the average number of stable pluripotent LD-hiPS colonies obtained after plating of 100.000 hLR5 cells in the presence of the indicated combinations of growth factors and MEK inhibitor (PD98059, 50 µM).

FIG. 4A outlines the procedure of converting hLR5 cells into stable iPS cells. Clonal hLR5 cell lines were plated at a density of 5000 cells per cm$^2$ in media containing human LIF and doxycycline to support the continued expression of ectopic reprogramming factors. The next day, doxycycline was withdrawn from the hLR5 cultures and cells were further maintained in the presence of bFGF alone (FIG. 4A). As shown previously, withdrawal of doxycycline-induced ectopic reprogramming factors resulted in the rapid differentiation of most of the hLR5 colonies (FIG. 1E). However, after 7-10 days stable colonies emerged that required mechanical passaging and displayed a typical human iPS-like colony morphology (FIG. 4B). These cells are referred to herein as hLR5-derived human iPS cells (LD-hiPS) to signify their prior hLR5 status. The conversion frequency of hLR5 cells into LD-hiPS cells was low, approximately 0.01%, yet similar to the conversion of murine metastable iPS cells of the NOD strain into stable EpiSC-like iPS cells (Hanna et al., 2009). Pharmacological inhibitors of GSK3β and/or MAPK signaling can substitute some of the reprogramming factors during the derivation of iPS cells and were shown to stabilize the LIF-dependent pluripotent state in iPS and ICM-derived stem cell lines from NOD mice and rat (Buehr et al., 2008; Hanna et al., 2009; Huangfu et al., 2008a; Huangfu et al., 2008b; Li et al., 2009; Liao et al., 2009; Lyssiotis et al., 2009; Shi et al., 2008). Whether LIF and/or small molecule inhibitors could positively influence the conversion of hLR5 cells to a stable pluripotent state was analyzed. Addition of LIF or the MEK inhibitor PD98059 (50 μM) alone resulted in a slight increase in hLR5 conversion rate (FIG. 9), but in combination resulted in a near 8-fold increase in conversion frequency compared to FGF alone. Emerging converted colonies displayed the typical human iPS cell morphology and were subsequently maintained with bFGF alone, indicating that while LIF and PD98059 positively influence the conversion frequency, the resulting iPS cells are not LIF-dependent. A titration curve of GSK3β inhibitor (CHIR99021 or Kenpaullone) alone or in combination with LIF and/or PD98059 did not enhance hLR5 conversion even at high concentration (not shown).

Figure 4C:
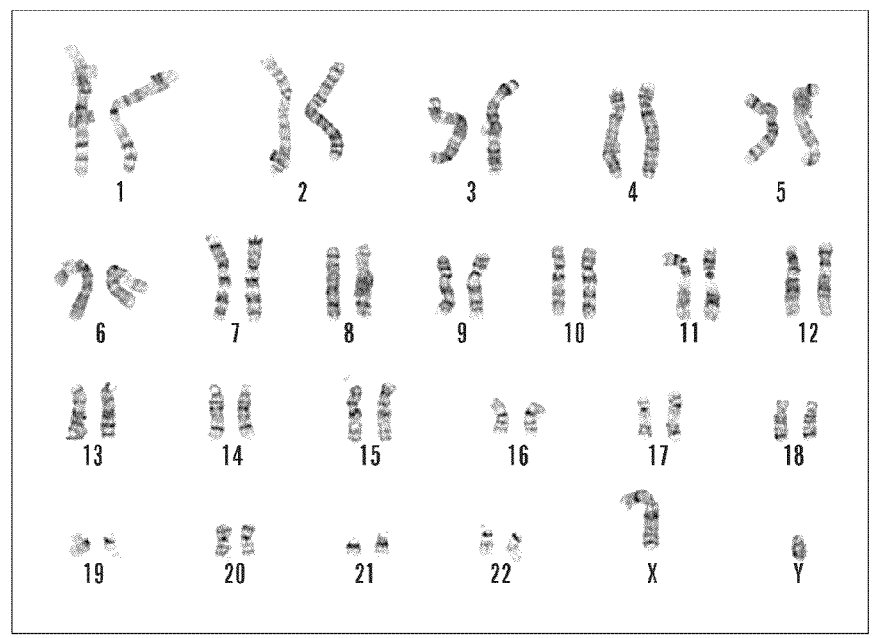
Figure 4D:
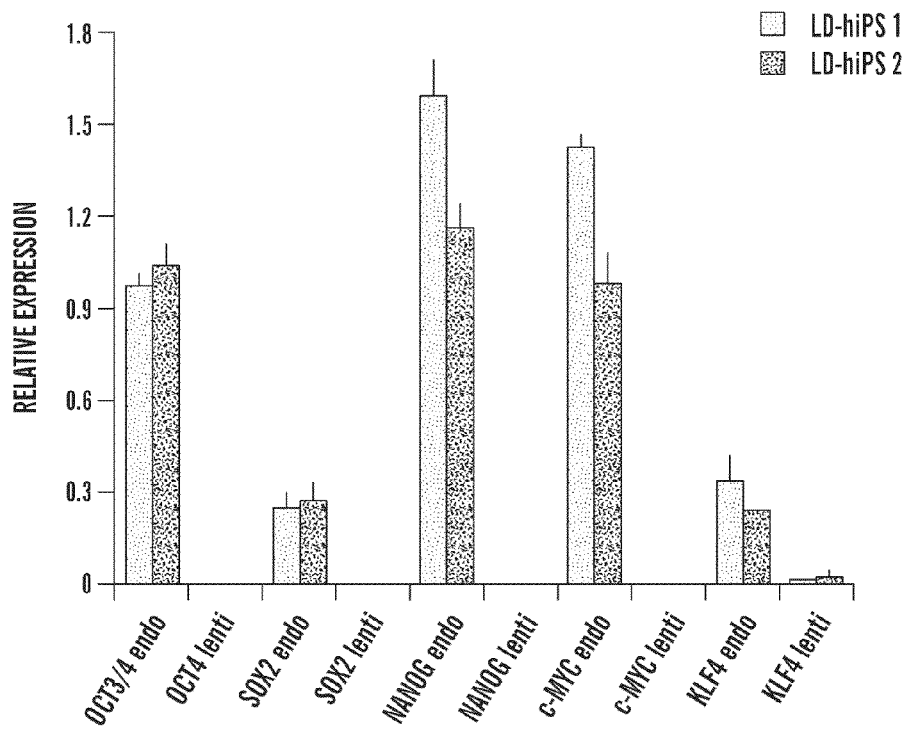
Figures 4E, 4F:
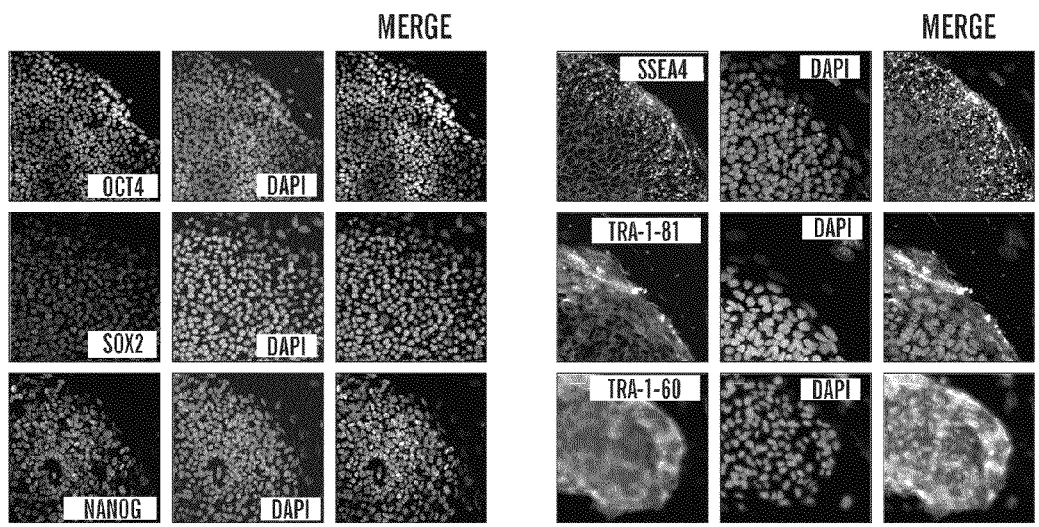
Figure 4G:
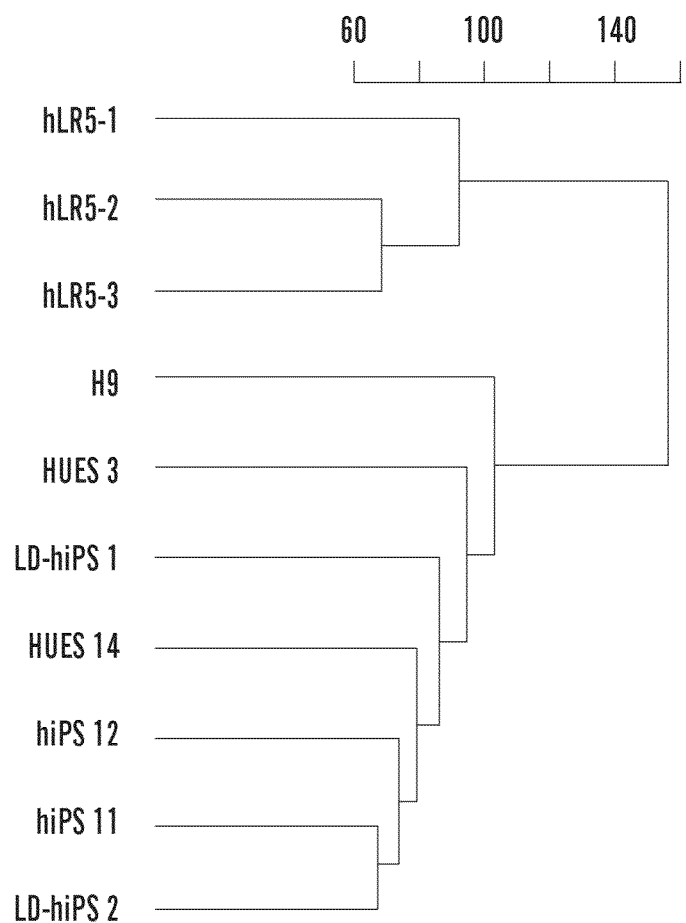
Figure 4H:
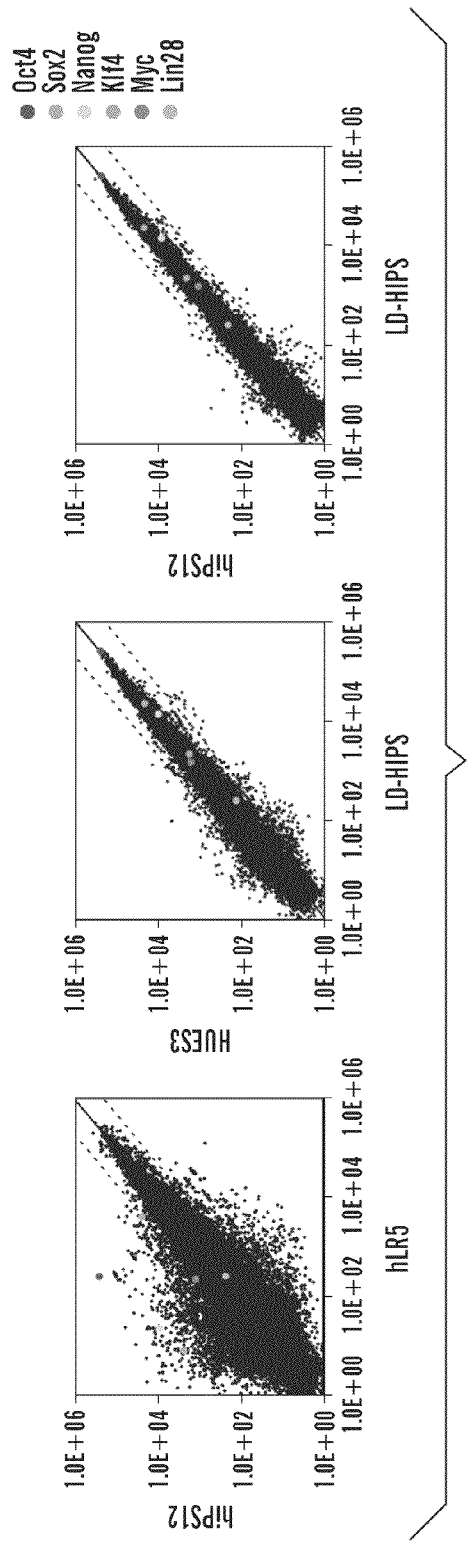
Figure 4I:
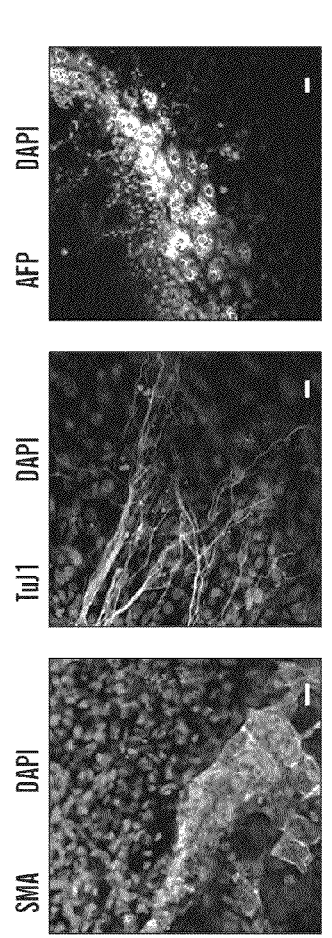
Figure 4J:
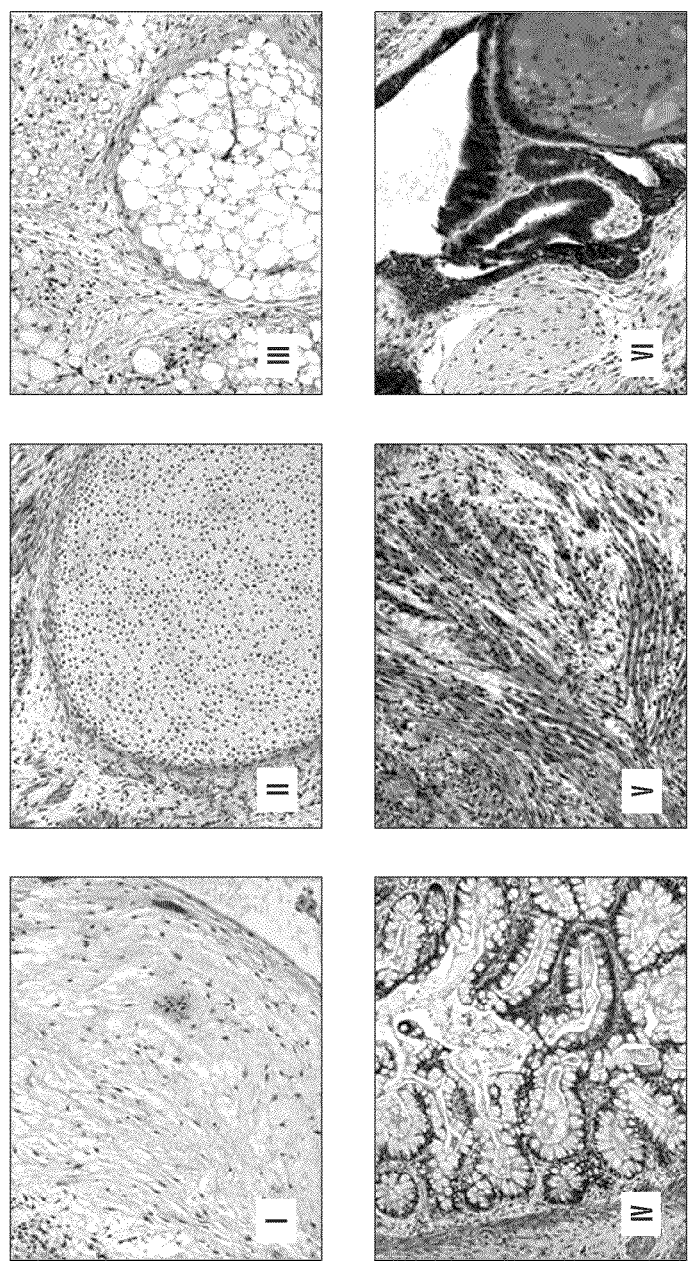
Figure 10:
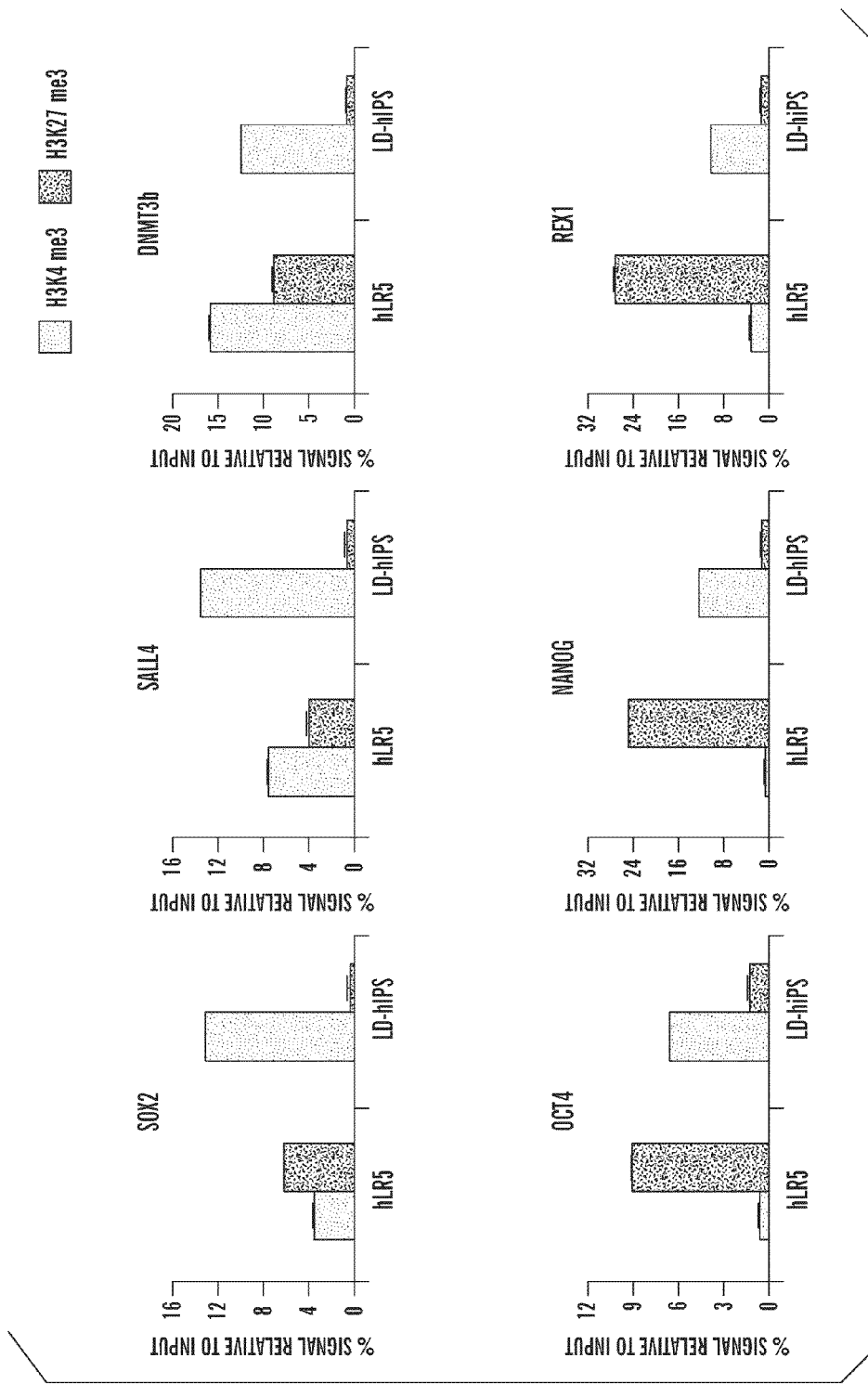
FIG. 10: Reactivation of pluripotency mediators upon hLR5 to LD-hiPS conversion Chromatin immunoprecipitation and quantitative PCR analysis of the presence of Histone 3 lysine 4 (H3K4, light bars) marks and Histone 3 Lysine 27 (H3K27, dark bars) marks at the promoter regions of Sox2, Sall4, Dnmt3b, Oct4, NANOG and Rex1 as indicated in hLR5 cells and LD-hiPS cells.
Figure 11A:
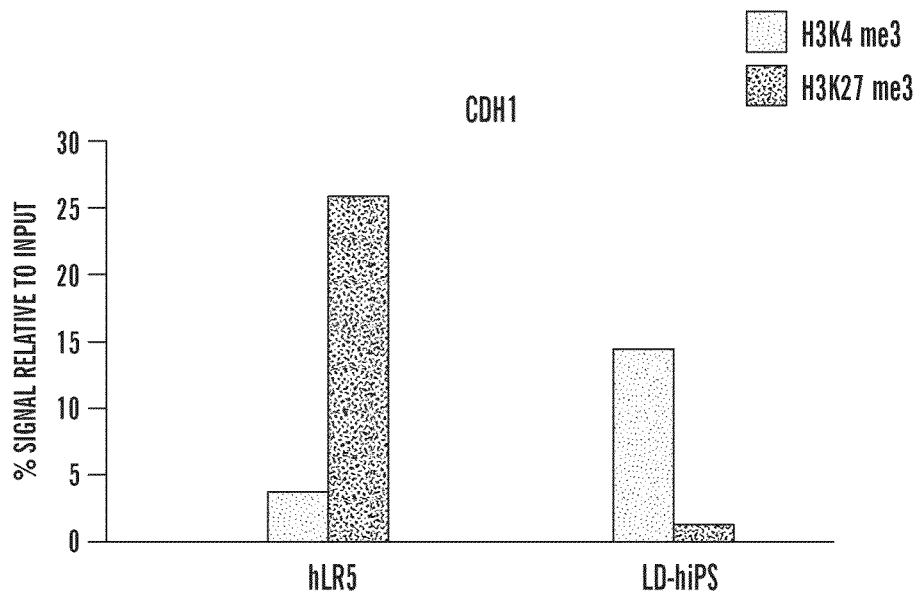
FIGS. 11A-11B: Reactivation of E-Cadherin upon hLR5 to LD-hiPS conversion. 11A Chomatin immunoprecipitation and quantitative PCR analysis of the presence of Histone 3 lysine 4 (H3K4) marks and Histone 3 Lysine 27 (H3K27) marks at the E-Cadherin (Cdh1) promoter in hLR5 cells and LD-hiPS cells as indicated; 11B Western blot analysis of E-Cadherin (Cdh1) expression in hLR5 cells and LD-hiPS cells as indicated.
Figure 11B:
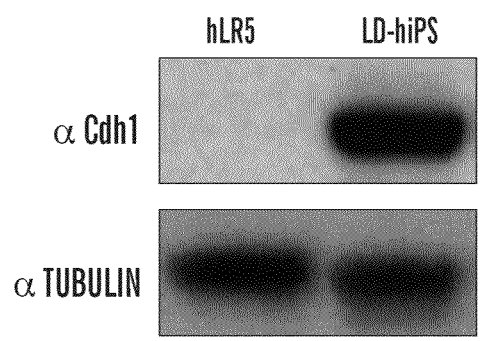

Characterization of three independent LD-hiPS cell lines revealed a normal (2n=46, XY) karyotype of these cells (FIG. 4C) demonstrating that neither the prolonged culture as hLR5 cells (>40 passages) nor the conversion into LD-hiPS had affected genomic stability. Chromatin immunoprecipitation analysis of the H3K4 and H3K27 histone methylation marks at the promoter regions of key pluipotency mediators indicated reactivation of pluripotency genes in LD-hiPS cells (FIG. 10). Indeed, Q-PCR expression analysis of pluripotency regulators demonstrated reactivation of endogenous OCT4, SOX2, NANOG, KLF4 and cMYC in LD-hiPS cells, and the absence of ectopic factors (FIG. 4D). The expression and nuclear localization of OCT4, SOX2 and NANOG was further confirmed using immunofluorescence staining of LD-hiPS cells (FIG. 4E). In addition, the LD-hiPS cells displayed a cell surface marker profile characteristic of human pluripotent stem cells, with expression of TRA-1-60, TRA-1-81 and SSEA4 cell surface markers (FIG. 4F), while the SSEA1 cell surface marker was absent (not shown). In addition, E-Cadherin, a cell-cell interaction protein that is important for pluripotent stem cell maintenance and differentiation, is induced upon conversion of hLR5 cells into LD-hiPS cells, both at the promoter and protein expression level (FIG. 11). Hierarchical cluster analysis of the global gene expression profiles of hLR5 cells, LD-hiPS cells, human ES cells and human iPS cells revealed that LD-hiPS are highly similar to human ES- and iPS cells, whereas hLR5 cells form a separate cluster of unrelated cells (FIG. 4G). Scatter plots of the microarray expression analysis of hLR5 cells and LD-hiPS further highlight the differences between hLR5 cells and the genetically identical hiPS#12 cell line. In contrast, there is high similarity between LD-hiPS and the genetically identical hiPS#12 cell line, but also between LD-hiPS and the genetically unrelated HUES3 human ES cell line (FIG. 4 hours) (Maherali et al., 2008). Finally the ability of LD-hiPS to generate derivatives of the three embryonic germ layers was examined. Embryoid bodies (EBs) were generated from LD-hiPS cells and plated onto gelatin-coated coverslips. The EBs attached and differentiated in vitro into derivatives of the ectoderm, endoderm and mesoderm germ layers. Immunoflurescence staining of EBs revealed the presence of cells expressing TuJ1, a neural marker, Smooth Muscle Actin, a mesoderm lineage marker and alpha-fetoprotein, a marker of endoderm differentiation (FIG. 4I). In addition, some of the EBs started beating, indicating the development of cardiac tissue with pacemaker function. Finally, subcutaneous injection of hLR5 cells into immunocompromised mice resulted in the formation of teratomas containing differentiated derivatives of the three embryonic germ layers (FIG. 4J) demonstrating that the LD-hiPS cells are indeed pluripotent.

transgene insertion was examined using standard electroporation procedures. The transfection efficiency of hLR5 cells was tested using either a 10 kb vector constitutively expressing a red fluorescent protein (tdTomato) driven by the human Ubiquitin promoter and a puromycin selection casette or a 20 kb vector expressing tdTomato driven by the ISL1 promoter (Bu et al., 2009) and a hygromycin selection cassette for identification of positive transfectants. hLR5 cells, or control human ES cells, were electroporated with linearized constructs and after antibiotic-selection of clones that had successfully integrated the transgene, the number of positive colonies was counted. Table 1 summarizes the result of 6 independent electroporations in two independent clonal hLR5 lines (hLR5-1 and hLR5-3) and 29 independent electroporations of human ES cell lines (H9 and HUES3). As is evident from the data, electroporation and selection of the same number of hLR5 cells with the same amount of vector yields over 200-fold more colonies that had incorporated the transgene compared to human ES cell electroporation, demonstrating that hLR5 cells are readily transfectable using standard electroporation procedures, allowing the efficient generation of transgenic hLR5 cell lines. The high efficiency in which hLR5 cells incorporate transgenes is particularly important when large constructs such as BAC clones are used. Indeed, the same electroporation protocol allowed the introduction of a 250 kb BAC clone, which was modified to carry a puromycin selection cassette, albeit at a slightly lower efficiency approximately 1 colony per $10^6$ electroporated cells.

TABLE 1

Introduction of transgenes into human ES cells and hLR5 cells by electroporation

| Experiment | Cell type | # Cells per electroporation | # electroporations | Size of the construct | Drug selection | Average # colonies per $10 \times 10^5$ cells |
|---|---|---|---|---|---|---|
| #1 | Human ES | $1 \times 10^7$ | 10 | 20 kbase | Hygromycin | 6.8 |
| #2 | Human ES | $1 \times 10^7$ | 10 | 20 kbase | Hygromycin | 10.6 |
| #3 | Human ES | $1 \times 10^7$ | 6 | 20 kbase | Hygromycin | 12 |
| #4 | Human ES | $5 \times 10^5$ | 3 | 14 kbase | Puromycin | 5.7 |
| #5 | hLR5 | $1 \times 10^7$ | 2 | 20 kbase | Hygromycin | >>1500 |
| #6 | hLR5 | $1 \times 10^7$ | 2 | 20 kbase | Hygromycin | >>1500 |
| #7 | hLR5 | $1 \times 10^7$ | 1 | 14 kbase | Puromycin | 1300 |
| #8 | hLR5 | $1 \times 10^7$ | 1 | 14 kbase | Puromycin | 1100 |

Example 5 hLR5 Cells Facilitate Transgenesis and Gene Targeting in Human Stem Cells

A major obstacle for the application of human pluripotent stem cells in modeling human development and disease is the difficulty these cells have displayed in allowing the introduction of foreign genetic elements, such as transgenes or reporter constructs (Ptaszek and Cowan, 2007). While such basic molecular manipulations are mainstay in murine ES cells, generation of transgenic human stem cells is very inefficient and labor intensive. As a result, and despite more than a decade of human ES cell research, to date only a handful of papers report the generation of transgenic pluripotent human stem cell lines.

Figure 5A:
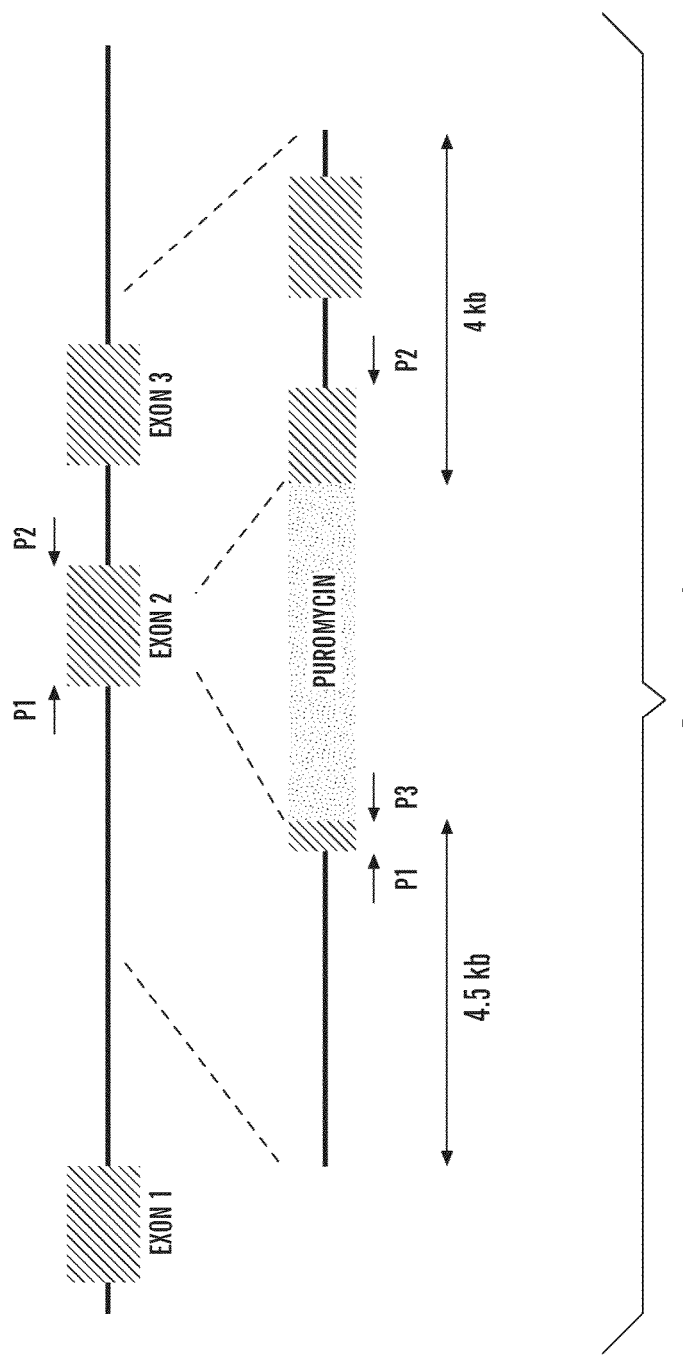
Figure 5C:
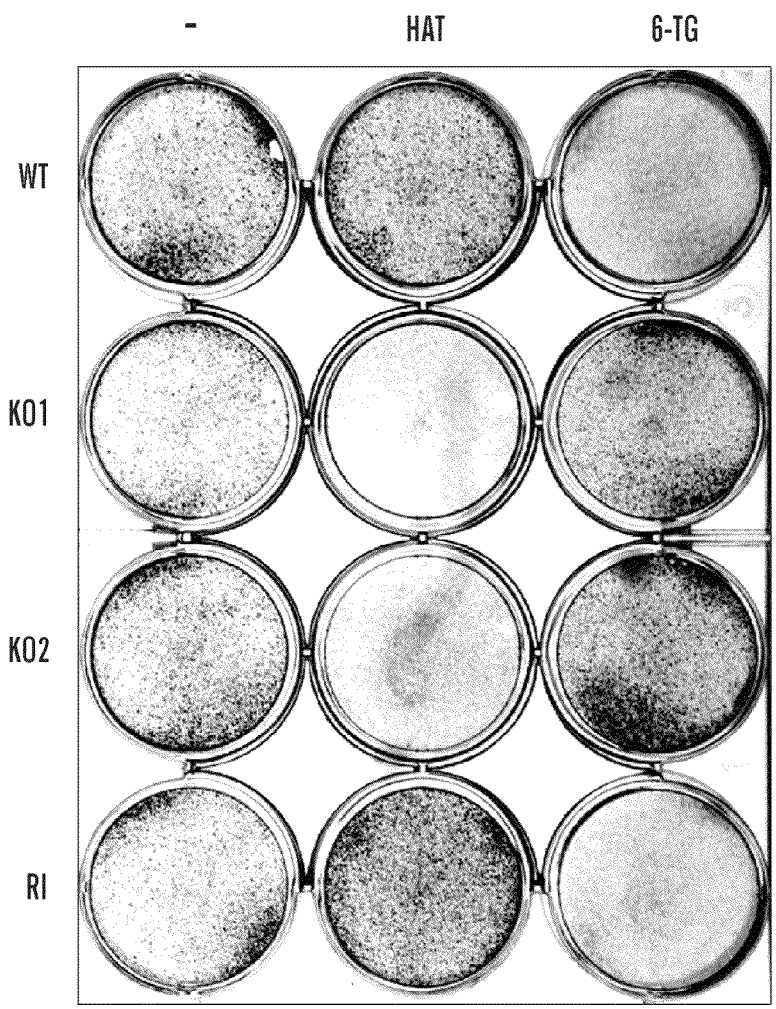
Figure 6:
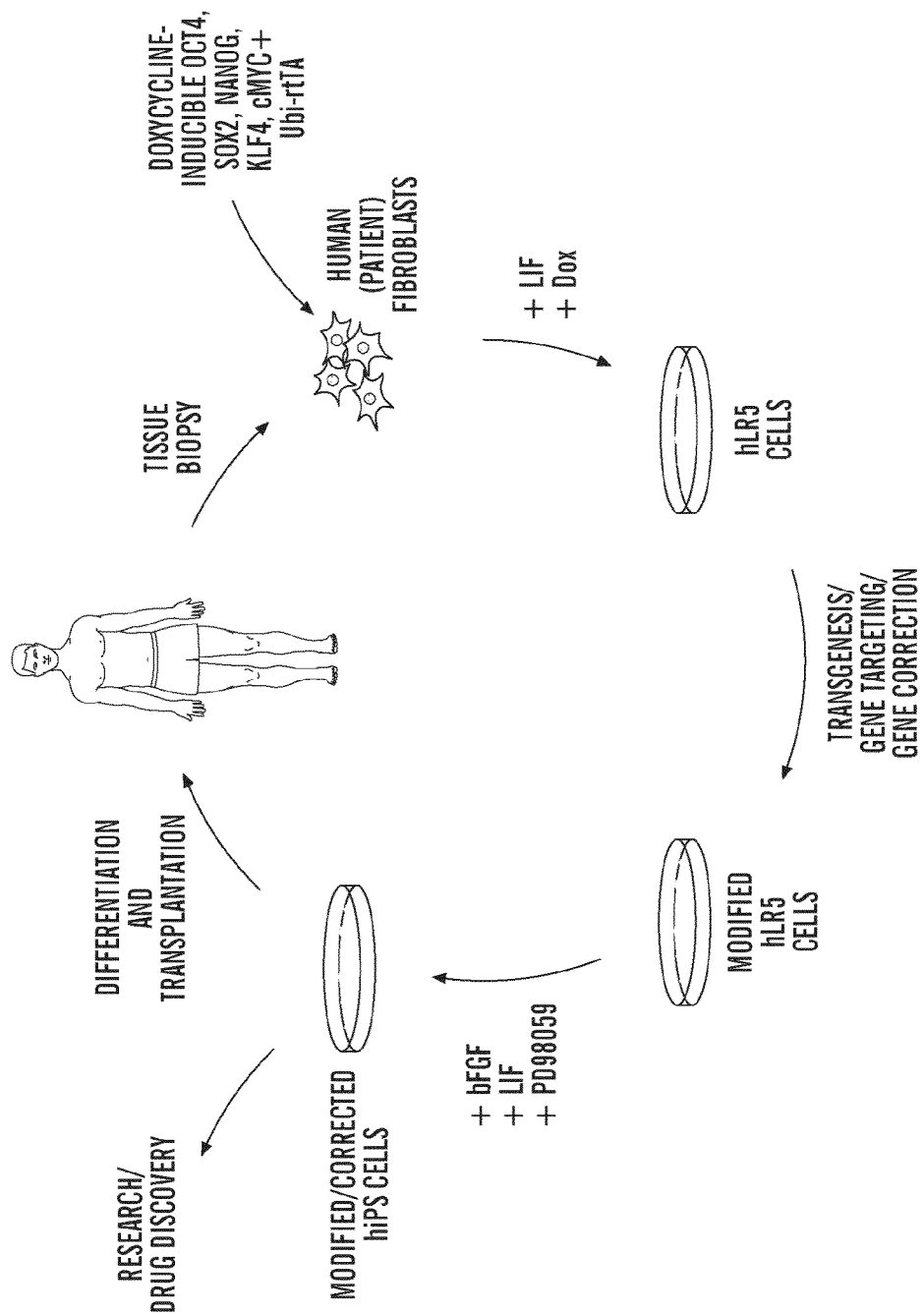
FIG. 6: Application of the intermediate hLR5 state to generate recombinant human pluripotent stem cells for research, drug development and gene correction therapy. Schematic model summarizing the procedure for gene targeting in human (patient) cells via the metastable hLR5 intermediate state. Human primary fibroblasts can be collected and transduced with the five reprogramming factors OCT4, SOX2, NANOG, KLF4 and cMYC. Upon induction of reprogramming in the presence of human LIF, hLR5 colonies emerge. hLR5 cells are targeted using standard protocols and (short) targeting constructs to correct the patient genetic defect or to generate specific gene insertions or knock-out cell lines. The modified hLR5 cells are subsequently converted into pluripotent LD-hiPS cells, which in turn can be used in research or differentiated for use in future cell/gene correction therapies.

Since the human hLR5 cells display many characteristics of murine ES cells, whether these cells are more amenable for Finally, the possibility of targeting specific loci in the hLR5 cell genome was tested. In contrast to murine ES cells, homologous recombination-mediated gene targeting is notoriously difficult in human pluripotent stem cells. We wished to determine if the hLR5 cells perform targeted recombination more efficiently than human ES cells. The hypoxanthine phosphoribosyltransferase (HPRT) locus was chosen as a target in the hLR5 cells, as it offers the benefit of both positive and negative drug selection for the targeted cells. Cells lacking HPRT are resistant to the drug 6-thioguanine (6-TG) but sensitive to HAT selection, while wild-type cells and cells with random integrations are HAT-resistant and 6-TG sensitive. FIG. 5A shows a schematic representation of the human HPRT locus and the targeting construct, which disrupts the second exon by inserting a puromycin selection cassette A combination of three primers (indicated, FIG. 5A) can be used to distinguish between homologous recombination events and random integration of the targeting construct. The primer pair P1+P2 detects the presence of the wild-type HPRT locus while the primer pair P1+P3 detects the presence of the targeting construct in the host cell genome. Since the HPRT gene is located on the X-chromosome and therefore has only one copy in male hLR5 cells, a single targeting event can generate a knockout cell line. Thus, when the targeting construct is integrated through homologous recombination into the HPRT locus, this will yield only the 150 by PCR product (Primers P1 and P3) and eliminate the 500 by (primers P1 and P2) wild-type locus band. In contrast, a random integration event would yield both PCR products. Upon electroporation of hLR5 cells with the HPRT targeting construct, cells were treated with Puromycin to select for positive clones and subsequently treated with 6-TG to select for homologous recombination events. Using this strategy, the targeting efficiency was determined to be approximately 1% (n=3). As shown in FIG. 5B, 6-TG resistant hLR5 clones indeed lacked the wild-type band (FIG. 5B, Upper panel) which is present in wild-type cells and cells with random integration. In addition, the absence of functional HPRT expression in the targeted clones was confirmed by culturing the cells in the presence or absence of HAT supplement, which leaves wild-type and random-integrated cells unaffected, but is lethal to cells lacking HPRT expression. As shown in FIG. 5C, the HPRT knockout cells did not form colonies in the presence of HAT supplement while they were resistant to the positive-selection drug 6-TG, demonstrating the successful targeting of the HPRT locus in hLR5 cells. The wild-type control cells and cells with random integration of the HPRT targeting construct on the other hand, did not form colonies with 6-TG selection, but formed colonies in the presence of HAT supplement.

Recent reports have demonstrated that stem cells can exist in several distinct pluripotent states, which are defined, in part, by the culture growth factor conditions (Brons et al., 2007; Chou et al., 2008; Tesar et al., 2007). bFGF and Activin A allow the derivation of EpiSCs from the egg cylinder of murine post-implantation embryos (Brons et al., 2007; Tesar et al., 2007). EpiSCs display many morphological, molecular and epigenetic characteristics of human ES- and iPS cells, which are derived and maintained under similar growth factor conditions. Remarkably, while EpiSCs can generate derivatives of the three embryonic germ layers upon in vitro differentiation or teratoma formation, the cells fail to contribute to chimeric mice. In contrast, LIF or a combination of GSK3β and MEK inhibitors (2I inhibitors) allows the derivation of murine ES cells from preimplantation blastocysts, which display a characteristic, dome-shaped colony morphology and differ from EpiSCs in their culture dynamics, molecular and epigenetic characteristics and notably, the ability to generate chimeric mice (Evans and Kaufman, 1981; Martin, 1981; Ying et al., 2008).

Yet, only a few inbred mouse strains can spontaneously give rise to stable ES cell lines, while other mouse strains and other species such as rat and primates only give rise to pluripotent stem cells with epiblast-like properties (Brons et al., 2007; Thomson et al., 1998; Thomson and Marshall, 1998). However, the combined use of LIF and 2I inhibitors recently allowed the derivation of true LIF-dependent ES cells from rat blastocysts (Buehr et al., 2008). Remarkably, in the absence of 2I inhibitors, these rat ES cells convert to an EpiSC-like pluripotent state (Buehr et al., 2008). Similarly, the derivation of rat iPS cells requires a combination of LIF and 2I inhibitors (Li et al., 2009) and propagation of rat iPS cells in the absence of 2I inhibitors requires the constitutive overexpression of Oct4, Sox2, Klf4 and c-Myc (Liao et al., 2009). In the mouse, EpiSCs can be converted into ES cells through the overexpression of Klf4 in the presence of 2I inhibitors (Guo et al., 2009). The derivation of ES-like iPS cells from the "non-permissive" NOD mouse strain is similarly dependent on either the constitutive expression of Klf4 or c-Myc or the addition of 2I inhibitors to the culture media (Hanna et al., 2009). It appears therefore that the EpiSC pluripotent state is the common stable pluripotent state for most strains of mice as well as other species, whereas the unique murine ES-like pluripotent state is "metastable" in these genetic backgrounds and requires the constitutive expression of ectopic reprogramming factors and/or the continued presence of pharmacologic inhibitors.

It was found that upon iPS reprogramming of human fibroblasts in the presence of human LIF colonies appear that display hallmark characteristics of murine ES cells, including the dome-shaped tightly packed murine ES cell morphology, the high proliferation rate, the activation of downstream targets of STAT signaling, and the tolerance of trypsin-passaging and single cell cloning. These hLR5 cells could be derived either through direct reprogramming of primary human fibroblasts, or using a more efficient "secondary" fibroblast system. hLR5 cells are metastable, since they depend on the constitutive expression of ectopic reprogramming factors. Upon reprogramming factor removal, hLR5 cells convert to a stable pluripotent state that is indistinguishable from previously described human iPS cell lines. The conversion frequency of hLR5 cells into LD-hiPS cells was similar to the frequencies that have been reported for the conversion of murine metastable iPS cells of the NOD strain into stable EpiSC-like iPS cells (Hanna et al., 2009), about 0.01% and is improved to almost 0.1% when LIF and the MEK inhibitor PD98059 are added during the conversion process. Several arguments support the notion that the emerging LD-hiPS cells are the result of conversion of hLR5 cells into a stable hiPS cell state rather than selection of pre-existing hiPS cells in the hLR5 population. First, the hLR5 cells were clonally derived and maintained for over 30 passages in the presence of LIF before conversion to the LD-hiPS state. Second, the hLR5 cells were continually passaged by trypsinization, which does not allow the propagation of human iPS cells and third, LD-hiPS cells can be derived from hLR5 cells generated directly from primary fibroblasts, which have therefore never before existed in a hiPS cell state. In hLR5 cells, the JAK/STAT3 signalling pathway is activated in a LIF-dependent manner resulting in the expression of STAT3 downstream target genes. In addition, hLR5 cells respond to LIF withdrawal with changes in cell morphology and surface marker expression. Since hLR5 cells in themselves do not form differentiated derivatives upon LIF-withdrawal, probably due to the forced ectopic expression of the five reprogramming factors, the cells are not LIF dependent to the same degree as murine ES cells are. However, continued maintenance of hLR5 in the presence of LIF is critical for the efficient conversion of hLR5 cells into pluripotent LD-hiPS cells, in particular in combination with the MEK inhibitor PD98059.

The conversion of hLR5 cells into hiPS cells is accompanied by epigenetic changes at the promoter regions of critical pluripotency regulators. Unexpectedly, these pluripotency factors, while transcriptionally silent, appear to be in a "poised" state in hLR5 cells, from which they can be rapidly activated. SOX2, DNMT3b and SALL4 display the bivalent H3K4 and H3K27 histone methylation marks, which allow rapid conversion to the transcriptionally active H3K4 methylation state. OCT4, NANOG and REX1 are silenced by the H3K27 mark, yet DNA methylation analysis reveals that the OCT4 promoter region is hypomethylated in the hLR5 cells, greatly facilitating OCT4 reactivation. Similarly, the metastable iPS cells derived from the NOD mouse strain display hypomethylation at the Oct4 promoter (Hanna et al., 2009), indicating that demethylation of promoter regions of critical pluripotency regulators is an essential property of the metastable state that allows gene reactivation and stable conversion to the epiblast-like pluripotent state.

Interestingly, the number of ectopic factors that is required to stabilize the murine ES-like state differs between the murine NOD strain, rat and human. While murine metastable NOD-iPS cells can be maintained with the constitutive expression of a single factor (either cMyc or Klf4) (Hanna et al., 2009), rat metastable iPS cell lines require the full complement of reprogramming factors (Liao et al., 2009), and in the case of the hLR5 cells this repertoire is expanded with the addition of NANOG.

Murine ES cell-based technologies have been instrumental in the discovery of gene function in the context of mammalian development and disease. The standard techniques that readily allow the introduction of transgene and reporter gene constructs in murine ES cells work poorly in human pluripotent stem cells. As a result, the ability to introduce foreign genetic elements into human cells is largely limited to the use of lentiviral vectors, or the use of site-specific zinc-finger nucleases which are expensive and of which off-target effects are suspected but not well characterized. These limitations hamper the generation of recombinant human stem cell lines and ultimately complicate the use of such cells in future patient applications. It is demonstrated herein that large reporter constructs and even 250 kb BAC clones (average BAC clones are about 100 kb) can be introduced into hLR5 cells. hLR5 cells even allow homologous recombination-based gene targeting. Until now, the (targeted) introduction of genetic elements into human pluripotent stem cells was highly inefficient and largely impractical. The intolerance of human stem cells to grow from single cells resulted in very low colony yields upon antibiotic selection of positive transfectants and the low proliferation rate of human pluripotent stem cells made the process time consuming and labor intensive. Recently, Song et al reported a recombinant BAC-based strategy for gene targeting in human pluripotent stem cells (Song et al.). While a BAC-based system has the advantage of high homologous recombination efficiency due to the large homologous regions flanking the targeting cassette, the system still suffers from the same practical difficulties associated with introducing a large BAC clone into human pluripotent stem cells, the low numbers of clones after antibiotic selection and the added technical difficulties in distinguishing homologous recombination from random integration events when large BAC clones are used. In contrast, hLR5 cells are tolerant to clonal selection, even when the fast-acting puromycin selection cassette was used and hLR5 cells have a high proliferation rate akin to mES cells, which further facilitates clonal outgrowth and selection. Finally, hLR5 cells allow gene targeting with small (4 kb) homologous arms using standard electroporation procedures that have been well established for the targeting of murine ES cells. The limited size of the homologous arms facilitates the identification of true recombinants by simple PCR or Southern blotting procedures. Combined with the ability of hLR5 cells to convert into a stable iPS state it is demonstrated herein that the hLR5 intermediate provides an efficient platform for targeted gene modification and/or correction in human pluripotent stem cells (FIG. 6). As such, human stem cell intermediates of this sort can find use in the generation of recombinant human cell lines for biomedical research and drug development and find application in future cell- or gene correction therapies.

Example 6

Exemplary Experimental Procedures

Culture of Human ES and iPS Cells

Human ES Cells (H9, HUES3 and HUES14) or human iPS cells (clones 11 and 12) (Maherali et al., 2008) were maintained on γ-irradiated MEFs in DMEM/F12 containing 20% knockout serum replacement, 2 mM L-Glutamine, 1% non-essential amino acids, 100 U of penicillin, 100 μg of streptomycin (all from Invitrogen), 0.1 mM β-mercaptoethanol (Sigma), and 5 ng/ml bFGF (R&D systems). Cells were routinely passaged every 5-7 days either enzymatically using 1 ng/ml Collagenase or manually by scraping the colonies from the plate and soft trituration. For EB derivation, colonies were picked manually from the plate and collected in EB medium (IMDM containing 15% FBS, 2 mM L-Glutamine, 1% non-essential amino acids, 1 mM Sodium Pyruvate, 100 U of penicillin, 100 μg of streptomycin (all from Invitrogen) 200 μg/mL iron-saturated transferrin (Sigma), 4.5 mM monothioglycerol (Sigma), 50 μg/mL ascorbic acid (Sigma)). Colonies were cultured with gentle agitation. Half of the EB tissue culture media was exchanged every day for the duration of the EB culture. After 7-9 days colonies were transferred to gelatin coated chamber slides in EB medium, allowed to adhere and incubated for 3-5 more days. For teratoma formation LD-hiPS were injected subcutaneously into NOD mice (Jackson Laboratories, Bar Harbor, Me.). After ~10-12 weeks teratomas were dissected, washed with PBS and fixed with 4% PFA over night at 4° C. Paraformaldehyde in sections were stained with hematoxylin/eosin to visualize differentiated tissues.

Derivation and Maintenance of hLR5 Cells

EBs were generated from Clone#12 hiPSC colonies (Maherali et al., 2008) by mechanical picking and suspension culture with EB media. After 1 week, embryoid bodies dissociated using collagenase (Sigma) and cells were allowed to adhere to tissue culture plastic in fibroblast media DMEM containing 10% FBS, 100 U of penicillin and 100 μg of streptomycin (all from INVITROGEN™). Cells were passaged by trypsin digest for an additional 5 passages, upon which the culture had a homogeneous fibroblast appearance. To confirm the absence of residual hiPS cells, 20% of the culture was plated onto MEF feeders in human ES cell media (DMEM/F1 2 containing 20% Knockout Serum Replacement, 100 U of penicillin, 100 μg of streptomycin, 2 mM L-Glutamine, 1% non-essential amino acids (all from INVITROGEN™), 0.1 mM β-mercaptoethanol (Sigma) and 5 ng/ml human bFGF (R&D SYSTEMS™). No iPS colonies emerged from this control plate. The remaining fibroblasts were induced to generate hLR5 cells by passaging the cells onto MEF feeders in hLR5 media (DMEM/F12 containing 20% Knockout Serum Replacement, 100 U of penicillin, 100 μg of streptomycin, 2 mM L-Glutamine, 1% non-essential amino acids (all from INVITROGEN™), 0.1 mM β-mercaptoethanol (SIGMA™), 10 ng/ml human LIF (SIGMA™) and 2 μg/ml Doxycycline (SIGMA™). Emerging colonies were individually picked and subcultured by trypsin digest in hLR5 media on MEF feeders. For the direct reprogramming of human fibroblasts (HS27, ATCC) into hLR5 cells $10^5$ cells per 1 $cm^2$ were transduced with the STEMCCA lentivirus (containing doxycycline-inducible human OCT4, SOX2, KLF4 and cMYC) and rtTA with or without a doxycycline-inducible lentivirus for NANOG (Maherali et al., 2008; Sommer et al., 2009; Stadtfeld et al., 2008). 24 hours after lentiviral transduction, reprogramming was induced using 2 ng/ml Doxycycline. The next day cells were passaged onto murine embryonic fibroblasts (MEFs) and after one more day the media was switched to hES media plus DOX or hLR5 media plus Dox as indicated. After approximately 30 days, emerging colonies were individually picked and expanded further by trypsin digest in hLR5 media with MEF feeders. hLR5 cells are passaged at a 1:5 to 1:7 ratio every other day, depending on culture density.

Q-PCR Analysis

Total RNA was extracted using Trizol (INVITROGEN™) following the manufacturer's protocol. cDNA synthesis (SUPERSCRIPT III FIRST STRAND™ synthesis system, INVITROGEN™) was performed using random primers. qRT-PCRs were carried out using Brilliant II SYBR Green mix (STRATAGENE™) and a STRATAGENE™ MXPro400 real-time thermocycler. Primer sequences for the analysis of endogenous and ectopic pluripotency gene expression were reported previously (Maherali et al., 2008).

Microarray Analysis

For genome-wide expression analysis, total RNA was extracted using Trizol reagent (INVITROGENT™) and labeled and hybridized to Agilent Whole Human Genome Oligo 4×44K Microarrays (one-color platform) according to the manufacturer's protocols. The gene expression results were analyzed using GENESIFTER™ microarray analysis software.

FACS Analysis

Cells were collected by trypsinization and resuspended in ice-cold RPMI+0.5% FBS. Cells were incubated with the antibodies against the indicated surface antigens for 30 min at 4° C. The following antibodies were used for cell surface marker profiling: SSEA 1 (BD BIOSCIENCES™), TRA-1-81, TRA-1-60, SSEA3 and SSEA4 (MILLIPORE™). Cells were washed twice with RPMI/0.5% FBS and incubated with the relevant fluorophore-conjugated secondary antibody (BD BIOSCIENCES™) for 30 min at 4° C. Cells were washed twice with RPMI/0.5% FBS, resuspended in RPMI/0.5% FBS and analyzed on a BECTON-DICKINSON FACSCALIBUR™ cell analyzer.

Electroporation and Gene Targeting 5-10×10⁶ cells (as indicated) were dissociated using Trypsin/EDTA (INVITROGEN™) and filtered through a 100 µm cell strainer. Cells were resuspended either in 700 µl PBS containing 15-30 µg linearized DNA, and transferred to a 0.4 cm gap electroporation cuvette (BIORAD™). The electroporation was carried out using a single 320V, 200 uF pulse. Upon electroporation, cells were replated at 5×10⁵ cells/cm² onto gelatinized dishes containing drug-resistant DR4MEFs. Antibiotic selection was started 48-72 h later using either 25 µg/ml Hygromycin (INVITROGENT™) or 0.25 µg/ml Puromycin (INVIVOGEN™) as indicated. HPRT targeting was done using the indicated targeting construct with 4-4.5 kb homologous arms flanking a puromycin selection cassette. After electroporation, hLR5 cells were selected with Puromycin to select for cells that incorporated the targeting construct followed by treatment with 6-Thioguanine (6-TG, Sigma) to select for homologous recombinants. HAT-selection was carried out by adding 1×HAT supplement (INVITROGEN™) directly to the hLR5 medium.

ChIP

Cells were fixed in 1% formaldehyde for 10 minutes, quenched with glycine and washed 3 times with PBS. Cells were then resuspended in lysis buffer and sonicated 10×30 sec in a BIORUPTOR™ (Diagenode, Philadelphia, Pa.) to shear the chromatin to an average length of 600 bp.

Supernatants were precleared using protein-A agarose beads (ROCHE™, Mannheim, Germany) and 10% input was collected. Immunoprecipitations were performed using polyclonal antibodies to H3K₄-trimethylated, H3K27 trimethylated and normal rabbit serum (Upstate, Temucula, Calif.). DNA-protein complexes were pulled-down using Protein-A agarose beads and washed. DNA was recovered by overnight incubation at 65° C. to reverse cross-links and purified using QIAQUICK™ PCR purification columns (QIAGEN™, Maryland). Enrichment of the modified histones in different genes was detected by quantitative real time PCR.

| Promotor | forward | reverse |
|---|---|---|
| Oct4 | AAAGCAATCCTTCTGCTCCA | TAACATAGCAAGGCCCCATC |
| Sox2 | GCGTCCCATCCTCATTTAAG | GCCTTTTCGAAGGAAGTGG |
| Nanog | CACGGCCTCCCAATTTACT | TGGTTCAACAGGAATGGGATA |
| Zfp42 (Rex1) | TCCGGCCTAAAAGGGTAAAT | GTTGGCACGTGGTGAGC |
| Zfp42 (Rex1) | CGCGTCCGGCCTAAA | GGCAGCGCCTCCAGA |
| DNMT3b | GTCCAAAGCAGGATGACAGG | GCACCAGAGTCTCCGCTTTA |
| Sal4 | CCATCCTTGCTCCAGCTATC | GCCGTTCCAAAACTTCTACG |
| Actin | GTGGACATCTCTTGGGCACT | TCTGCAGGAGCGTACAGAAC |

Immunostaining

Cells were fixed in 4% paraformaldehyde for 10-30 mins at room temperature and permeabilized for 15 mins with 0.2% Triton-X in PBS. Cells were then blocked for non-specific binding with 10% normal goat or donkey serum (ABCAM™) in PBS overnight at 4° C. Primary antibodies were added and incubated with the samples at room temperature for 1 hour. Samples were rinsed with PBS and incubated with the appropriate fluorescently labeled secondary antibodies (INVITROGEN™) for 2 h at room temperature. Primary antibodies used were: α-TRA-1-60, α-SSEA-3, α-SSEA-4, α-TRA-1-81, α-Sox2 (all from MILLIPORE™), α-SSEA1, α-Stat3 (both from CELL SIGNALING™), α-Oct4, α-Nanog (both from ABCAM™), α-TuJ1 (COVENANCE™), α-SMA (SIGMA™) and α-AFP (SANTA CRUZ BIOTECHNOLOGIES™). The nuclei were visualized with DAPI.

Western Blotting

Cells were lysed using RIPA buffer containing proteinase inhibitors. The protein concentration was estimated using Bradford reagents and equal amounts of protein were run on 4-12% Bis-Tris Gels (INVITROGEN™) and transferred to PVDF membranes (MILLIPORE™). Primary antibodies used were: Phospho-Stat3, Stat3, E-Cadherin (all CELL SIGNALING™) and Tubulin (SIGMA™). HRP coupled secondary antibody was from Cell Signalling.

Example 7

Small Molecule Inhibitors of PKA and GSK3β Signaling can Enhance Transgene Introduction in Human ES Cells and in Human Pluripotent Stem Cells Small molecule inhibitors of glycogen synthase kinase beta and the mitogen-activated protein kinase (MAPK) signaling pathway can replace some of the reprogramming factors during iPS cell generation.

It was therefore sought to explore if small molecule inhibitors can affect human pluripotent stem cell colony morphology, proliferation and the ability to introduce transgenes using homologous recombination. Human pluripotent stem cells were maintained in standard medium (DMEM/F12 containing 20% knockout serum replacement, 2 mM L-Glutamine, 1% non-essential amino acids, 100 U of penicillin, 100 μg streptomycin, 0.1 mM beta-mercaptoethanol and 5 ng/mL bFGF, with or without pharmacological inhibitors.

Figure 12A:
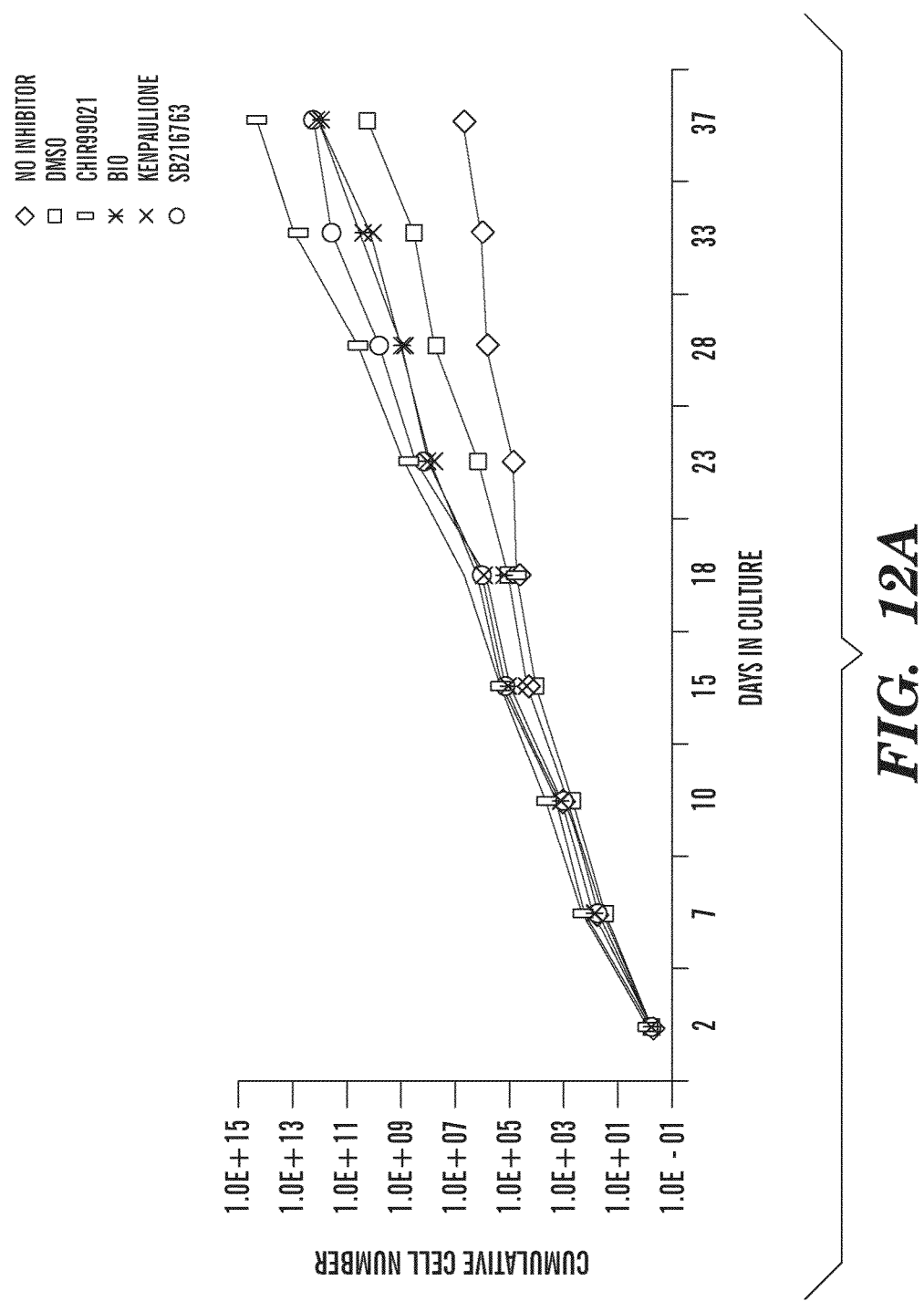
FIGS. 12A-12C: Inhibition of PKA or GSK3β signaling enhances human pluripotent stem cell proliferation rate and improves the introduction of transgenes by homologous recombination. 12A. Cell proliferation curve. Cell numbers of human iPS cells were counted at the indicated time intervals. Plotted is the cumulative cell number over 37 days of culture. All cells were maintained in standard human iPS culture conditions (e.g., Maherali et al. *Cell Stem Cell* 2008, 3:340-345) with indicated additions: DMSO (PKA inhibitor, 0.1%); CHIR99021 (GSK3β inhibitor, 3 μM), Kenpaullone (GSK3β inhibitor, 5 μM); BIO (GSK3β inhibitor, 15 μM) and SB216763 (GSK3β inhibitor, 1 μM). 12B Colony morphology of human pluripotent stem cells cultured in the presence of the GSK3β inhibitor (3 μM) and PD98059 (50 μM). 12C Influence of signaling inhibitors on the introduction of a 10 kb transgene construct carrying a puromycin selection cassette. Puromycin selection was applied at 0.25 μg/mL 48 hours after electroporation of human iPS cells with 20 μg of the linearized plasmid.
Figures 12B, 12C:
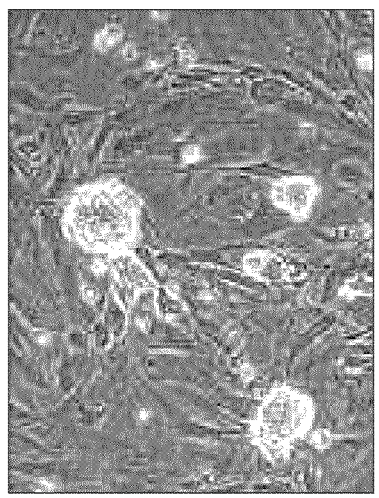

Inhibition of PKA (DMSO) or GSK3beta allowed trypsin passaging of the cells and enhanced the pluripotent stem cell proliferation rate. In addition, in the presence of the GSK3β inhibitor CHIR99021 (3 μM) and the MEK inhibitor PD98059 (50 μM), human pluripotent stem cells (both ES cells and iPS cells) adopted the characteristic tight dome-shaped morphology of murine ES cells. Finally, using inhibitors of PKA signaling and GSKbeta, it was demonstrated that inhibition of these signaling pathways enhances the ability to introduce transgenes into human pluripotent stem cells as shown by their enhanced colony formation upon the electroporation of a 10 kb linearized plasmid carrying a puromycin-resistance homologous recombination cassette, after subsequent puromycin selection. The data are shown in FIGS. 12A-12C. The inhibition of GSK3β can increase the frequency of homologous recombination in both iPS cells derived in the presence of the five reprogramming factors as described above, and in human ES cells. The human ES cells acquired a mouse ES cell-like morphology, became capable of single cell expansion, and became capable of trypsin passaging when incubated with a GSK3β inhibitor. The effect and the increase in homologous recombination could be facilitated by co-addition of MEK inhibitor(s).

The invention claimed is:

1. A composition comprising:
   (a) a human pluripotent stem cell in admixture with a GSK3β inhibitor and a protein kinase A (PKA) inhibitor, and
   (b) a homologous recombination cassette.

2. The composition of claim 1, wherein the human pluripotent stem cell in the admixture is an iPS cell or an embryonic stem cell.

3. The composition of claim 1, wherein the GSK3β inhibitor is selected from the group consisting of: CHIR99021, BIO, Kenpaullone, and SB216763.

4. The composition of claim 1, wherein the human pluripotent stem cell in the admixture has an enhanced efficiency of homologous recombination compared to a corresponding human pluripotent stem cell not in an admixture with the GSK3β inhibitor.

5. The composition of claim 4, wherein the efficiency of homologous recombination is enhanced by at least 50% compared to a corresponding human pluripotent stem cell not in the admixture with the GSK3β inhibitor.

6. The composition of claim 1, wherein the human pluripotent stem cell in the admixture survives expansion from, or can be expanded from, a single cell and wherein a corresponding human pluripotent stem cell not in an admixture with the GSK3β inhibitor does not survive expansion from, or cannot be expanded from, a single cell.

7. The composition of claim 1, wherein the human pluripotent stem cell in the admixture survives passaging from a single cell by a non-collagenase digest, and wherein the corresponding human pluripotent stem cell not in an admixture with the GSK3β inhibitor does not survive passaging from a single cell by a non-collagenase digest.

8. The composition of claim 1, wherein the human pluripotent stem cell in the admixture survives passaging from a single cell by trypsin digest, and wherein the corresponding human pluripotent stem cell not in an admixture with the GSK3β inhibitor does not does not survive passaging from a single cell by trypsin digest.

9. The composition of claim 1, wherein the human pluripotent stem cell has a faster growth rate compared to the growth rate of a corresponding human pluripotent stem cell not in an admixture with the GSK3β inhibitor.

10. The composition of claim 9, wherein the growth rate is assessed by measuring doubling time.

11. The composition of claim 10, wherein the doubling time is at least 2 hours faster than the growth rate of a corresponding human pluripotent stem cell not in an admixture with the GSK3β inhibitor.

12. The composition of claim 1, further comprising a MEK inhibitor.

13. The composition of claim 12, wherein the MEK inhibitor is PD98059.

14. A stem cell composition comprising:
    (a) a human pluripotent stem cell clone isolated from a population of pluripotent stem cells treated with a GSK3β inhibitor and a protein kinase A (PKA) inhibitor having the following characteristics:
        (i) survives propagation from a single cell,
        (ii) an efficiency of homologous recombination at least 1-fold higher than the efficiency of homologous recombination in a corresponding human pluripotent stem cell not treated with the GSK3β inhibitor,
        (iii) a doubling time at least 2 hours faster than the growth rate of a corresponding human pluripotent stem cell not treated with the GSK3β inhibitor,
        (iv) survives passaging as a single cell using trypsin digest, and
    (b) a homologous recombination cassette.

15. The composition of claim 14, wherein the GSK3β inhibitor is selected from the group consisting of: CHIR99021, BIO, Kenpaullone, and SB216763.

16. The composition of claim 14, wherein the population of pluripotent stem cells is further treated with a MEK inhibitor.

17. The composition of claim 16, wherein the MEK inhibitor is PD98059.

18. The composition of claim 14, wherein the human pluripotent stem cell is an iPS cell or an embryonic stem cell.

19. The composition of claim 14, wherein the doubling time is 15-30 hours.

20. The composition of claim 14, wherein the doubling time is 20-24 hours.

21. A kit for enhancing the efficiency of homologous recombination in a human stem cell, the kit comprising:
    (a) a GSK3β inhibitor,
    (b) a protein kinase A (PKA) inhibitor,
    (c) a homologous recombination cassette, and
    (d) instructions and packaging thereof.

22. The kit of claim 21, wherein the GSK3β inhibitor is selected from the group consisting of: CHIR99021, BIO, Kenpaullone, and SB216763.

23. The kit of claim 21, further comprising a MEK inhibitor.

24. The kit of claim 23, wherein the MEK inhibitor is PD98059.

* * * * *